US012642930B2

(12) United States Patent
Dantanarayana

(10) Patent No.: US 12,642,930 B2
(45) Date of Patent: Jun. 2, 2026

(54) VENT STRUCTURE FOR A RESPIRATORY THERAPY SYSTEM

(71) Applicant: RESMED PTY LTD, Bella Vista (AU)

(72) Inventor: Muditha Pradeep Dantanarayana, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 830 days.

(21) Appl. No.: 17/891,712

(22) Filed: Aug. 19, 2022

(65) Prior Publication Data

US 2023/0062214 A1 Mar. 2, 2023

(30) Foreign Application Priority Data

Aug. 20, 2021 (AU) ................................. 2021902613
Nov. 18, 2021 (AU) ................................. 2021903711
(Continued)

(51) Int. Cl.
*A61M 16/06* (2006.01)
*A61M 16/08* (2006.01)
*A61M 16/16* (2006.01)

(52) U.S. Cl.
CPC ........ *A61M 16/06* (2013.01); *A61M 16/0616* (2014.02); *A61M 16/16* (2013.01); *A61M 16/0666* (2013.01)

(58) Field of Classification Search
CPC ....... A61B 5/083; A61B 5/087; A61B 5/0876; A61B 5/09; A61B 5/097; A61M 11/041;
(Continued)

(56) References Cited

U.S. PATENT DOCUMENTS 2,944,547 A 7/1960 Ziherl et al.
3,109,425 A 11/1963 Gongoll
(Continued)

FOREIGN PATENT DOCUMENTS

CN 101098727 A 1/2008
CN 101516300 A 8/2009
(Continued)

OTHER PUBLICATIONS

Communication pursuant to Article 94(3) EPC dated Feb. 12, 2026, received in EP Application No. 24189669.5, 5 pages.

*Primary Examiner* — Annette Dixon
(74) *Attorney, Agent, or Firm* — NIXON & VANDERHYE, PC

(57) ABSTRACT

A vent structure for a respiratory therapy system may comprise a vent housing and a membrane within the vent housing. The vent housing may define a first flow path between an air circuit and a plenum chamber of a patient interface, and a second flow path between the first flow path and surrounding ambient air. The first flow path passes through a central aperture of the membrane. A first side and opposite second side of the membrane may both be exposed to air flow in the first flow path in use. When air flows from the air circuit to the plenum chamber the membrane may adopt a first configuration in which air flow to the second flow path is partially blocked. When air flows from the plenum chamber to the air circuit the membrane may adopt a second configuration allowing air flow from the first to the second flow path.

19 Claims, 55 Drawing Sheets

(30)        Foreign Application Priority Data

| Dec. 22, 2021 | (AU) | ................................ | 2021904191 |
| Apr. 14, 2022 | (AU) | ................................ | 2022900997 |
| May 18, 2022 | (AU) | ................................ | 2022901329 |

(58) Field of Classification Search

CPC .............. A61M 11/042; A61M 11/047; A61M 15/0016; A61M 15/0018; A61M 15/0086; A61M 15/009; A61M 15/08; A61M 16/00; A61M 16/0009; A61M 16/0048; A61M 16/0057; A61M 16/0066; A61M 16/0078; A61M 16/0084; A61M 16/009; A61M 16/0096; A61M 16/04; A61M 16/0468; A61M 16/0495; A61M 16/06; A61M 16/0611; A61M 16/0616; A61M 16/0622; A61M 16/0633; A61M 16/065; A61M 16/0666; A61M 16/0683; A61M 16/08; A61M 16/0816; A61M 16/0825; A61M 16/0833; A61M 16/085; A61M 16/0858; A61M 16/0875; A61M 16/1045; A61M 16/106; A61M 16/107; A61M 16/1075; A61M 16/109; A61M 16/12; A61M 16/127; A61M 16/14; A61M 16/20; A61M 16/201; A61M 16/206; A61M 16/207; A61M 16/208; A61M 16/209; A61M 16/22; A61M 2016/0021; A61M 2016/0027; A61M 2016/0042; A61M 2021/0016; A61M 2202/0085; A61M 2202/0208; A61M 2202/0225; A61M 2205/0216; A61M 2205/0238; A61M 2205/332; A61M 2205/42; A61M 2205/43; A61M 2205/581; A61M 2205/583; A61M 2205/59; A61M 2205/7527; A61M 2205/7536; A61M 2205/8206; A61M 2206/10; A61M 2210/0618; A62B 18/00; A62B 18/02; A62B 18/10; A62B 9/02; A62B 9/022; A62B 9/027; B63C 11/186; B63C 11/2227; B63C 9/00; F16K 15/1401; F16K 15/1402; F16K 15/144; F16K 15/145; F16K 15/147; F16K 15/148; F16K 15/16; F24F 8/50; G01F 1/28; G09B 23/288; Y10S 128/912; Y10S 251/901; Y10T 137/0318; Y10T 137/2012; Y10T 137/2544; Y10T 137/2546; Y10T 137/2572; Y10T 137/7766; Y10T 137/7771; Y10T 137/7781; Y10T 137/782; Y10T 137/784; Y10T 137/7841; Y10T 137/7842; Y10T 137/7843; Y10T 137/7879; Y10T 137/7882; Y10T 137/7884; Y10T 137/789; Y10T 137/7891; Y10T 137/8242; Y10T 137/87555

See application file for complete search history.

(56)        References Cited

U.S. PATENT DOCUMENTS

| 3,688,794 | A | | 9/1972 | Forrest |
| 3,942,547 | A | | 3/1976 | Pfitzner |
| 3,995,625 | A | | 12/1976 | Needham |
| 4,007,758 | A | | 2/1977 | Gray |
| 4,354,520 | A | | 10/1982 | Easley |
| 4,406,302 | A | | 9/1983 | Olesen |
| 4,458,679 | A | | 7/1984 | Ward |
| RE32,553 | E | | 12/1987 | Bennett |
| 4,782,832 | A | | 11/1988 | Trimble et al. |
| 4,944,310 | A | | 7/1990 | Sullivan |
| 4,997,217 | A | | 3/1991 | Kunze |
| 5,002,050 | A | | 3/1991 | McGinnis |
| 5,005,568 | A | * | 4/1991 | Loescher ............ A61M 16/107 |
| | | | | 128/202.28 |
| 5,103,854 | A | * | 4/1992 | Bailey ................. F16K 15/1402 |
| | | | | 128/205.24 |
| 5,127,400 | A | | 7/1992 | Devries |
| 5,271,601 | A | | 12/1993 | Bonzer et al. |
| 5,647,355 | A | | 7/1997 | Starr |
| 5,685,296 | A | | 11/1997 | Zdrojkowski et al. |
| 5,687,715 | A | | 11/1997 | Landis |
| 5,738,087 | A | | 4/1998 | King |
| 5,762,382 | A | | 6/1998 | Pernetti et al. |
| 5,896,857 | A | | 4/1999 | Hely et al. |
| 5,937,851 | A | | 8/1999 | Serowski et al. |
| 5,979,444 | A | | 11/1999 | Sherrod |
| 6,189,532 | B1 | | 2/2001 | Hely et al. |
| 6,427,692 | B1 | | 8/2002 | Höglund |
| 6,532,959 | B1 | | 3/2003 | Berthon-Jones |
| 6,561,190 | B1 | | 5/2003 | Kwok |
| 6,561,191 | B1 | | 5/2003 | Kwok |
| 6,581,594 | B1 | | 6/2003 | Drew et al. |
| 6,584,977 | B1 | | 7/2003 | Serowski |
| 6,662,803 | B2 | | 12/2003 | Gradon et al. |
| 7,089,939 | B2 | * | 8/2006 | Walker ................. A61M 16/06 |
| | | | | 128/205.24 |
| 7,096,864 | B1 | | 8/2006 | Mayer et al. |
| 7,134,434 | B2 | | 11/2006 | Truitt et al. |
| 7,302,950 | B2 | | 12/2007 | Berthon-Jones et al. |
| 7,559,326 | B2 | | 7/2009 | Smith et al. |
| 7,866,944 | B2 | | 1/2011 | Kenyon et al. |
| 7,987,847 | B2 | | 8/2011 | Wickham |
| 7,987,851 | B2 | | 8/2011 | Blom |
| 8,365,731 | B2 | | 2/2013 | Ho et al. |
| 8,439,035 | B2 | | 5/2013 | Dantanarayana et al. |
| 8,496,004 | B2 | | 7/2013 | Lang et al. |
| 8,544,465 | B2 | | 10/2013 | Smith et al. |
| 8,573,201 | B2 | | 11/2013 | Rummery |
| 8,573,208 | B2 | | 11/2013 | Ho |
| 8,636,479 | B2 | | 1/2014 | Kenyon et al. |
| 8,638,014 | B2 | | 1/2014 | Sears et al. |
| 8,733,349 | B2 | | 5/2014 | Bath et al. |
| 9,808,594 | B2 | | 11/2017 | Dantanarayana et al. |
| 9,861,774 | B2 | | 1/2018 | Fu et al. |
| 10,004,924 | B1 | | 6/2018 | Anderson |
| 10,086,166 | B1 | | 10/2018 | Nashed |
| 10,220,179 | B2 | | 3/2019 | Dantanarayana et al. |
| 10,898,662 | B2 | | 1/2021 | Huddart |
| 2003/0037788 | A1 | | 2/2003 | Gallem |
| 2003/0079751 | A1 | | 5/2003 | Kwok |
| 2004/0255948 | A1 | | 12/2004 | Smith |
| 2009/0044808 | A1 | | 2/2009 | Guney et al. |
| 2009/0050156 | A1 | | 2/2009 | Ng et al. |
| 2009/0120434 | A1 | | 5/2009 | Smith et al. |
| 2009/0133694 | A1 | | 5/2009 | Solci et al. |
| 2009/0260628 | A1 | | 10/2009 | Flynn |
| 2010/0000534 | A1 | | 1/2010 | Kooij et al. |
| 2010/0083969 | A1 | | 4/2010 | Crumblin et al. |
| 2010/0282262 | A1 | | 11/2010 | Boussignac |
| 2011/0067709 | A1 | | 3/2011 | Doshi et al. |
| 2012/0325205 | A1 | | 12/2012 | Allum et al. |
| 2012/0325218 | A1 | | 12/2012 | Brambilla et al. |
| 2013/0184602 | A1 | | 7/2013 | Brambilla |
| 2015/0114504 | A1 | | 4/2015 | Cecka et al. |
| 2015/0136137 | A1 | * | 5/2015 | Bugamelli .......... A61M 16/206 |
| | | | | 137/848 |
| 2016/0310688 | A1 | | 10/2016 | Rothermel |
| 2016/0361575 | A1 | | 12/2016 | Gerson |
| 2018/0200467 | A1 | | 7/2018 | Finch |
| 2018/0207389 | A1 | | 7/2018 | Fyfe |
| 2018/0344953 | A1 | | 12/2018 | Cegla |
| 2019/0001095 | A1 | | 1/2019 | Rose |
| 2019/0105458 | A1 | | 4/2019 | Hammes |
| 2019/0209804 | A1 | | 7/2019 | Dantanarayana |

(56)                     References Cited

U.S. PATENT DOCUMENTS

2019/0351173 A1 * 11/2019 Dantanarayana ............................
                                                                A61M 16/0875
2020/0188620 A1     6/2020 Markwardt et al.

FOREIGN PATENT DOCUMENTS

| | | | |
|---|---|---|---|
| CN | 202951092 U | 5/2013 |
| CN | 108136150 A | 6/2018 |
| EP | 1027905 A2 | 8/2000 |
| EP | 3 352 830 B1 | 4/2021 |
| GB | 2500061 A1 | 9/2013 |
| JP | 2001-506883 A | 5/2001 |
| JP | 2004-522487 | 7/2004 |
| JP | 2008-540056 | 11/2008 |
| JP | 2013-501541 A | 1/2013 |
| WO | 98/04310 A1 | 2/1998 |
| WO | 98/26830 A1 | 6/1998 |
| WO | 98/34665 A1 | 8/1998 |
| WO | 2000/078381 A1 | 12/2000 |
| WO | 02/051486 A1 | 7/2002 |
| WO | 2004/073778 A1 | 9/2004 |
| WO | 2005/063326 A1 | 7/2005 |
| WO | 2005/063328 A1 | 7/2005 |
| WO | 2006/074513 A1 | 7/2006 |
| WO | 2006/130903 A1 | 12/2006 |
| WO | 2009/052560 A1 | 4/2009 |
| WO | 2010/135785 A1 | 12/2010 |
| WO | 2011/080604 A1 | 7/2011 |
| WO | 2012/171072 A1 | 12/2012 |
| WO | 2013/020167 A1 | 2/2013 |
| WO | 2014/097068 A1 | 6/2014 |
| WO | 2014/129913 A1 | 8/2014 |
| WO | 2014/205513 A1 | 12/2014 |
| WO | 2015/013761 A1 | 2/2015 |
| WO | 2015/041545 A1 | 3/2015 |
| WO | 2015/052681 A1 | 4/2015 |
| WO | 2015/073824 A1 | 5/2015 |
| WO | 2016/041019 A1 | 3/2016 |
| WO | 2016/141430 A1 | 9/2016 |
| WO | 2017/014647 A1 | 1/2017 |
| WO | 2017/021836 A1 | 2/2017 |
| WO | 2017/049358 A1 | 3/2017 |
| WO | 2018/052673 A1 | 3/2018 |
| WO | 2018/053589 A1 | 3/2018 |
| WO | 2018/126295 A1 | 7/2018 |
| WO | WO-2019212404 A1 * | 11/2019 | .......... F16K 15/147 |
| WO | 2020/172708 A1 | 9/2020 |

* cited by examiner

Nasal cavity

Oral cavity

Larynx

Vocal folds

Oesophagus

Trachea

Bronchus

Lung

Heart

Diaphragm

Alveolar sacs

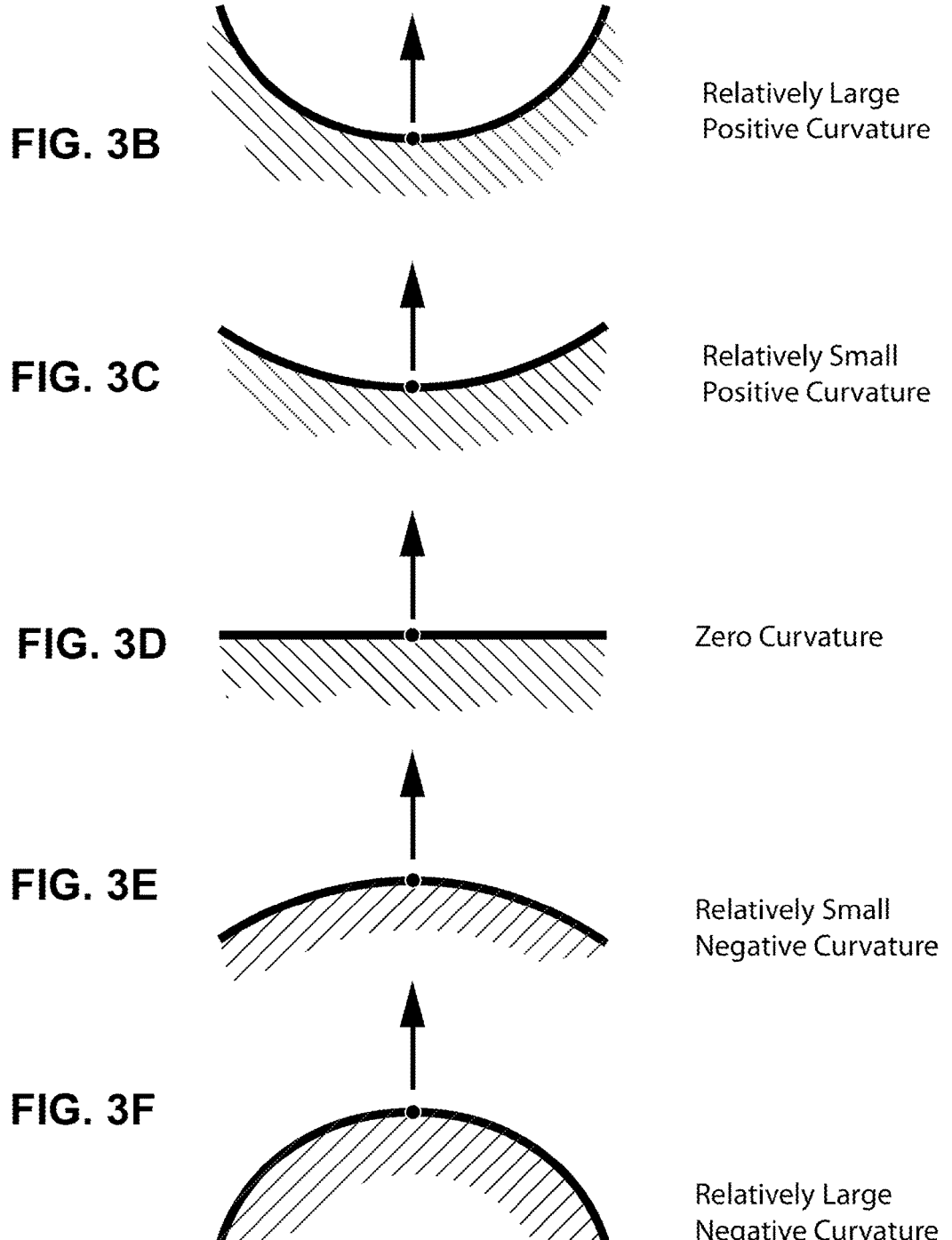
FIG. 3B          Relatively Large
                 Positive Curvature
FIG. 3C          Relatively Small
                 Positive Curvature
FIG. 3D          Zero Curvature
FIG. 3E          Relatively Small
                 Negative Curvature
FIG. 3F          Relatively Large
                 Negative Curvature

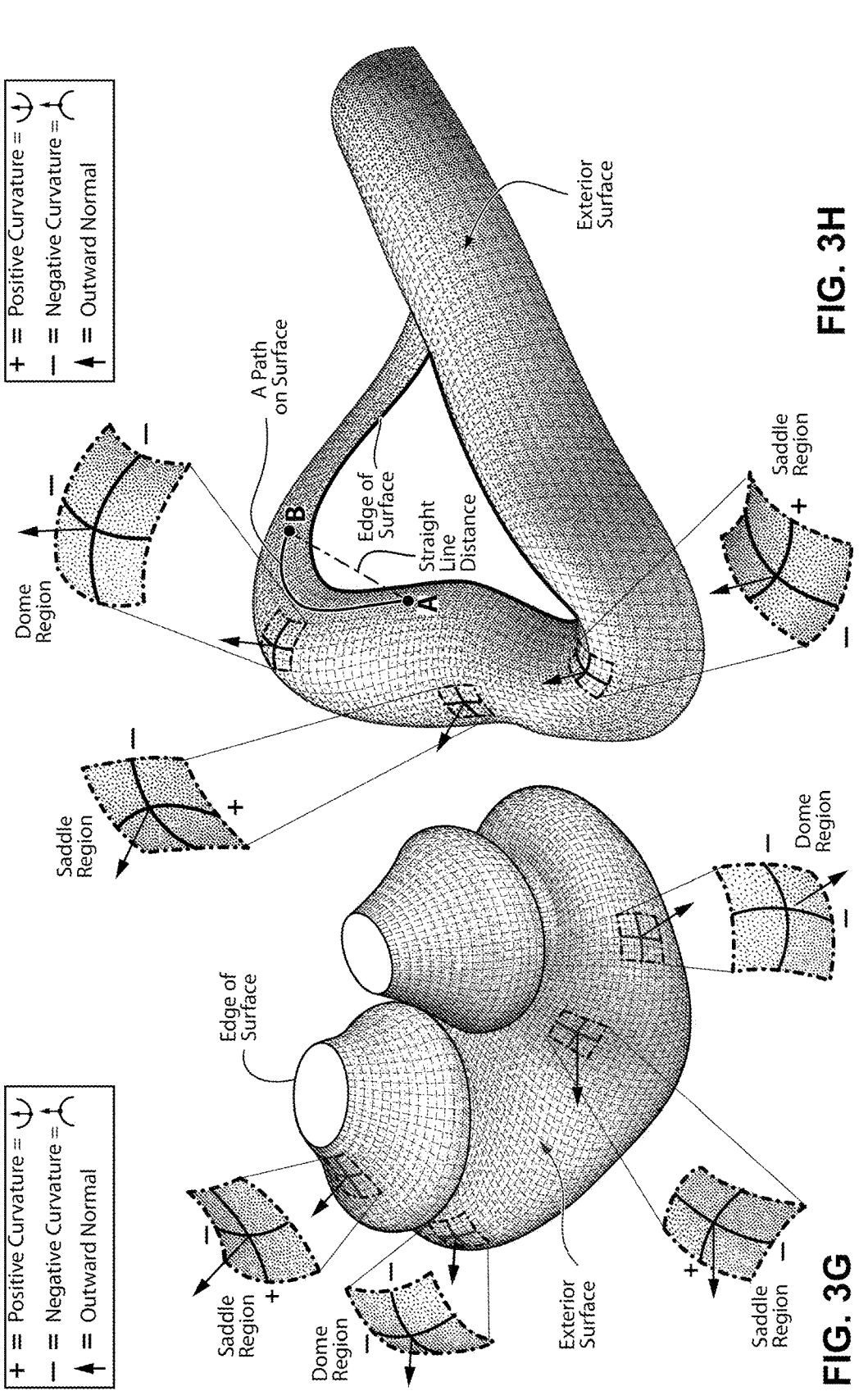

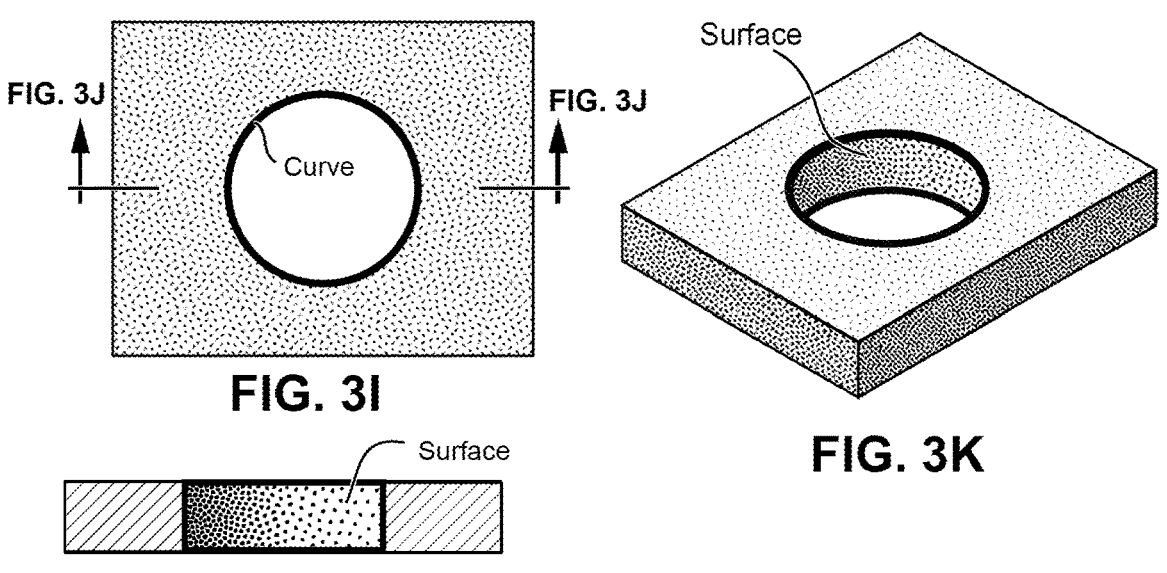
FIG. 3I
FIG. 3K
FIG. 3J
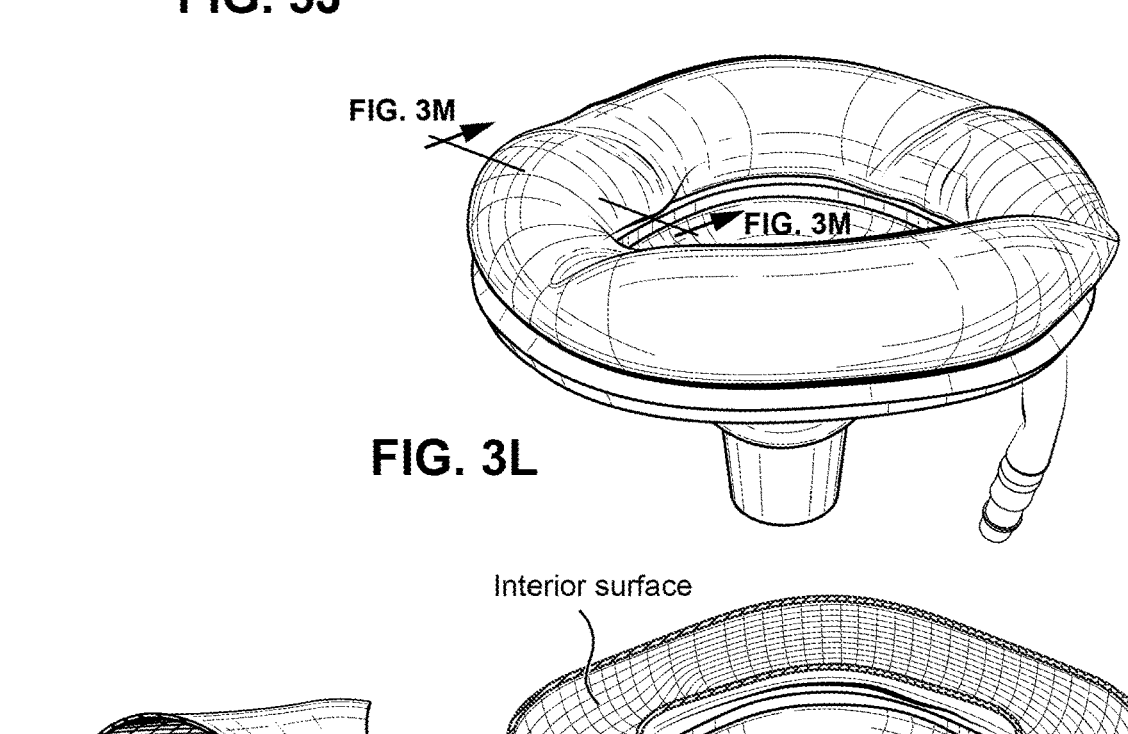
FIG. 3L
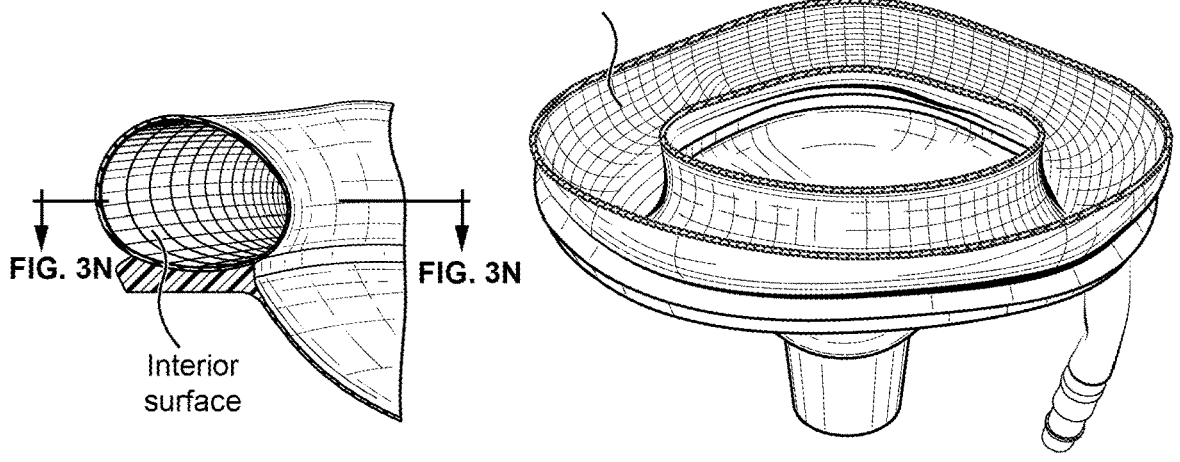
FIG. 3M    FIG. 3N

Left-hand rule
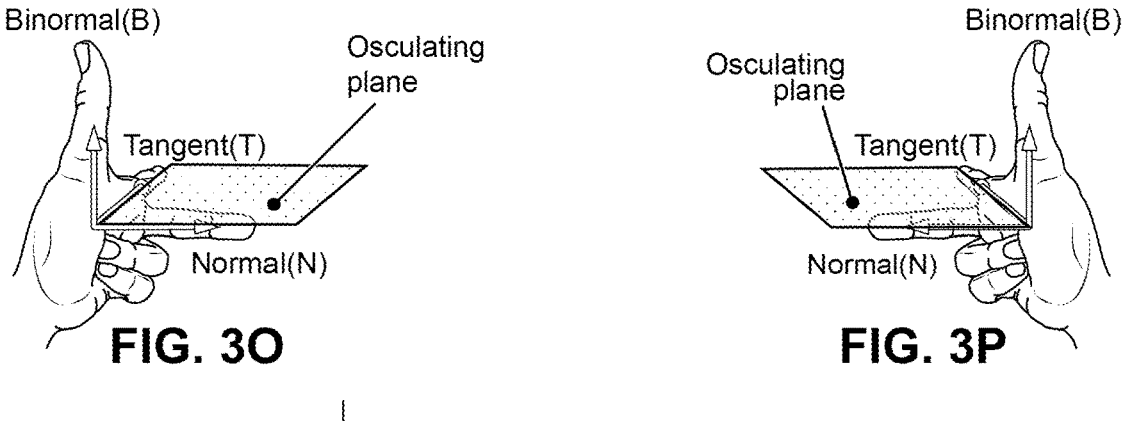
Binormal(B)
Osculating plane
Tangent(T)
Normal(N)
FIG. 3O
Right-hand rule
Binormal(B)
Osculating plane
Tangent(T)
Normal(N)
FIG. 3P
Left ear helix
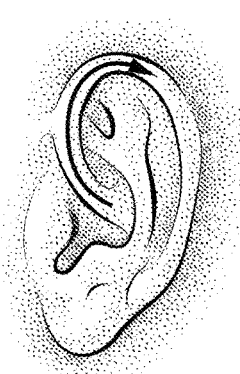
FIG. 3Q
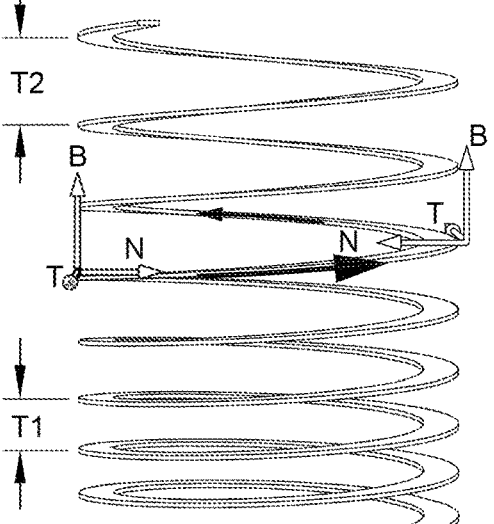
T2
B
N
N
T
B
T
T1
Right-hand helix
Right-hand positive
FIG. 3S
Right ear helix
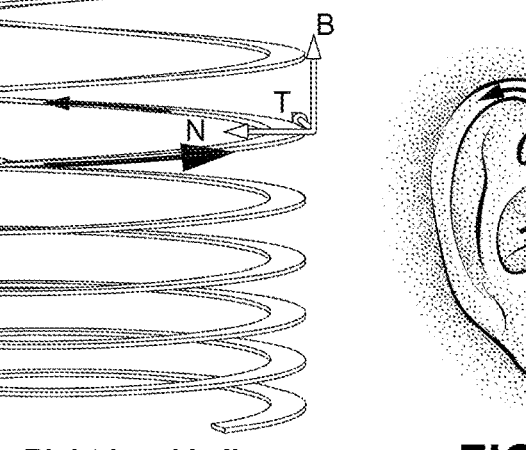
FIG. 3R
Right-hand negative (=left-hand positive)    Right-hand positive    Right-hand negative
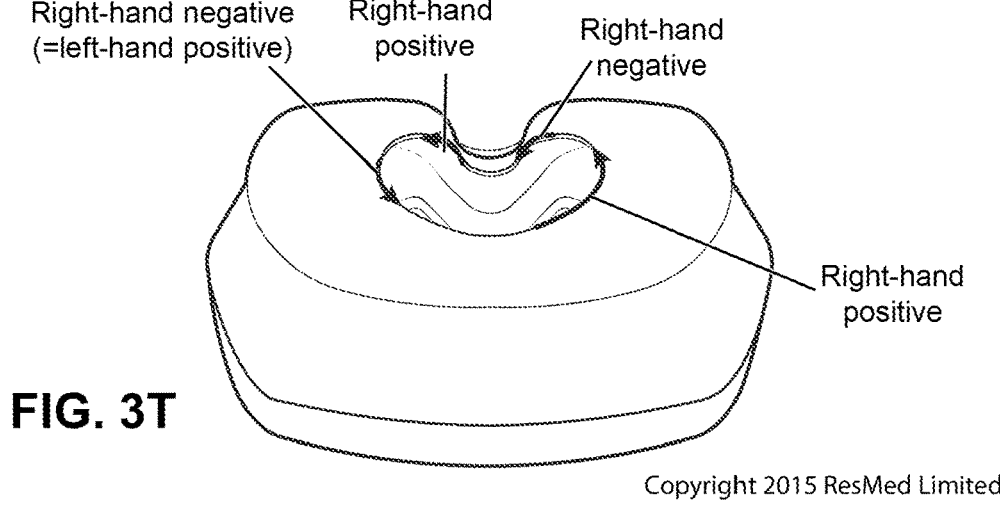
Right-hand positive
FIG. 3T

VENT STRUCTURE FOR A RESPIRATORY THERAPY SYSTEM

1 CROSS-REFERENCE TO RELATED APPLICATIONS

This application claims the benefit of Australian Application No. 2021902613, filed Aug. 20, 2021, Australian Application No. 2021904191, filed Dec. 22, 2021, Australian Application No. 2022901329, filed May 18, 2022, Australian Application No. 2021903711, filed Nov. 18, 2021, and Australian Application No. 2022900997, filed Apr. 14, 2022, each of which is incorporated herein by reference in its entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

2.2.3.1.2 Positioning and Stabilising Structure

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face. Several factors may be considered when comparing different positioning and stabilising techniques. These include: how effective the technique is at maintaining the seal-forming structure in the desired position and in sealed engagement with the face during use of the patient interface; how comfortable the interface is for the patient; whether the patient feels intrusiveness and/or claustrophobia when wearing the patient interface; and aesthetic appeal.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Pressurised Air Conduit

In one type of treatment system, a flow of pressurised air is provided to a patient interface through a conduit in an air circuit that fluidly connects to the patient interface at a location that is in front of the patient's face when the patient interface is positioned on the patient's face during use. The conduit may extend from the patient interface forwards away from the patient's face.

2.2.3.1.4 Pressurised Air Conduit Used for Positioning/Stabilising the Seal-Forming Structure Another type of treatment system comprises a patient interface in which a tube that delivers pressurised air to the patient's airways also functions as part of the headgear to position and stabilise the seal-forming portion of the patient interface at the appropriate part of the patient's face. This type of patient interface may be referred to as having "conduit headgear" or "headgear tubing". Such patient interfaces allow the conduit in the air circuit providing the flow of pressurised air from a respiratory pressure therapy (RPT) device to connect to the patient interface in a position other than in front of the patient's face. One example of such a treatment system is disclosed in US Patent Publication No. US 2007/0246043, the contents of which are incorporated herein by reference, in which the conduit connects to a tube in the patient interface through a port positioned in use on top of the patient's head.

It is desirable for patient interfaces incorporating headgear tubing to be comfortable for a patient to wear over a prolonged duration when the patient is asleep, form an air-tight and stable seal with the patient's face, while also able to fit a range of patient head shapes and sizes.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed MirageTM (*) | nasal | 29.5 | 21.5 | 1998 |
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |

-continued

| Mask name | Mask type | A-weighted sound power level dB(A) (uncertainty) | A-weighted sound pressure dB(A) (uncertainty) | Year (approx.) |
|---|---|---|---|---|
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |
| ResMed Mirage SwiftTM LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One aspect of the present technology is a vent structure for a respiratory therapy system. The vent structure may be configured in use to convey a vent flow of gases exhaled by a patient from an interior volume of the respiratory therapy system to surrounding ambient air.

In one form, the vent structure may comprise a vent housing. The vent housing may define a first flow path between a first port configured to connect in use to an air circuit and a second port configured to connect in use to a plenum chamber of a patient interface. The vent housing may further define a second flow path between the first flow path and surrounding ambient air.

In certain forms, the vent structure may further comprise a membrane positioned within the vent housing. The membrane may comprise a central aperture through which the first flow path passes. The membrane may be positioned in the vent housing such that a first side of the membrane and a second side of the membrane opposite the first side are both exposed to air flow in the first flow path in use.

In certain forms, the vent structure may be configured such that in use when air flows in the first flow path from the first port to the second port, the membrane adopts a first configuration to at least partially block air flow from the first flow path to the second flow path. The vent structure may be further configured such that in use when air flows in the first flow path from the second port to the first port, the membrane adopts a second configuration to allow air flow from the first flow path to the second flow path.

In certain forms, the membrane may comprise one or more protrusions extending from an inner perimeter of the membrane towards the centre of the aperture.

In examples: a) the vent housing defines a plurality of vent holes that form part of the second flow path and exit to the surrounding ambient air, the vent holes being positioned adjacent an outer perimeter of the membrane; b) the membrane is annular in shape; c) the membrane is circular in shape when projected onto a plane; d) the central aperture is circular in shape; e) the membrane comprises one or more protrusions extending from an inner perimeter of the membrane towards the centre of the aperture; f) the protrusions are symmetrically arranged around the circumference of the inner perimeter of the membrane; g) the membrane comprises a protrusion that extends across the aperture; h) the vent structure further comprises a diffuser configured to diffuse the flow of air exiting the vent structure; i) the vent structure comprises a first tube portion configured to connect to the plenum chamber, the first tube portion forming the second port; j) the diffuser is located around an outside surface of the first tube portion; k) the diffuser is located at a region of the first tube portion offset from an exit of the second flow path; l) the first tube portion comprises a first flange extending away from the first flow path at an end of the first tube portion distal from the second port; m) the membrane is positioned adjacent and substantially parallel to the first flange; n) a gap between the first side of the membrane and the first flange forms a part of the second flow path; o) the gap is sized to allow air to flow through the second flow path when the pressure in the first flow path drops below a threshold pressure to allow for adequate carbon dioxide washout in use; p) the first tube portion comprises a retaining member configured to retain the membrane; q) the retaining member engages the aperture of the membrane; r) the membrane comprises a plurality of membrane passive vent holes configured to allow air to flow from the first flow path to the second flow path when the membrane is in the first configuration; s) the first tube portion comprises a plurality of tube passive vent holes configured to allow air to flow directly from the first flow path to the surrounding ambient air; t) the plurality of tube passive vent holes are located in the region of the first tube portion adjacent the diffuser such that air flows from the first flow path through the diffuser and then to the surrounding ambient air; u) the first flange comprises the plurality of vent holes; v) the membrane is loosely contained within the vent housing; w) the entire membrane displaces away from the second port when air flows in the first flow path from the second port to the first port to allow the air to flow from the first flow path to the second flow path; x) the entire membrane displaces in a direction towards the second port when air flows in the first flow path from the first port to the second port to at least partially block air flow from the first flow path to the second flow path; y) the vent housing further comprises a second tube portion and a third tube portion each configured to connect to a respective tube of a positioning and stabilising structure; z) an outer portion around the circumference of the membrane is fixed to the vent housing; aa) an outer portion around the circumference of the membrane is fixed to the first tube portion; bb) an outer portion around the circumference of the membrane is fixed to the first flange of the first tube portion; cc) an inner portion of the membrane is configured to deflect in a direction away from the second port when air flows in the first flow path from the second port to the first port to allow air to flow from the first flow path to the second flow path; dd) the inner portion of the membrane is configured to deflect in a direction towards the second port when air flows in the first flow path from the first port to the second port to at least partially block air flow from the first flow path to the second flow path; ee) the vent structure further comprises a second tube portion configured to connect at one end to the first tube portion and at an opposite end to the air circuit; ff) the second tube portion comprises a second flange extending away from the first flow path at an end of the second tube portion proximal to the second port; and/or gg) the first flange is connected to the second flange.

Another aspect of certain forms of the technology is a patient interface for a respiratory therapy system. The patient interface may comprise a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient. The patient interface may further comprise a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use. The patient interface may be configured to allow the patient to breathe from ambient through their mouth in the absence of a flow of pressurised air through the plenum chamber inlet port, or the patient interface is configured to leave the patient's mouth uncovered.

In certain forms, the patient interface may further comprise a vent structure according to another aspect of the technology. The vent structure may allow a flow of gases exhaled by the patient from an interior of the plenum chamber to ambient, said vent structure being sized and shaped to maintain the therapeutic pressure in the plenum chamber in use.

In examples: a) the vent structure is connected to the plenum chamber; b) the first tube portion is connected to the plenum chamber in use; c) the patient interface further comprises a positioning and stabilising structure configured to provide a force to hold the seal-forming structure in a therapeutically effective position on the patient's head; d) the positioning and stabilising structure comprises one or more tubes configured to deliver pressurised air from an air circuit to the plenum chamber for delivery to the patient's airways, and wherein the vent structure is configured to connect to the one or more tubes; and/or e) the second tube portion and the third tube portion are configured to connect to the one or more tubes of the positioning and stabilising structure.

Another aspect of the technology is a respiratory therapy system comprising a patient interface according to another aspect of the technology. The respiratory therapy system may further comprise at least one air circuit for supplying the flow of gas at the therapeutic pressure to the patient interface.

In certain forms, the respiratory therapy system may comprise a vent structure according another aspect of the technology.

In certain forms, the air circuit may comprise a vent structure according to another aspect of the technology.

In certain forms, the respiratory therapy system may further comprise an elbow configured to connect the air circuit to the patient interface. The elbow may comprise a vent structure according to another aspect of the technology.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3A:
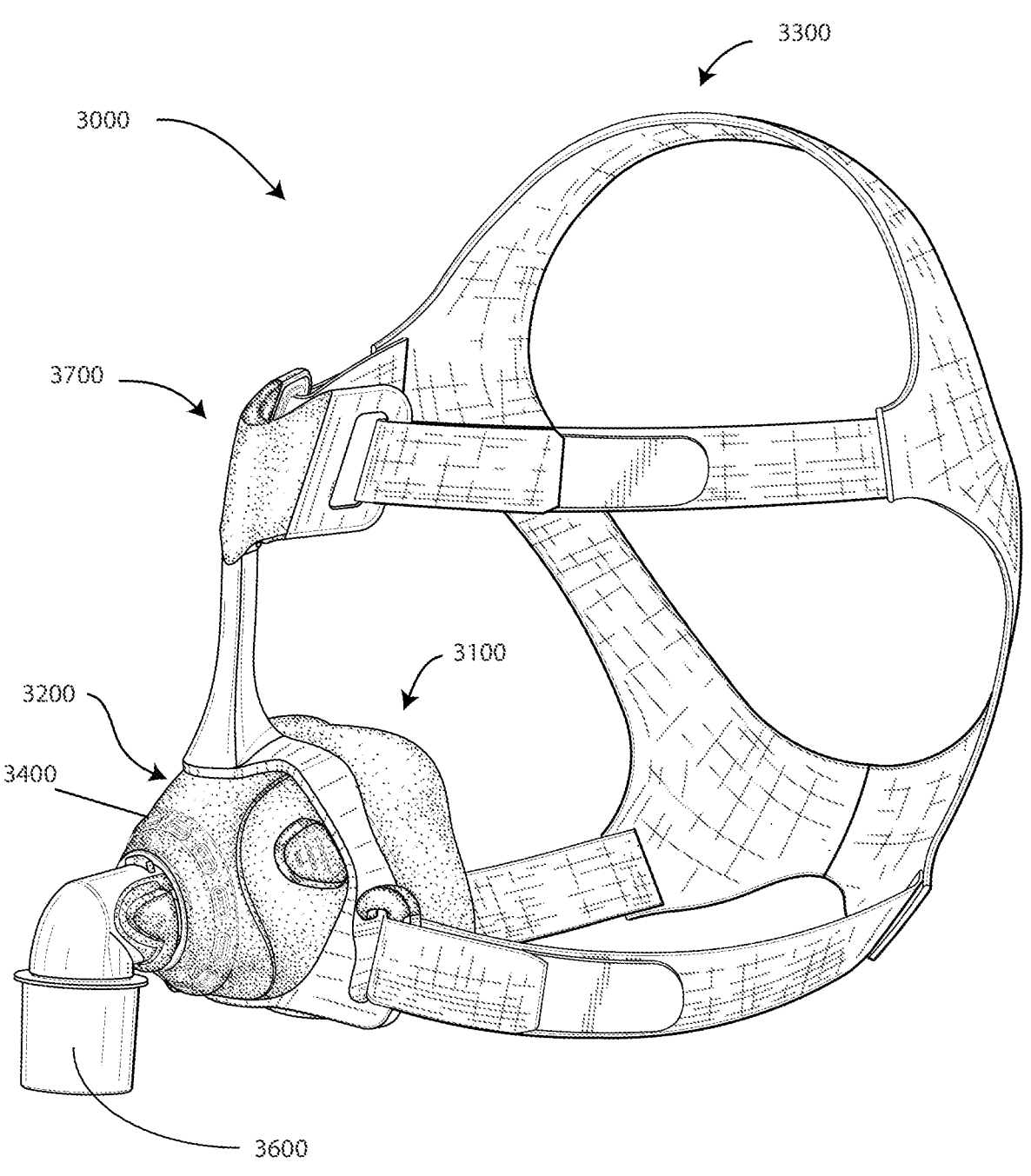
FIG. 3I shows the surface of a structure, with a one dimensional hole in the surface. The illustrated plane curve forms the boundary of a one dimensional hole.
FIG. 3J shows a cross-section through the structure of FIG. 3I. The illustrated surface bounds a two dimensional hole in the structure of FIG. 3I.
FIG. 3K shows a perspective view of the structure of FIG. 3I, including the two dimensional hole and the one dimensional hole. Also shown is the surface that bounds a two dimensional hole in the structure of FIG. 3I.
FIG. 3L shows a mask having an inflatable bladder as a cushion.
FIG. 3M shows a cross-section through the mask of FIG. 3L, and shows the interior surface of the bladder. The interior surface bounds the two dimensional hole in the mask.
FIG. 3N shows a further cross-section through the mask of FIG. 3L. The interior surface is also indicated.
FIG. 3O illustrates a left-hand rule.
FIG. 3P illustrates a right-hand rule.
FIG. 3Q shows a left ear, including the left ear helix.
FIG. 3R shows a right ear, including the right ear helix.
FIG. 3S shows a right-hand helix.
FIG. 3T shows a view of a mask, including the sign of the torsion of the space curve defined by the edge of the sealing membrane in different regions of the mask.
FIG. 3U shows a view of a plenum chamber 3200 showing a sagittal plane and a mid-contact plane.
Figures 3U, 3V, 3W, 3X:
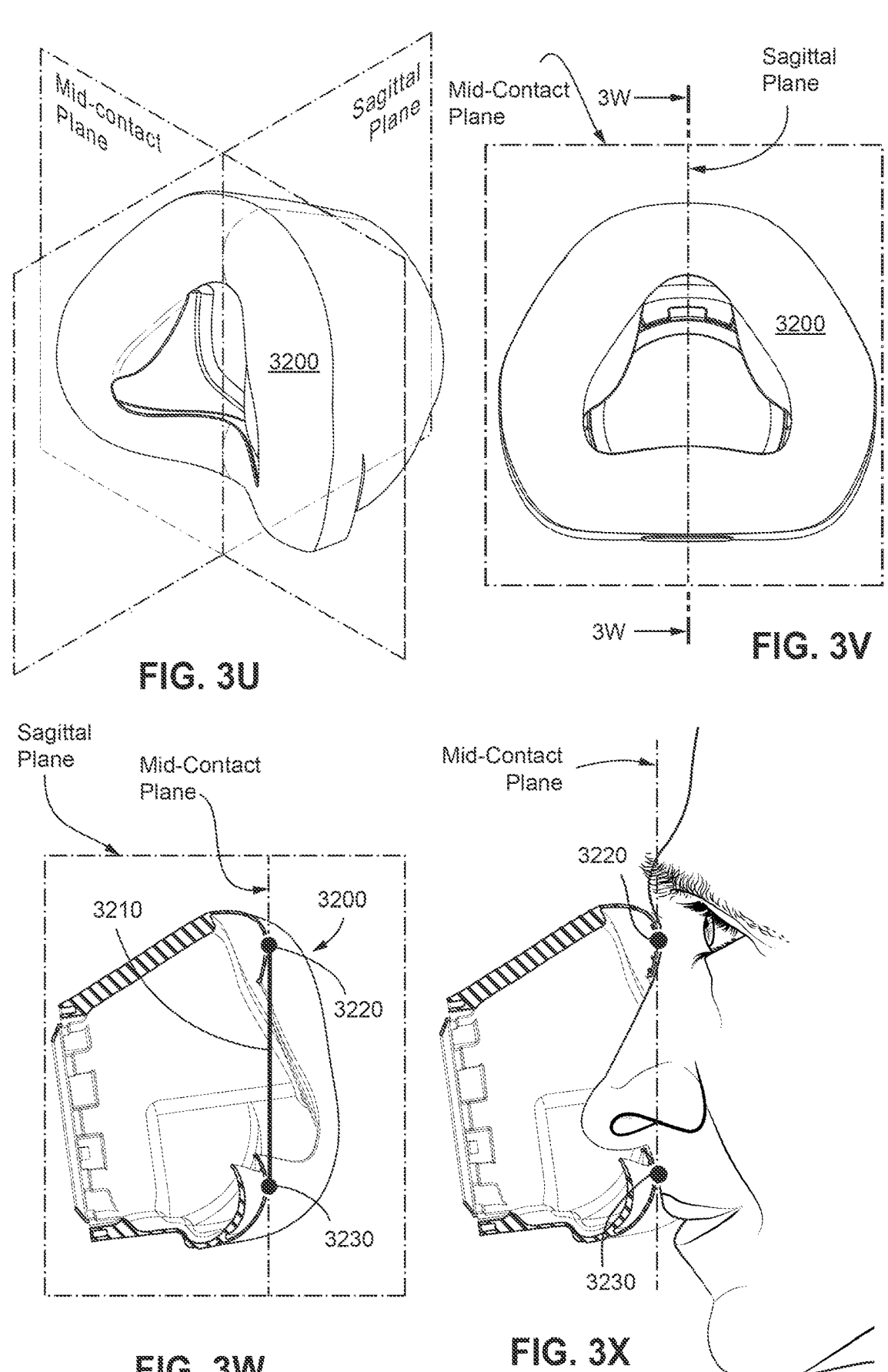

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 3Y:
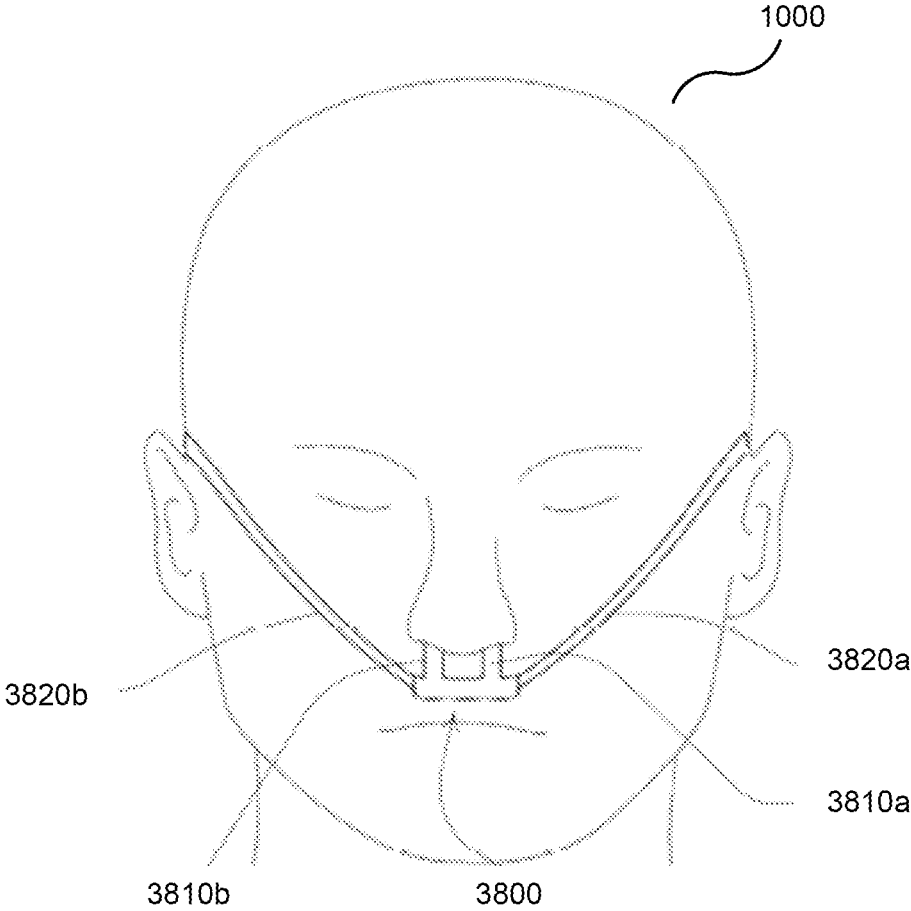

FIG. 3Y shows a patient interface in the form of a nasal cannula in accordance with one form of the present technology.

Figure 3Z:
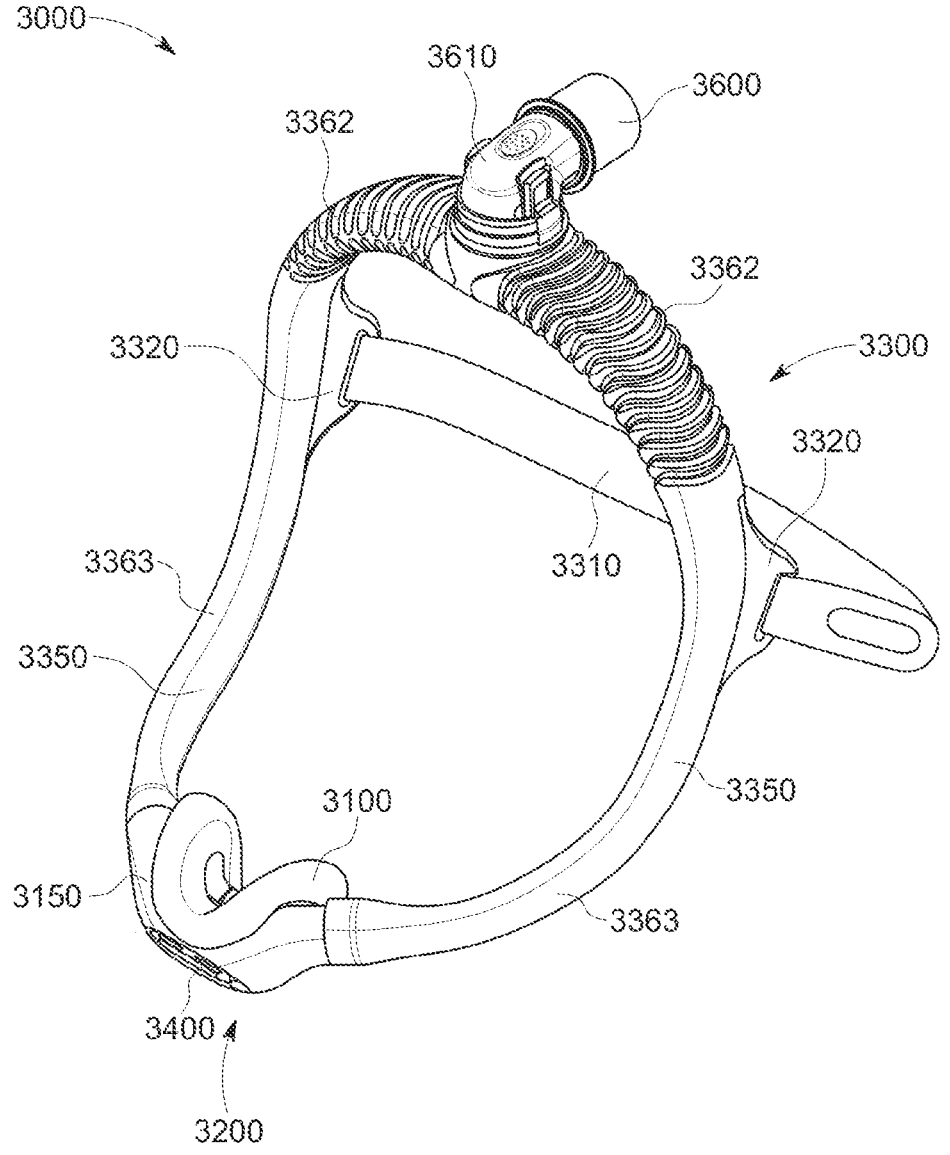

FIG. 3Z shows a patient interface having conduit headgear, in accordance with one form of the present technology.

4.4 RPT Device

Figure 4A:
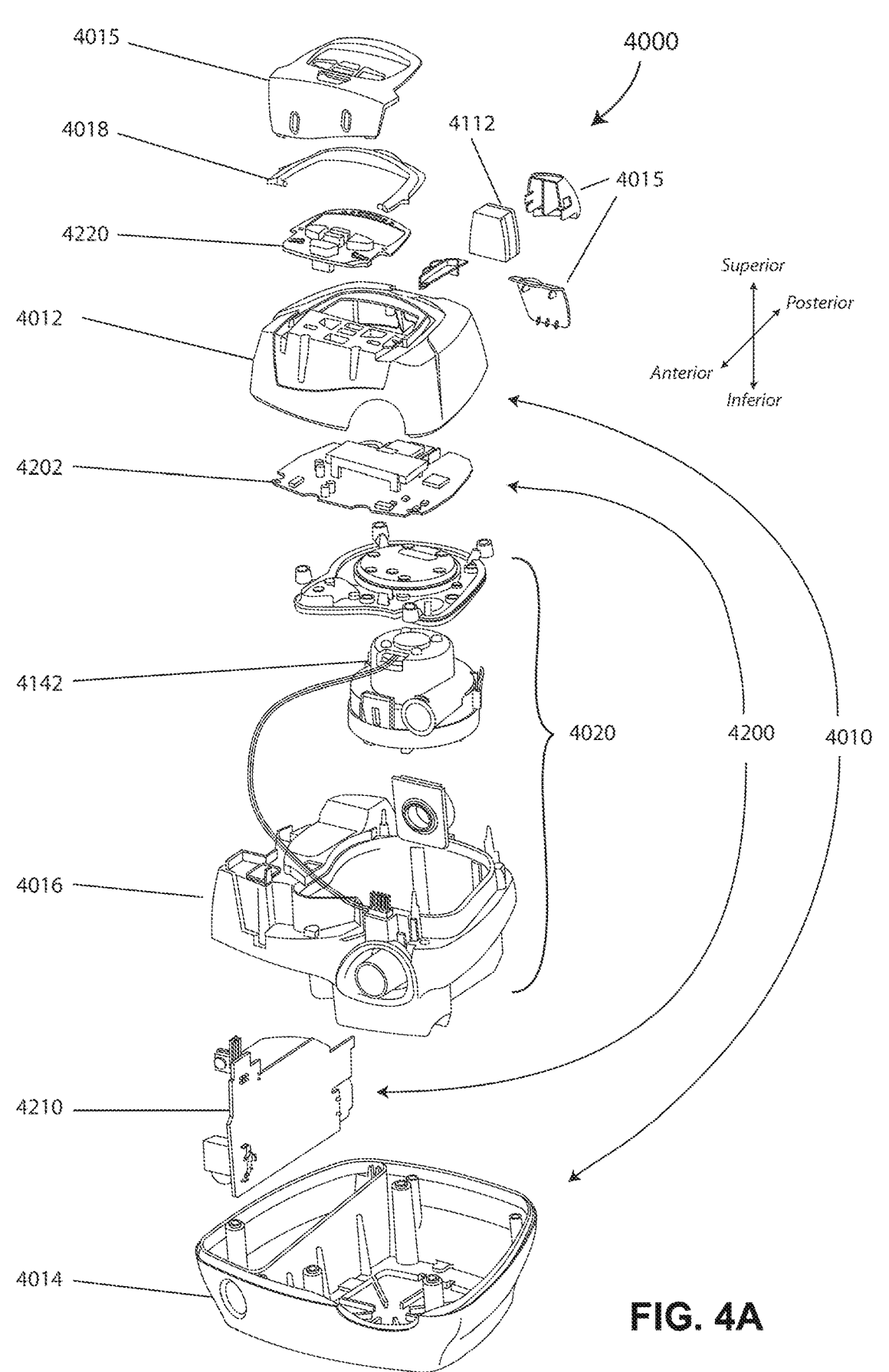

FIG. 4A shows an RPT device in accordance with one form of the present technology.

Figure 4B:
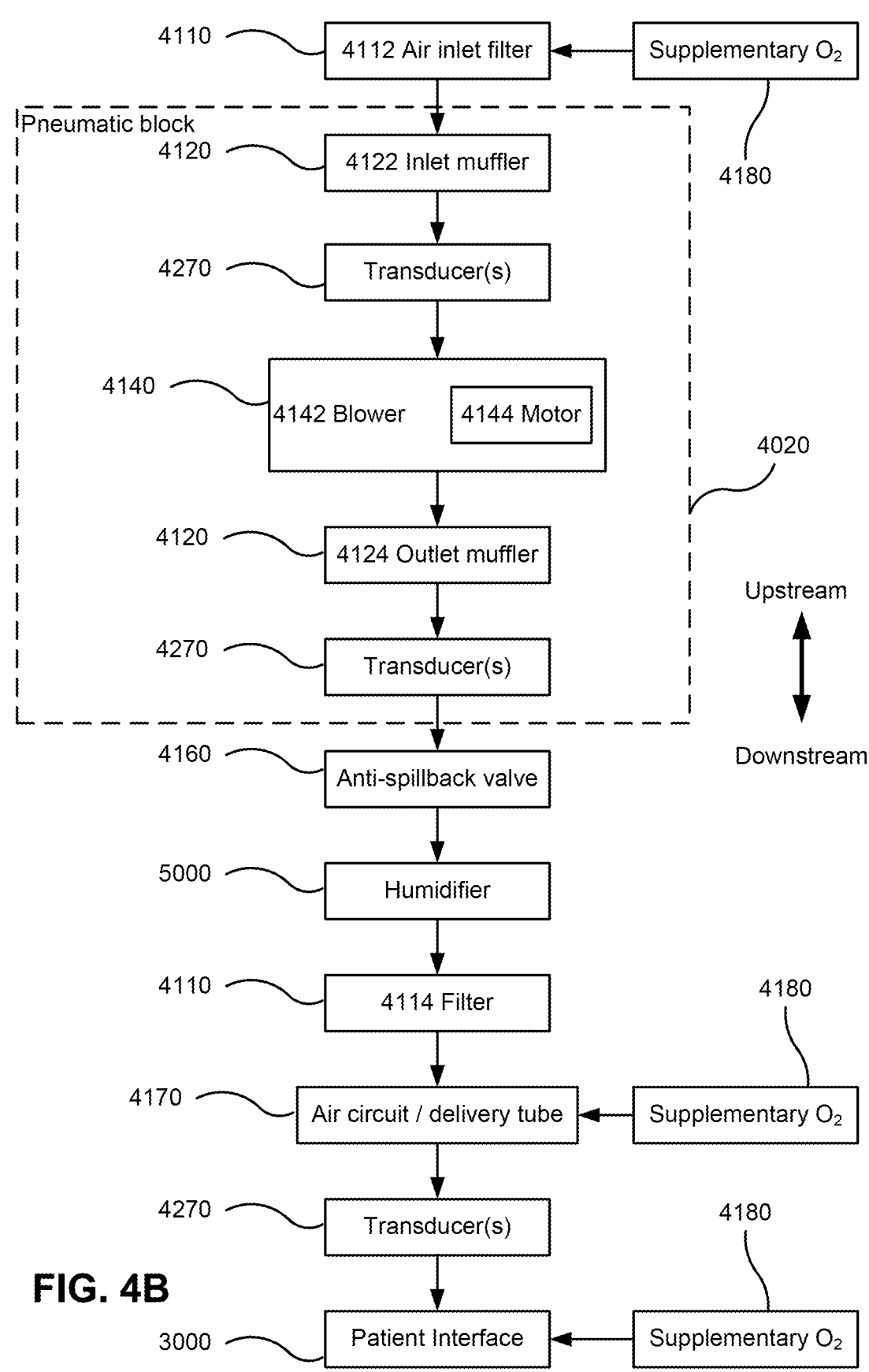

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
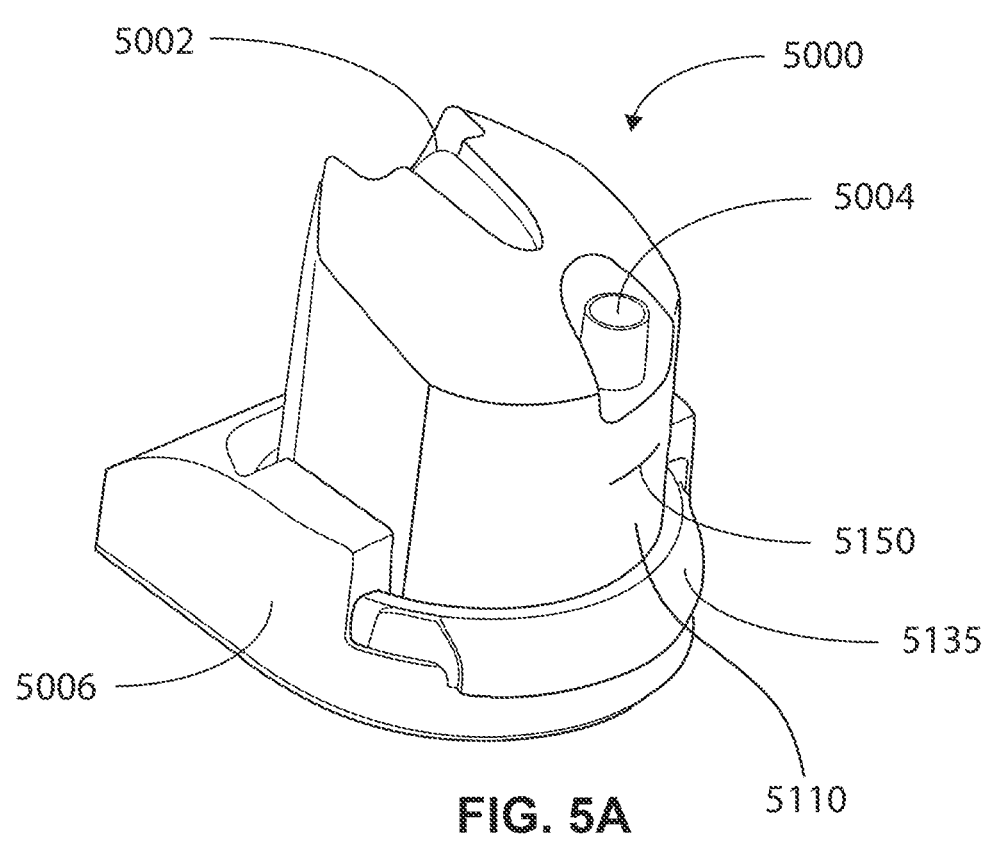

FIG. 5A shows an isometric view of a humidifier in accordance with one form of the present technology.

Figure 5B:
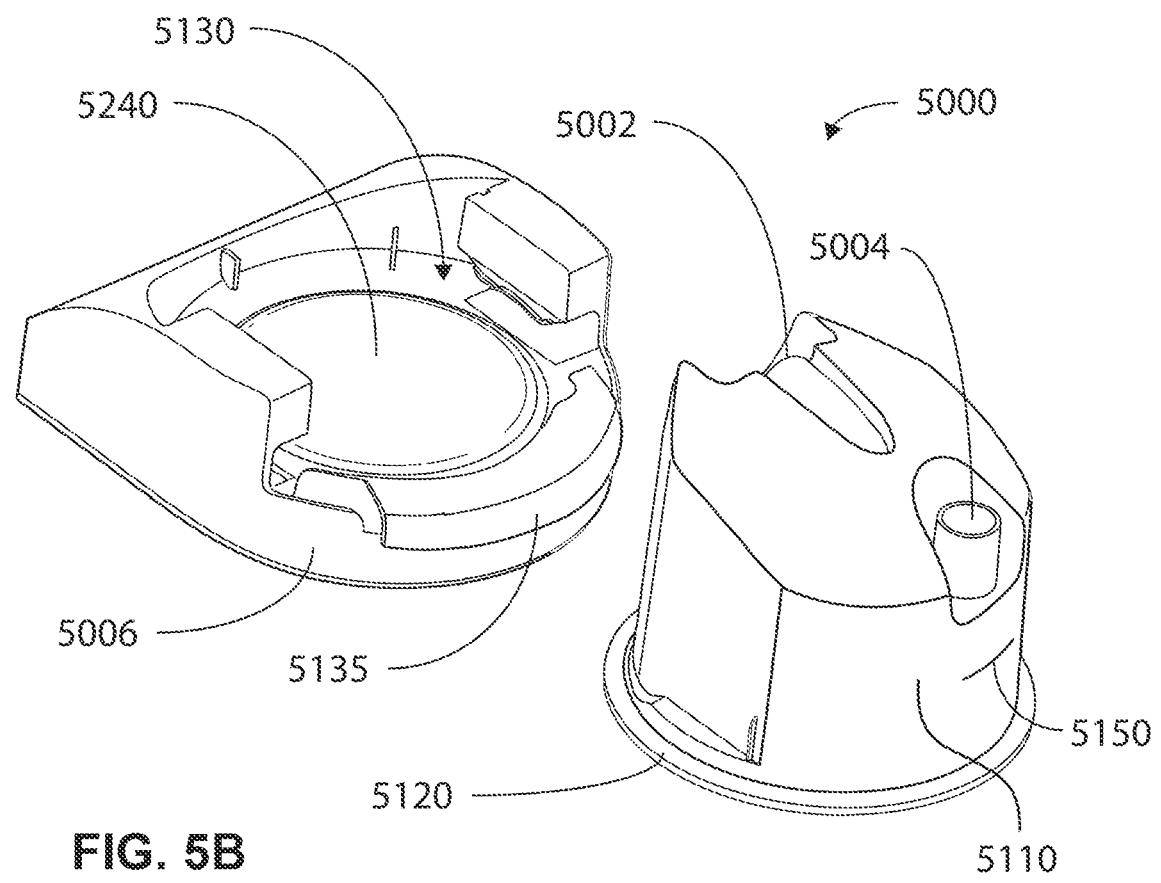

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
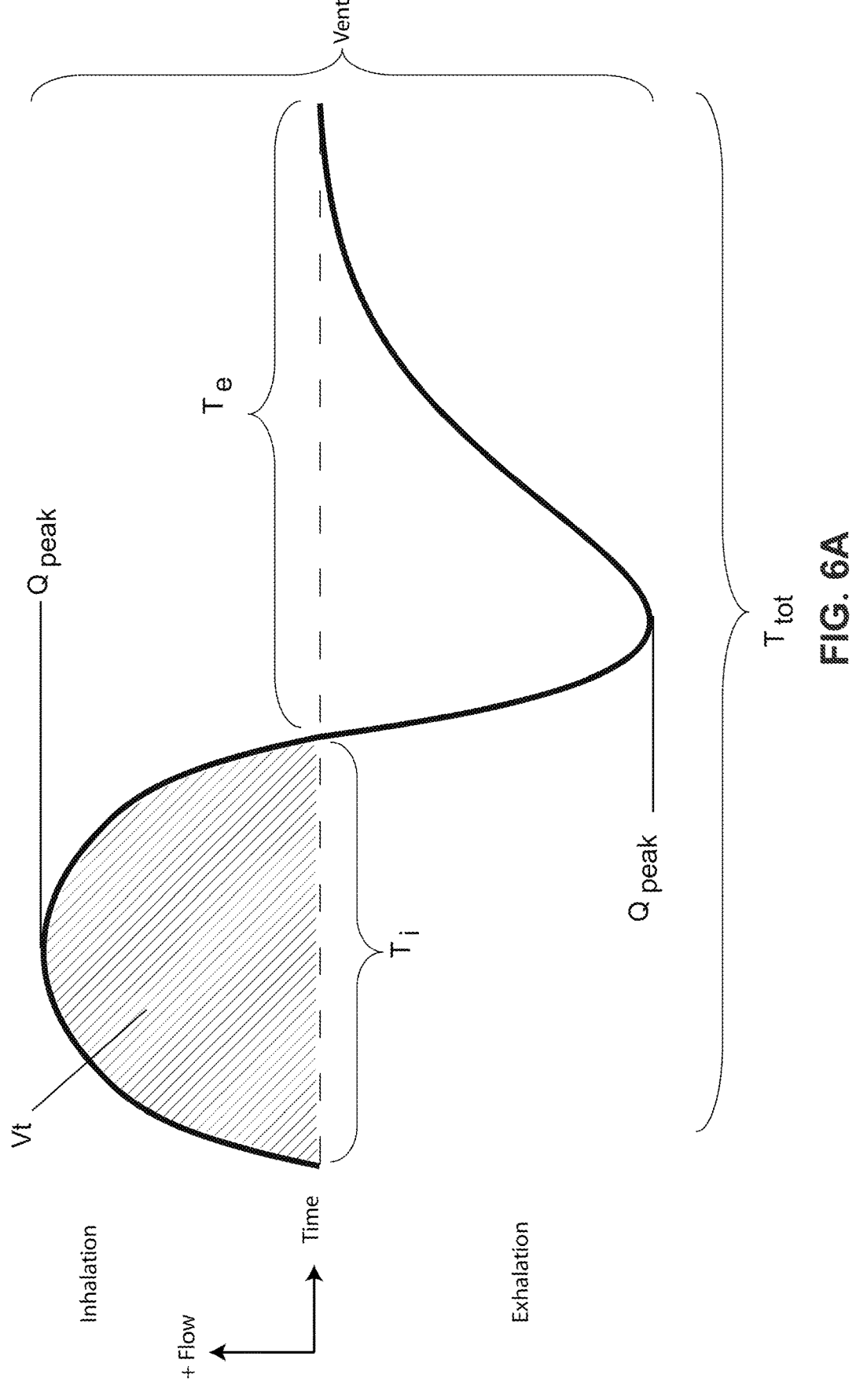

FIG. 6A shows a model typical breath waveform of a person while sleeping.

4.7 Screening, Diagnosis and Monitoring Systems

Figure 7A:
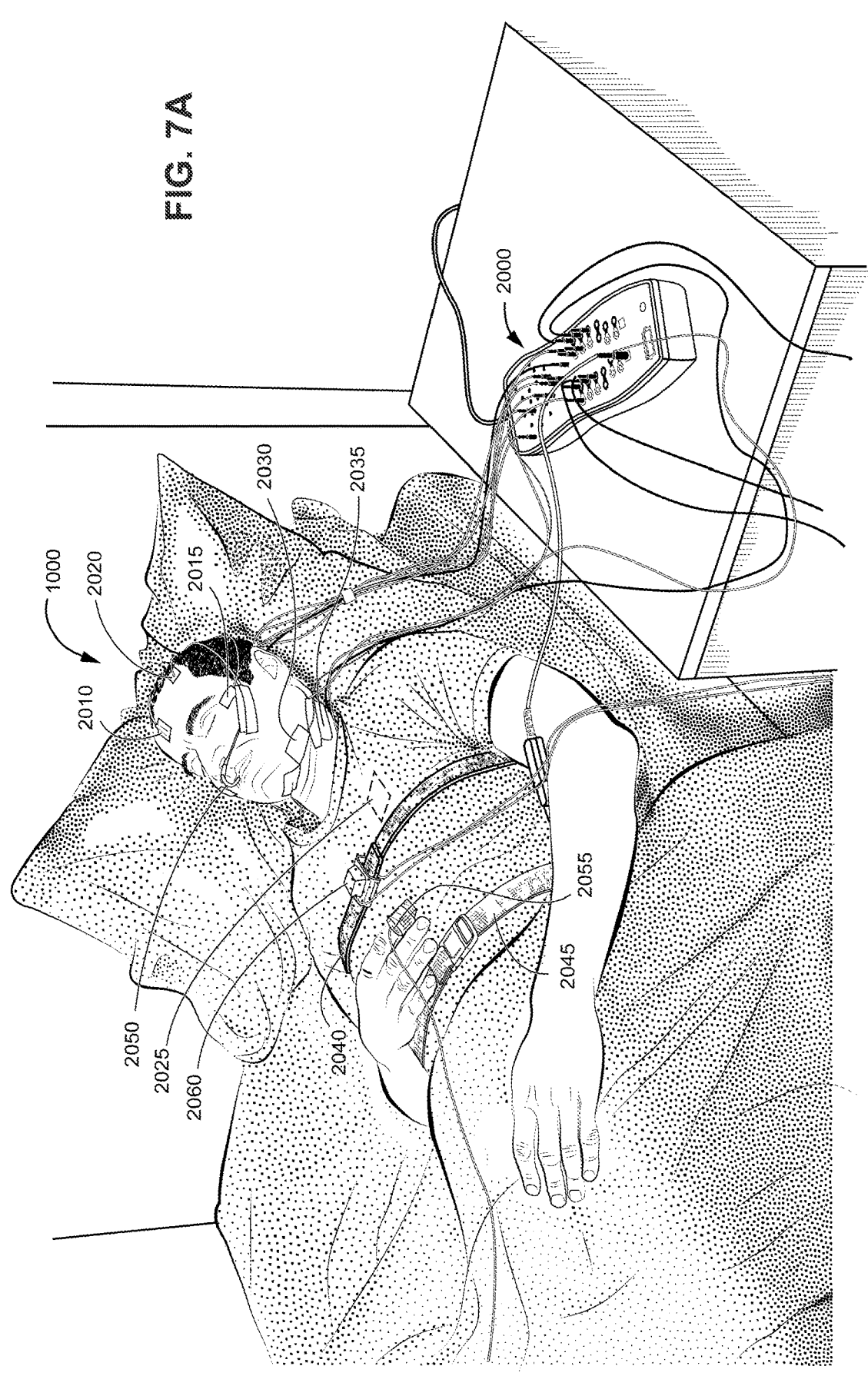

FIG. 7A shows a patient undergoing polysomnography (PSG). The patient is sleeping in a supine sleeping position.

Figure 7B:
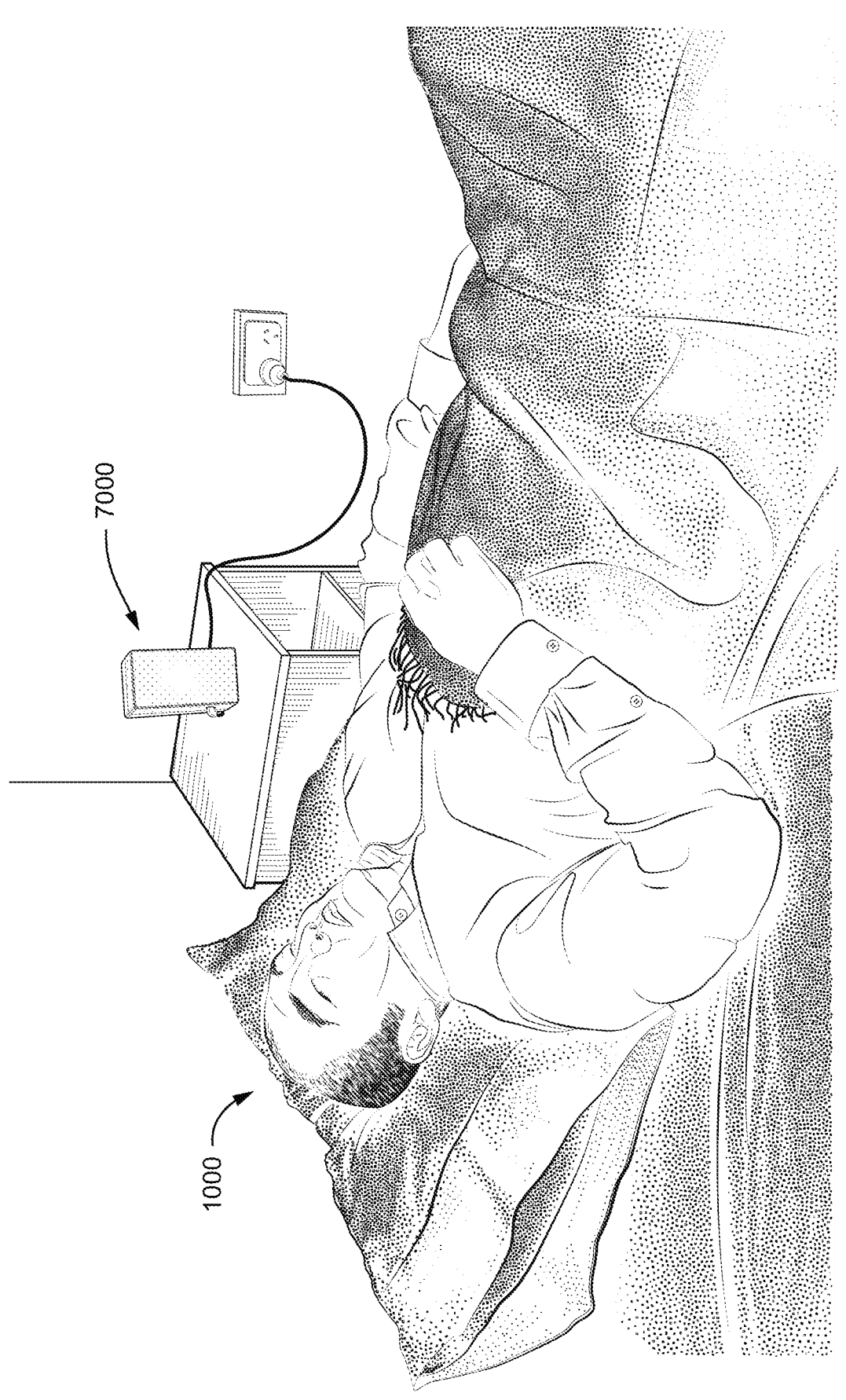

FIG. 7B shows a monitoring apparatus for monitoring the condition of a patient. The patient is sleeping in a supine sleeping position.

4.8 Vent Structure

Figure 8A:
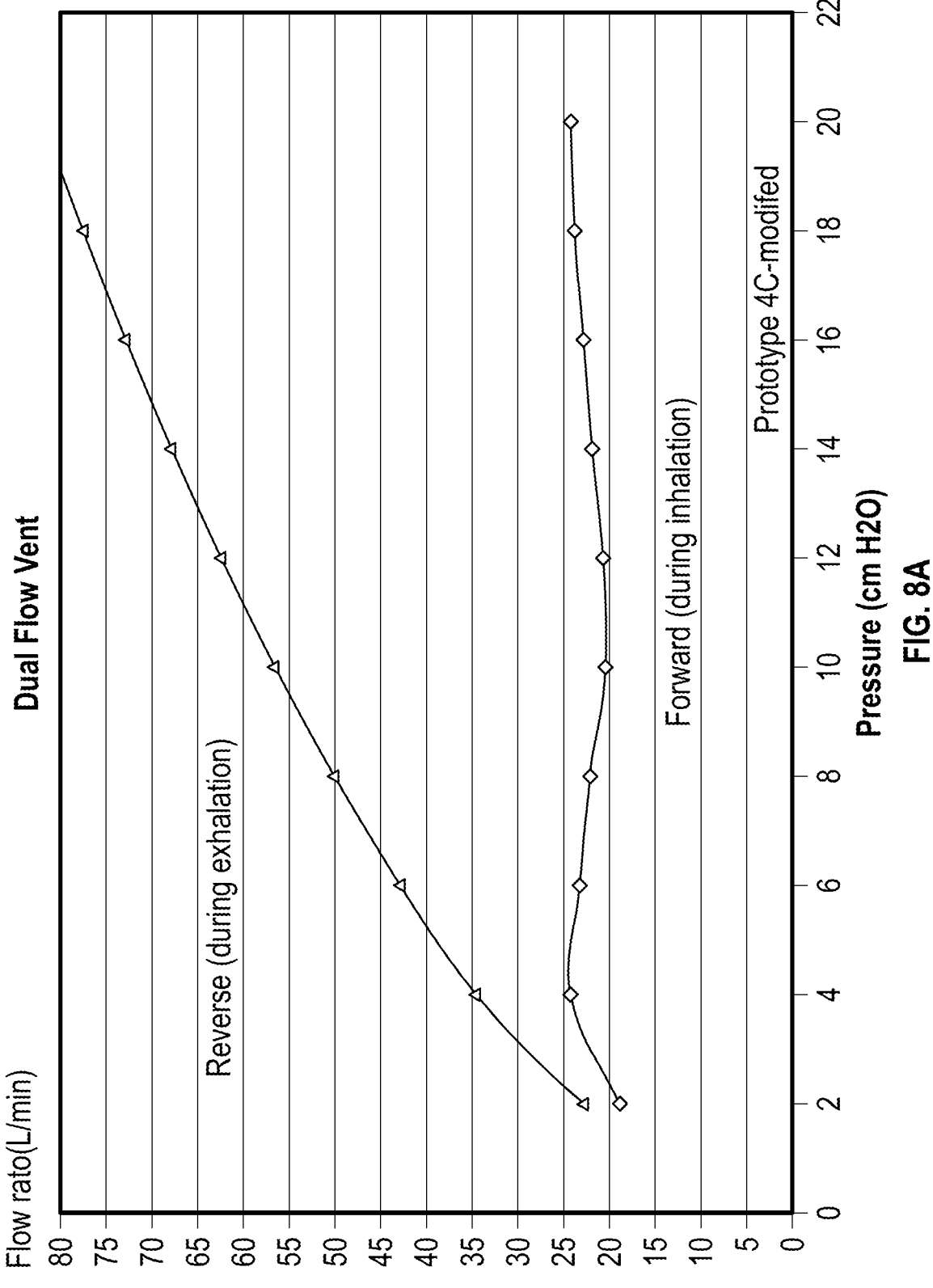

FIG. 8A shows graphs of vent flow rate against pressure during inhalation and exhalation according to an aspect of the technology.

Figure 8B:
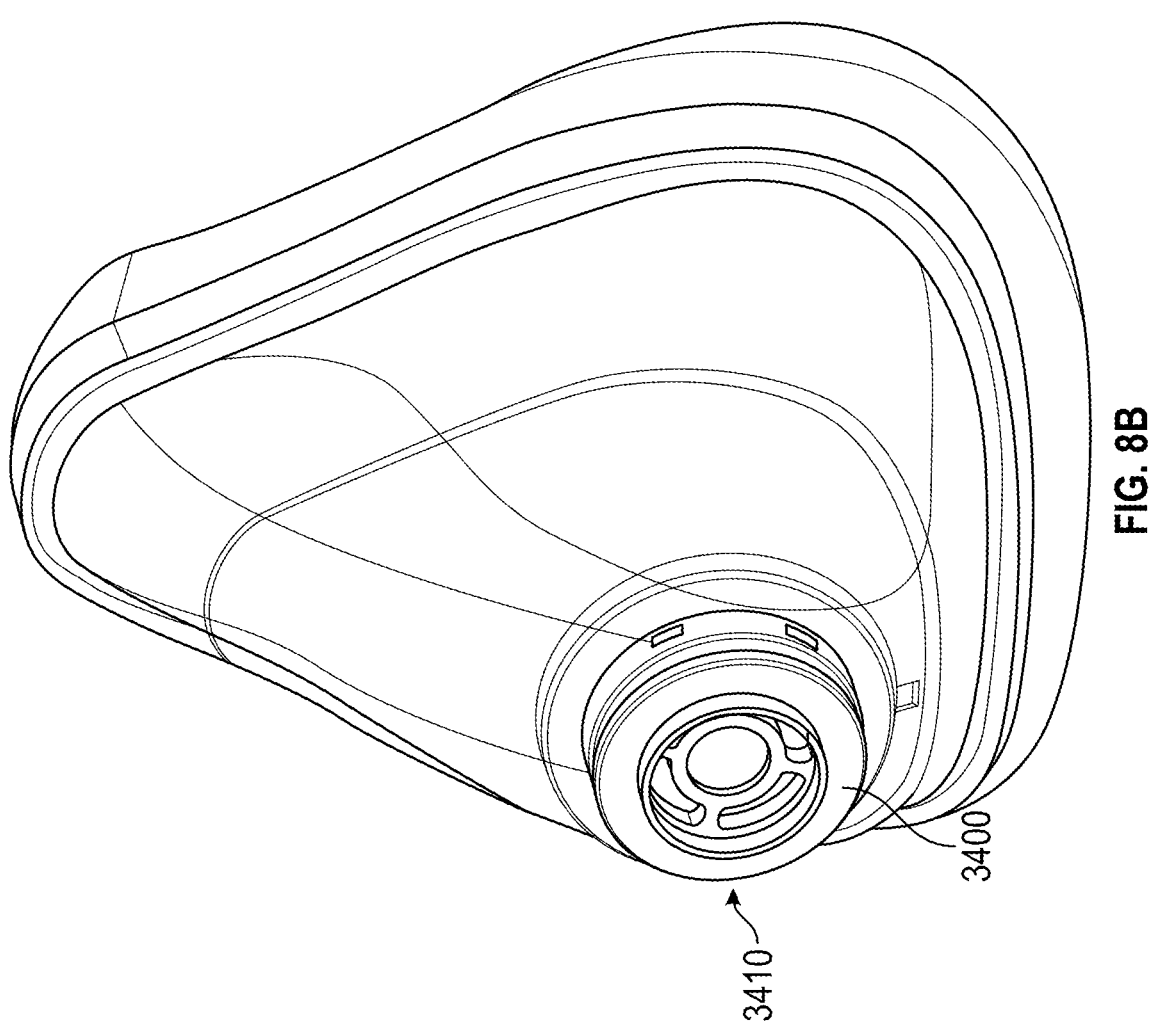

FIG. 8B shows a vent structure in accordance with an aspect of the present technology attached to part of a patient interface.

Figure 8C:
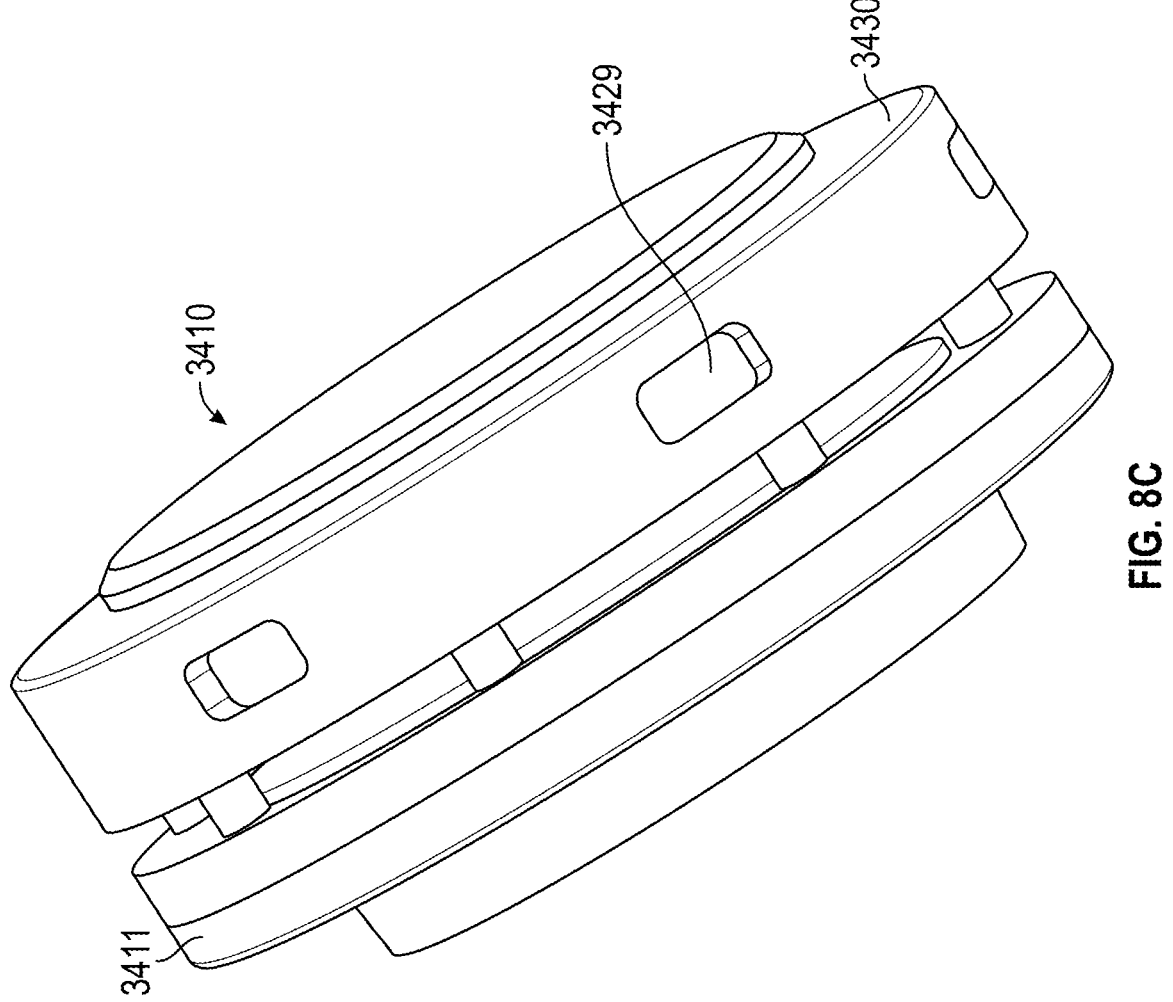

FIG. 8C shows a side perspective view of the vent structure of FIG. 8B.

Figure 8D:
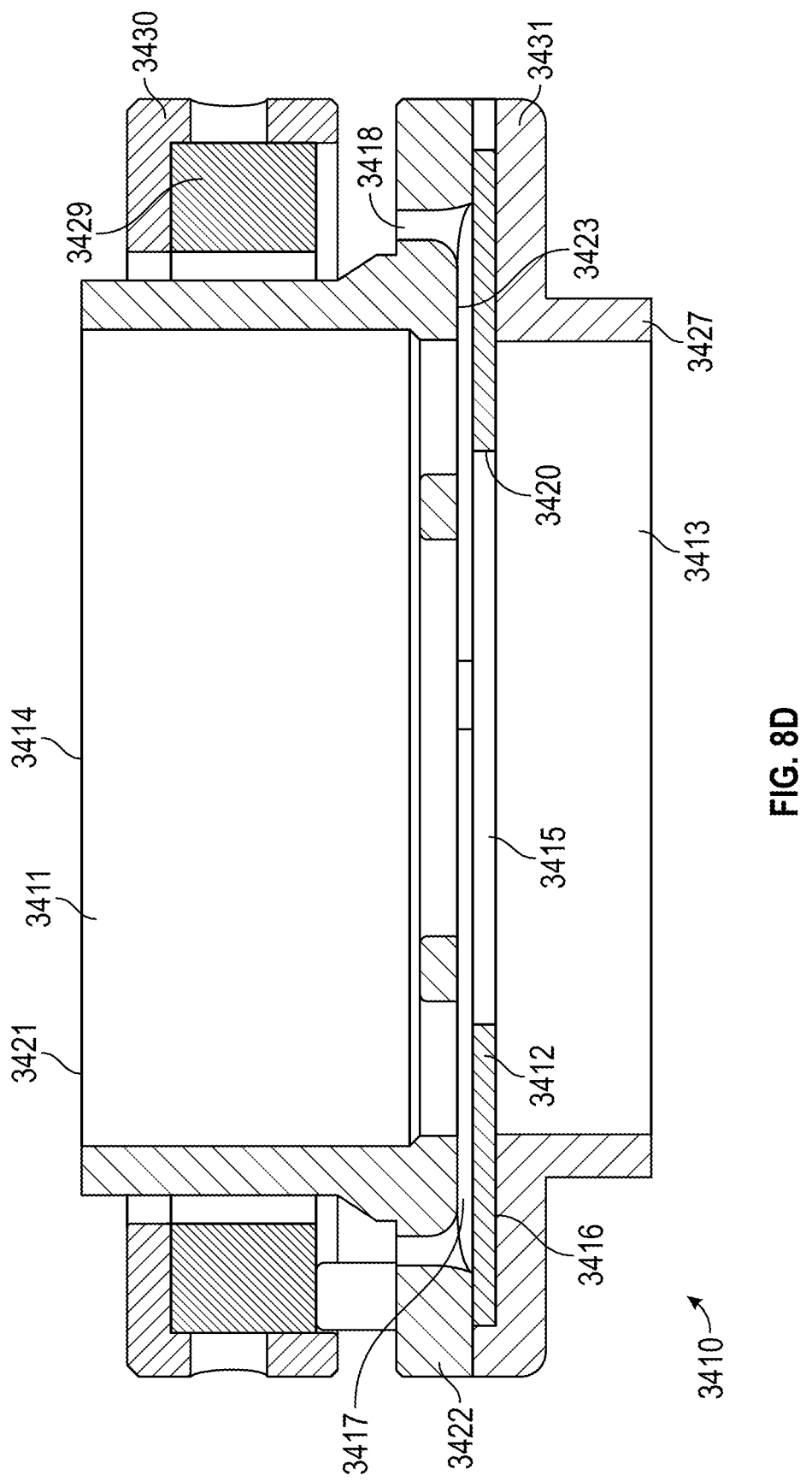

FIG. 8D shows a cross-sectional view of the vent structure of FIG. 8C.

Figure 8E:
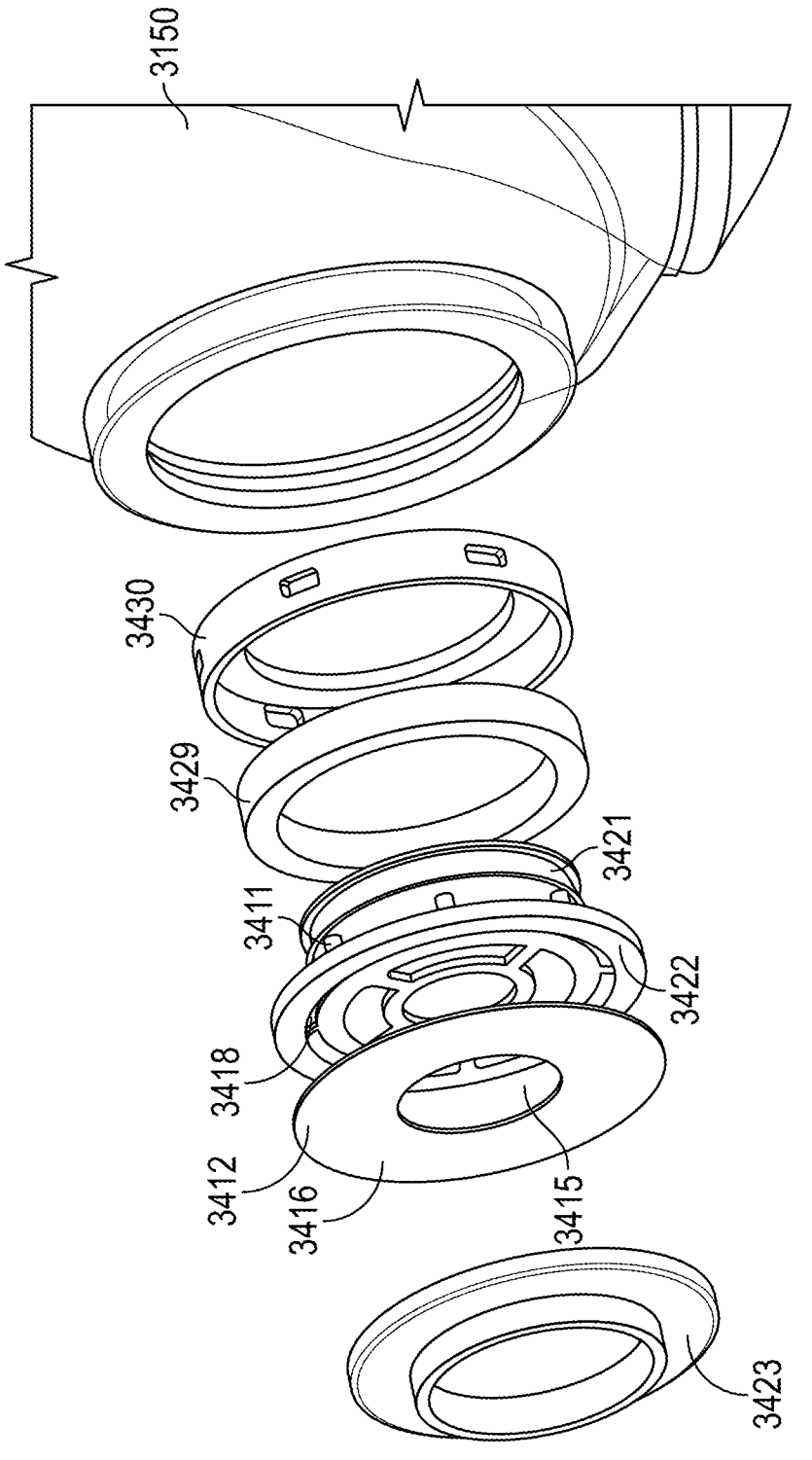

FIG. 8E shows an exploded view of a portion of the vent structure of FIG. 8B.

Figure 8F:
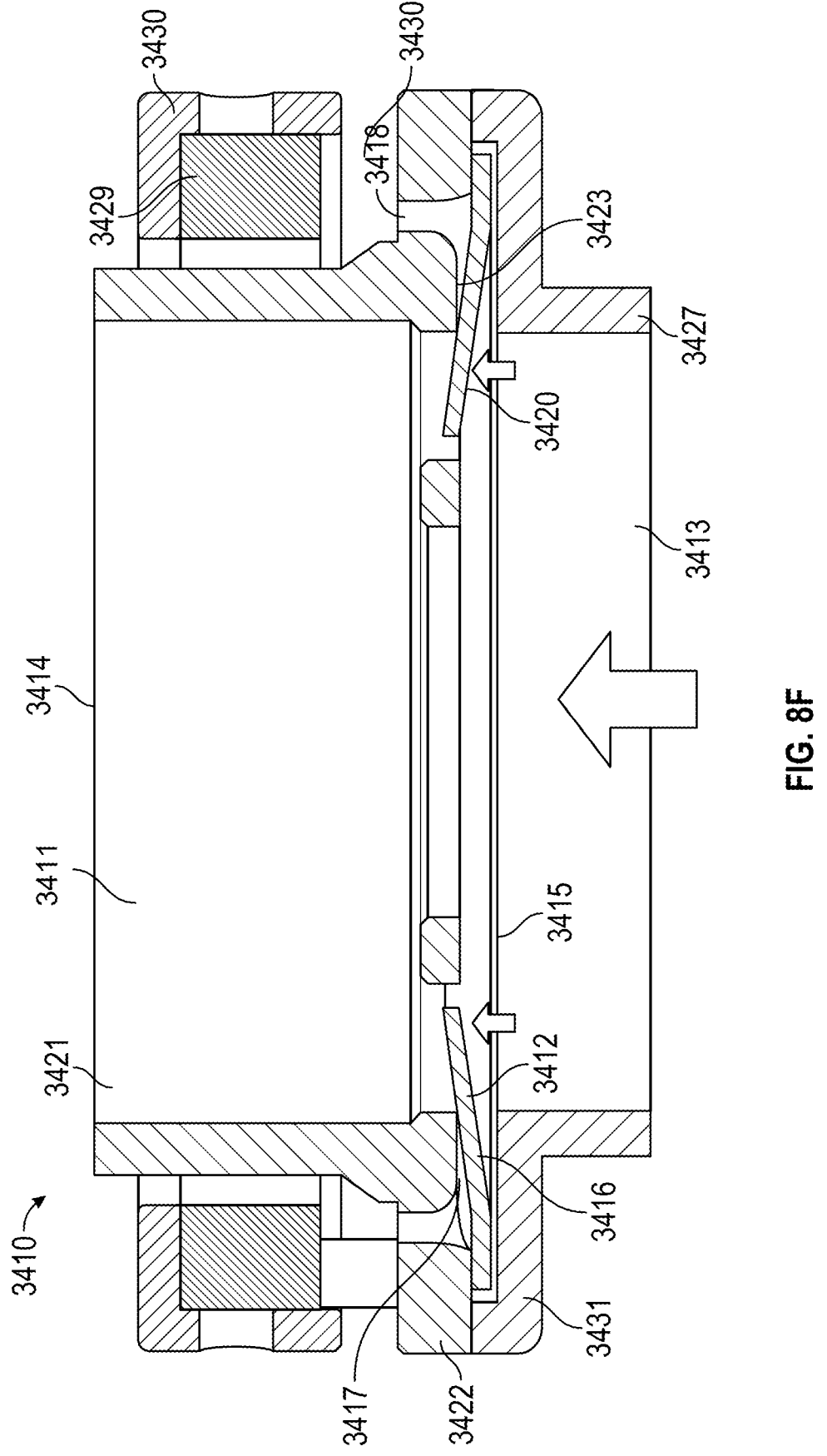

FIG. 8F shows a cross-sectional view of the vent structure of FIG. 8D with the membrane in a position deflected in a first direction.

Figure 8G:
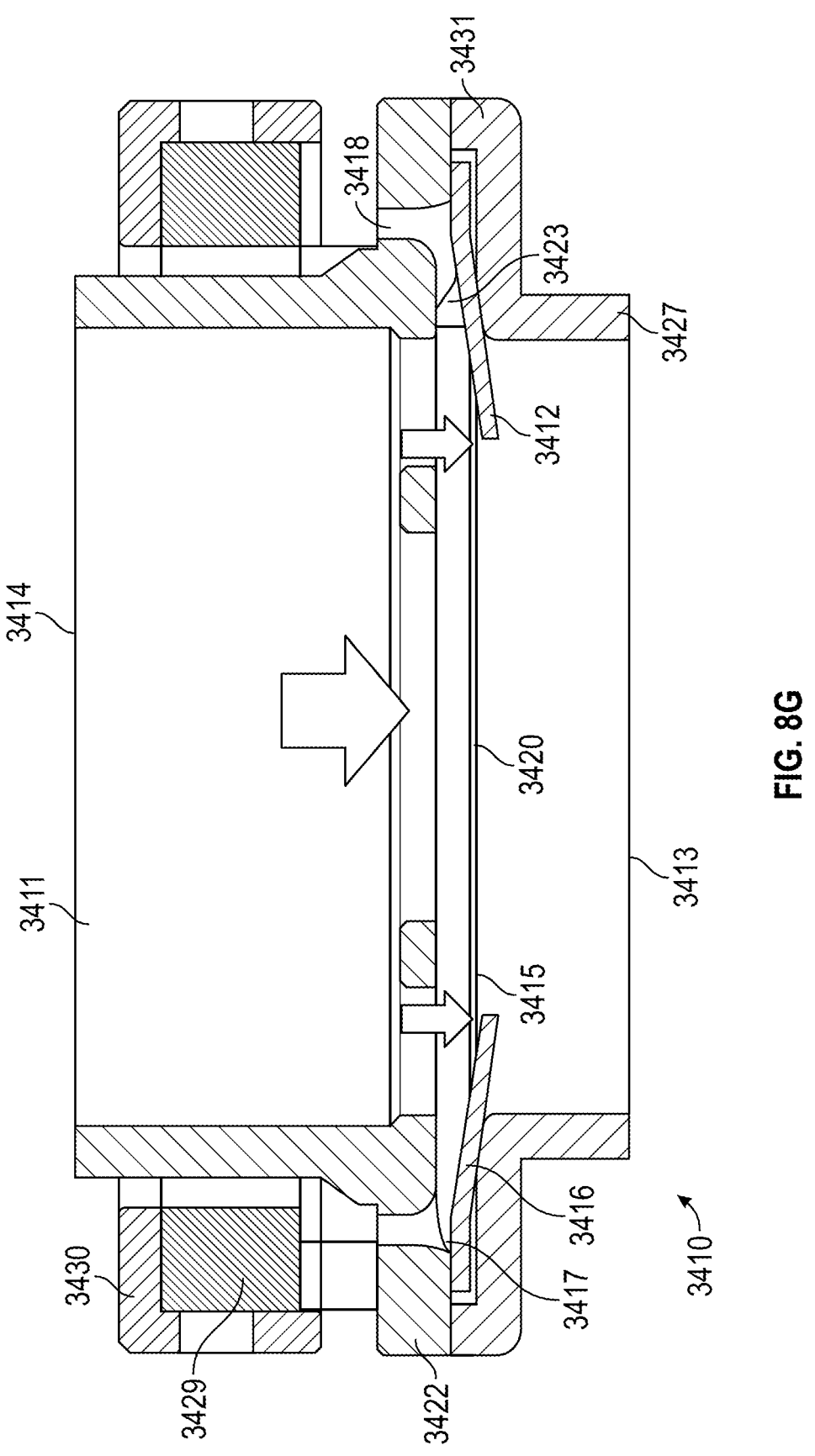

FIG. 8G shows a cross-sectional view of the vent structure of FIG. 8D with the membrane deflected in a second direction.

Figures 8H, 8I:
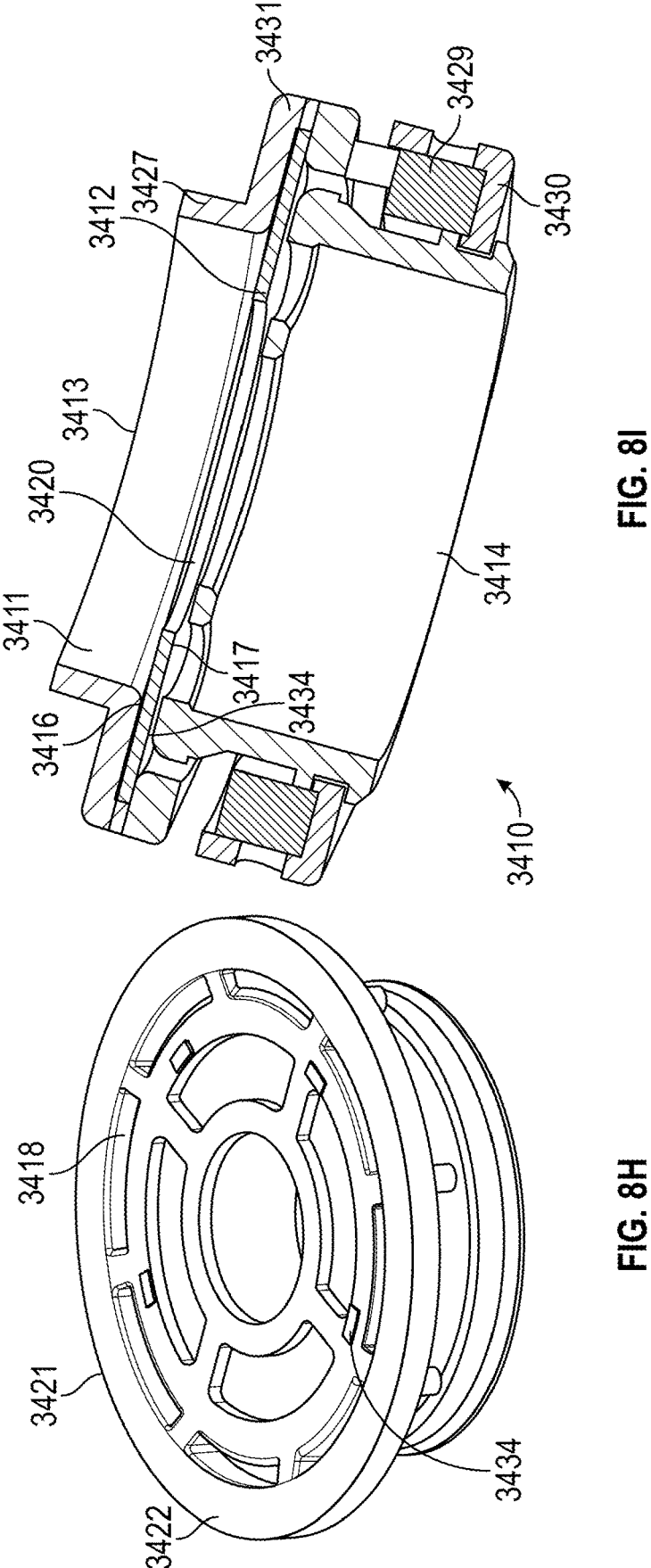

FIG. 8H shows a perspective view of a portion of the vent structure of FIG. 8B.

FIG. 8I shows a cross-sectional view of the vent structure of FIG. 8B.

Figures 8J, 8K:
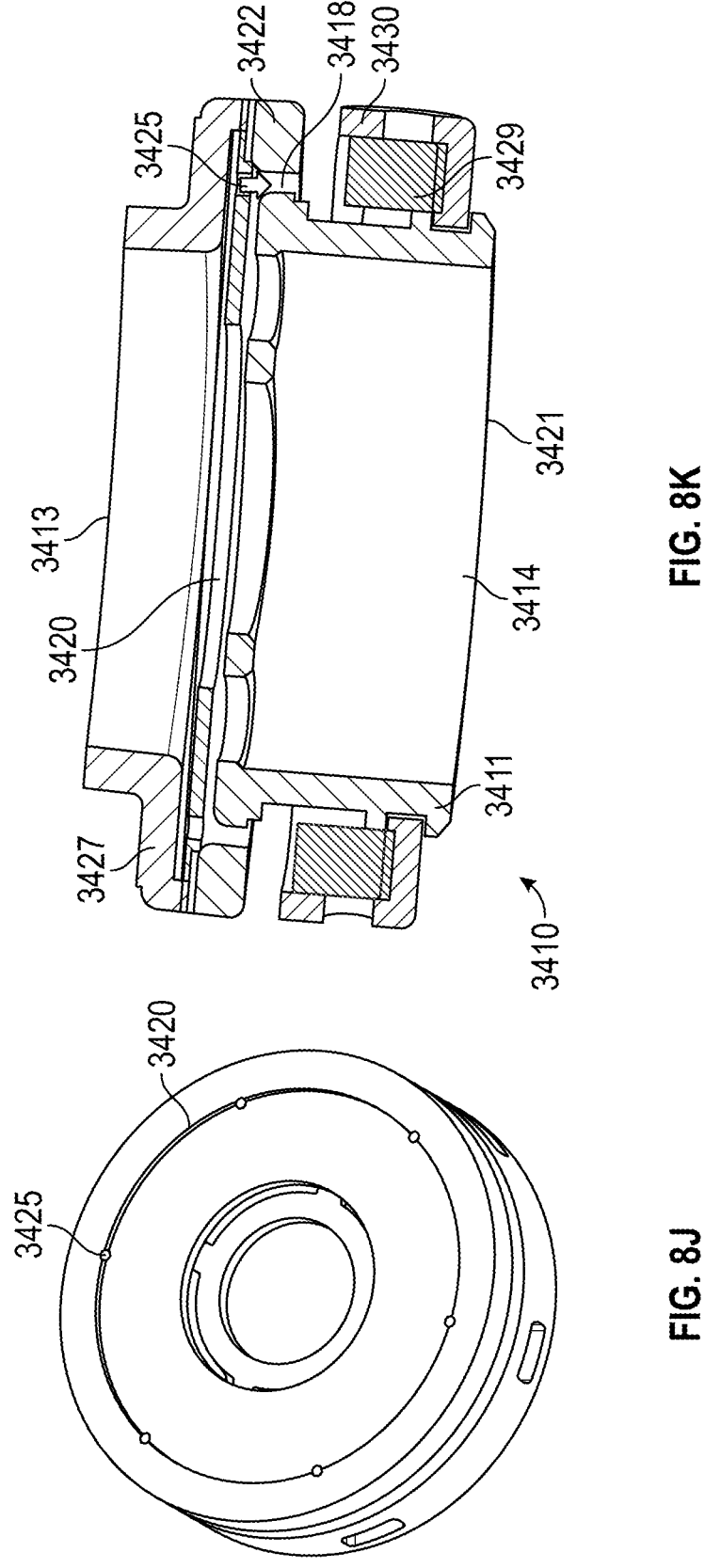

FIG. 8J shows a front perspective view of a portion of a vent structure in accordance with an aspect of the present technology.

FIG. 8K shows a side cross-sectional view of the vent structure of FIG. 8J

Figure 8L:
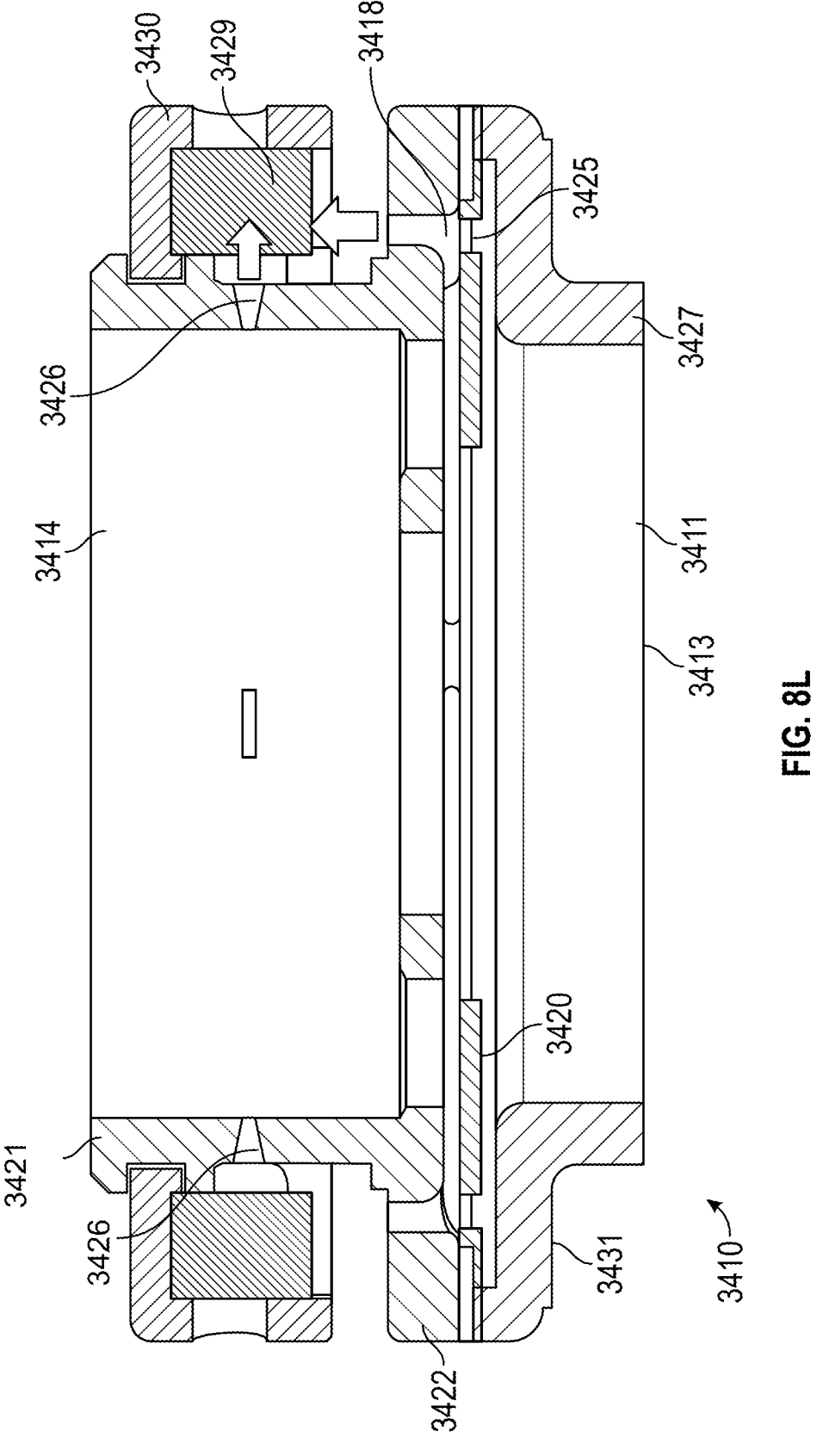

FIG. 8L shows a cross-sectional view of the vent structure of FIG. 8B.

Figure 8M:
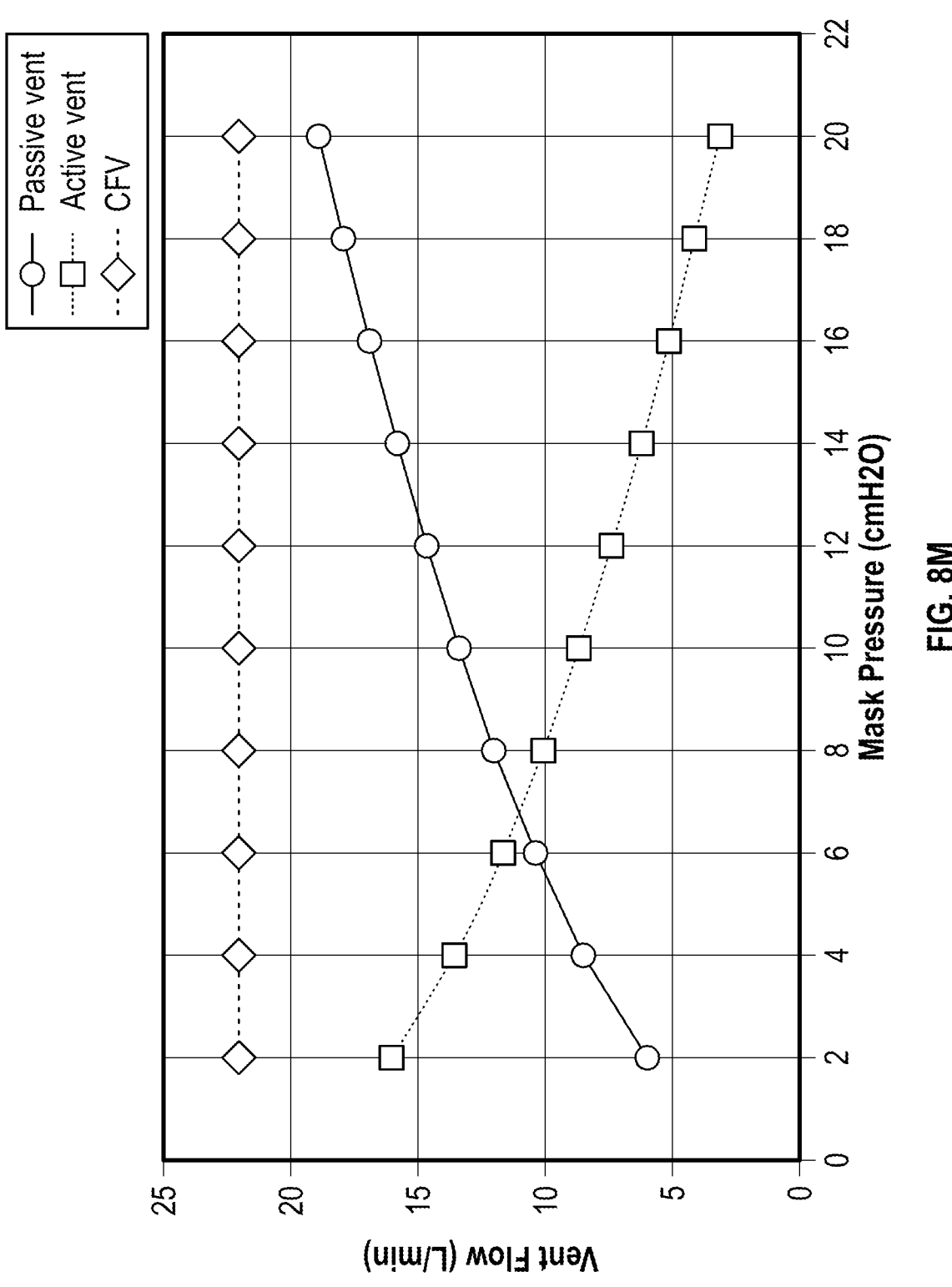

FIG. 8M shows graphs of vent flow against pressure in accordance with the vent structure of FIG. 8B.

Figure 8N:
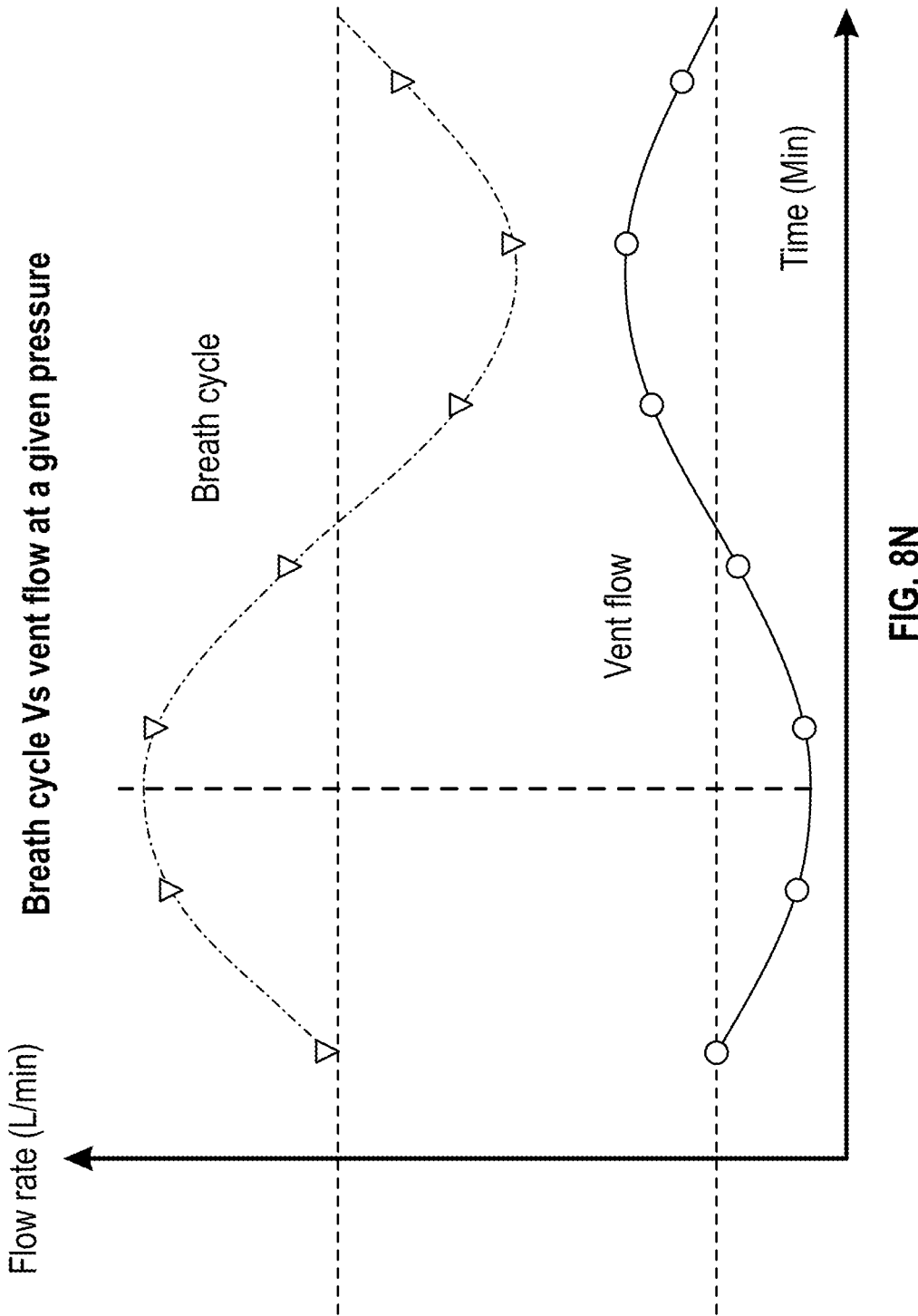
Figure 80:
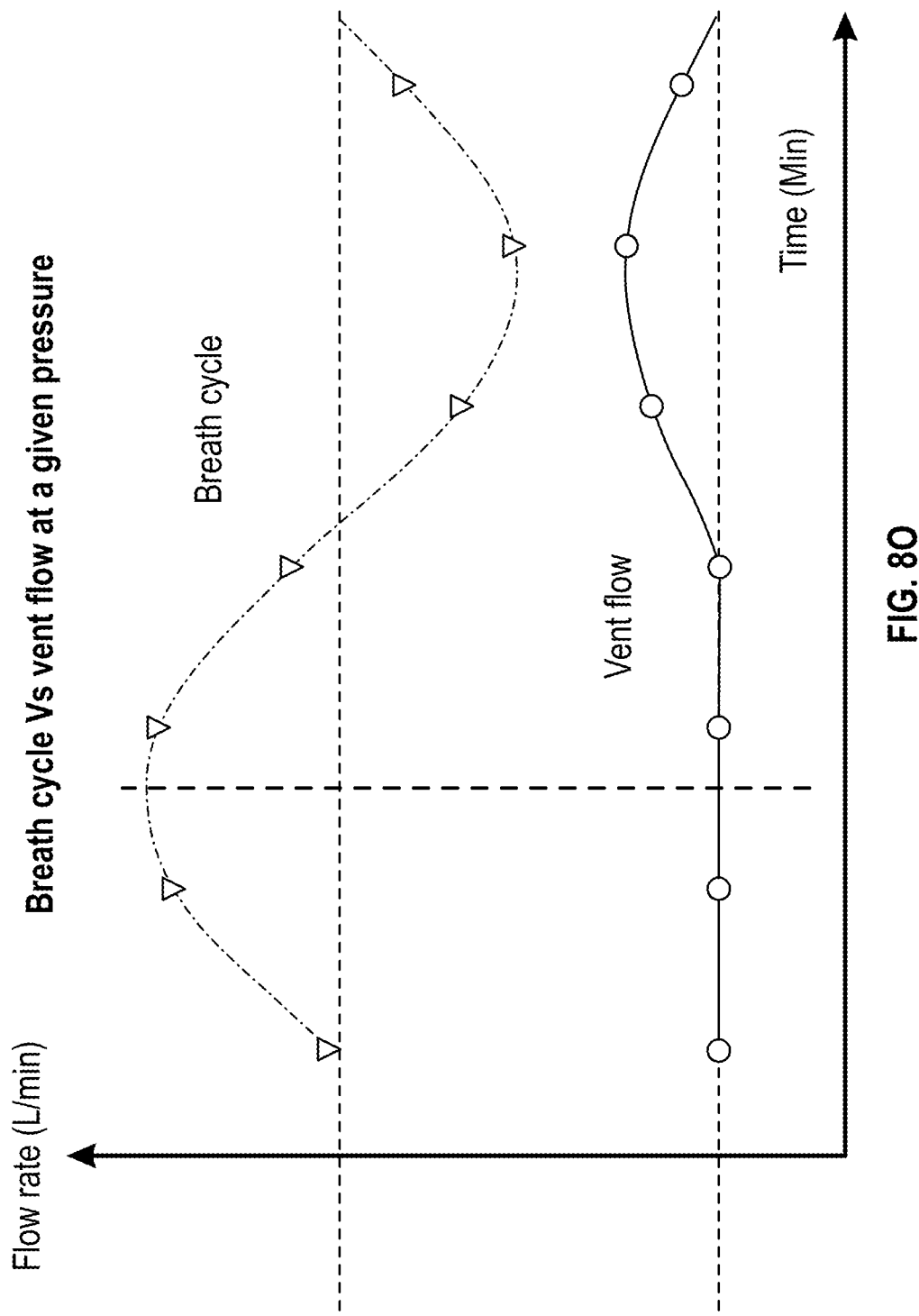

FIG. 8N shows a graph of breath cycle of a patient and vent flow against pressures for the vent structure of FIG. 8B.

FIG. 8O shows a graph of breath cycle of a patient and vent flow against pressure for a vent structure according to another aspect of the technology.

Figure 8P:
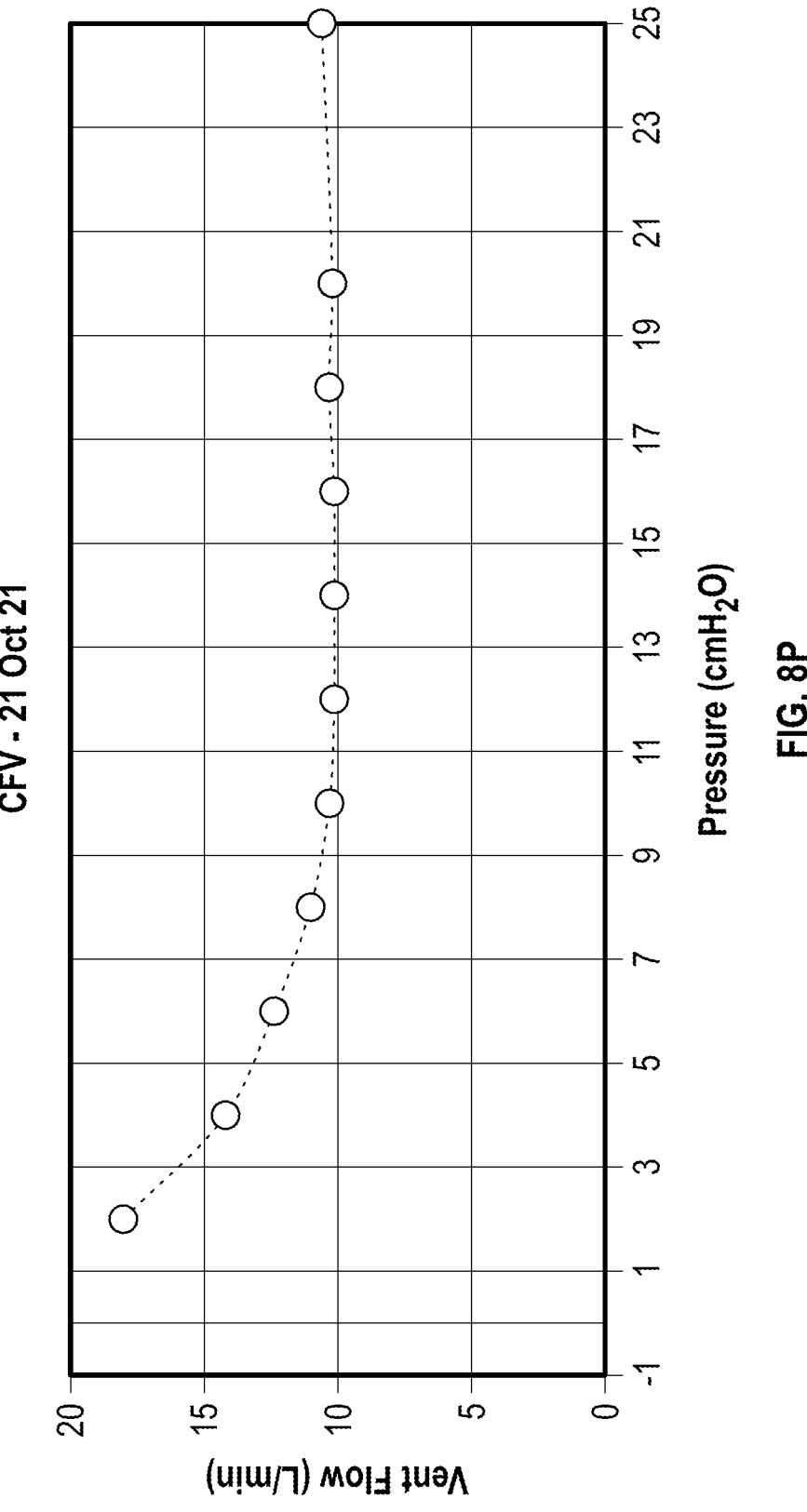

FIG. 8P shows a graph of vent flow versus pressure for a vent structure according to another aspect of the technology.

Figure 8Q:
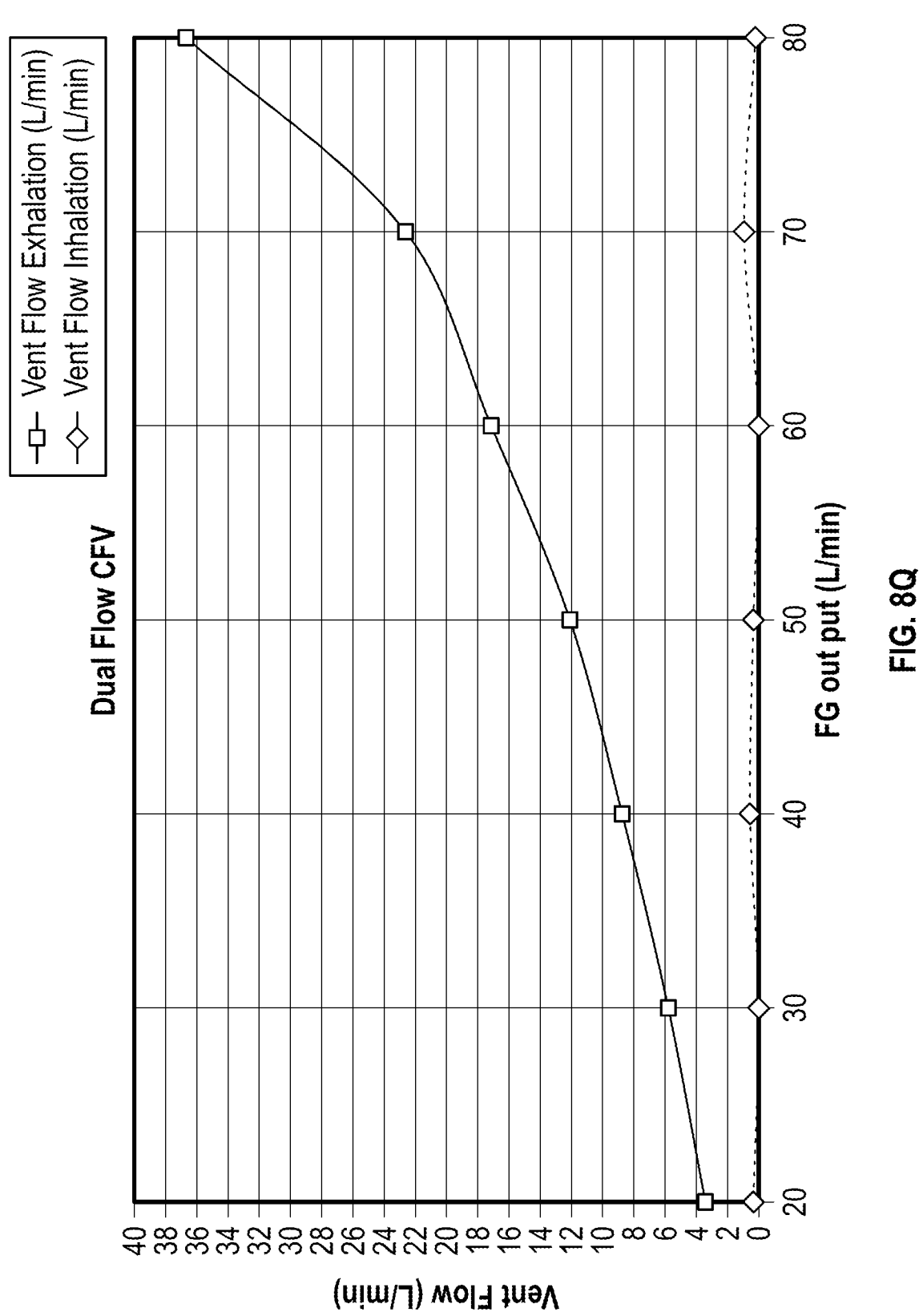

FIG. 8Q shows a graph of vent flow versus RPT device output for a vent structure according to another aspect of the technology.

Figure 9A:
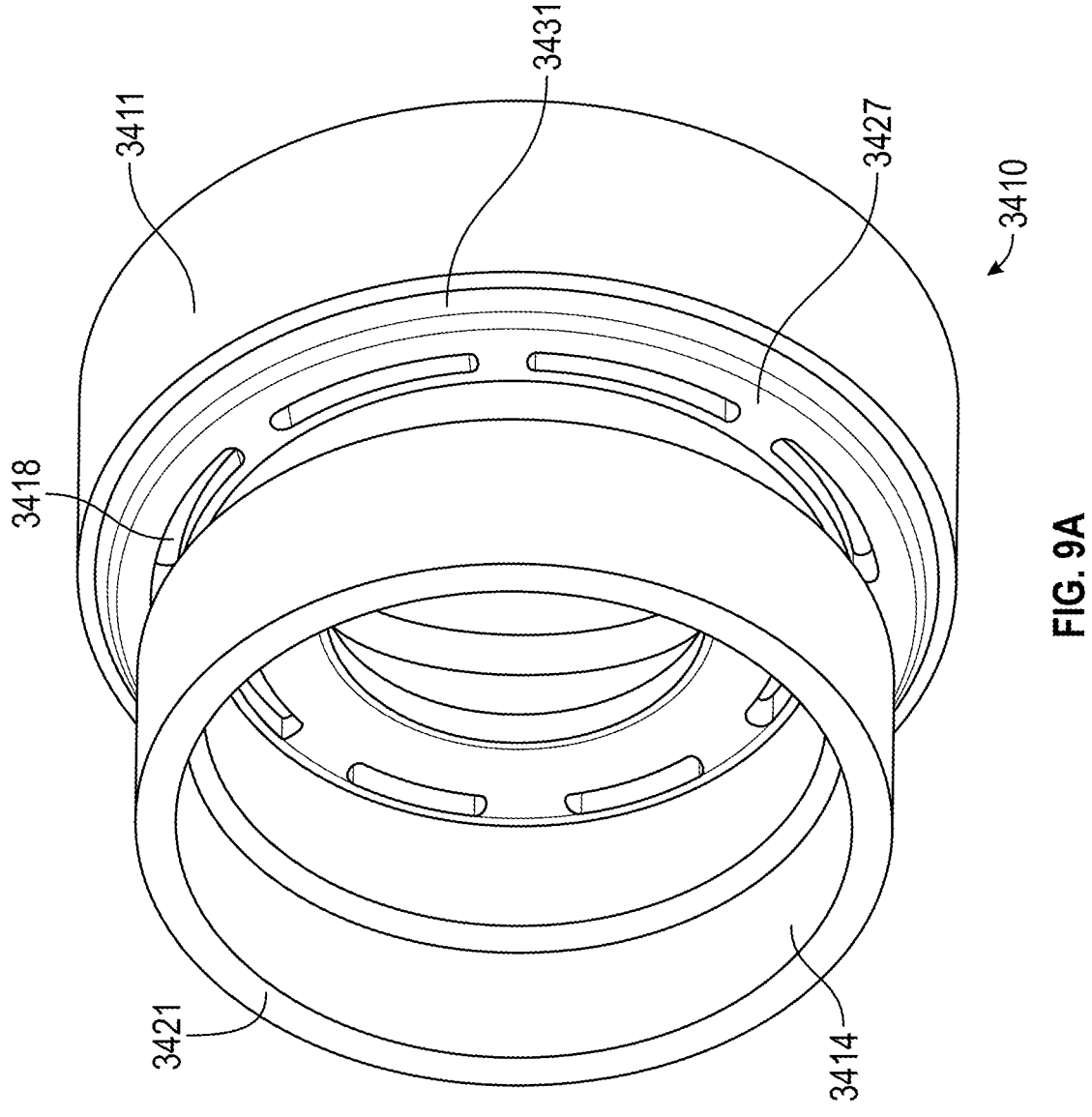

FIG. 9A shows a perspective view of a vent structure according to another aspect of the technology.

Figure 9B:
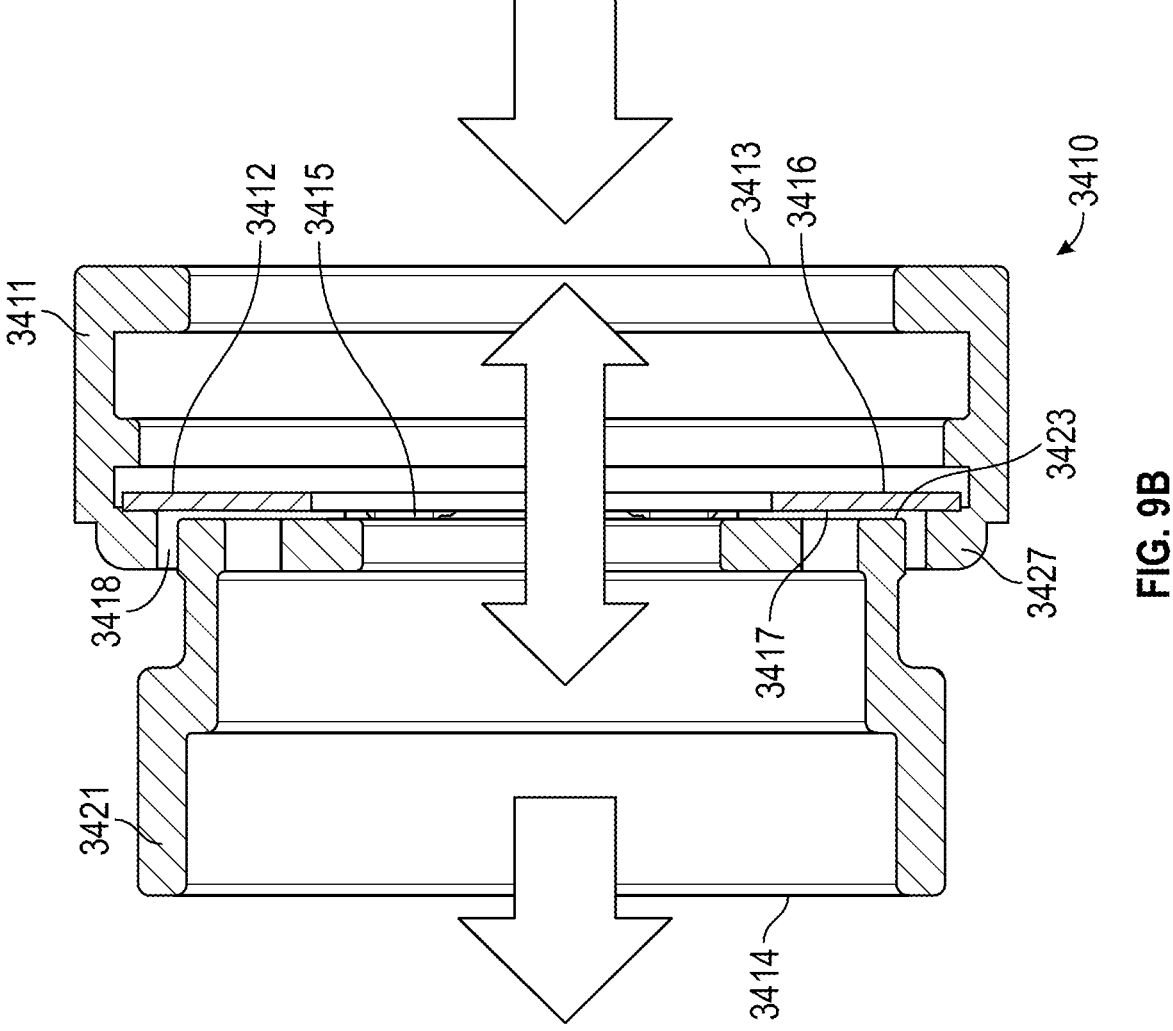

FIG. 9B shows a cross-sectional side view of the vent structure of FIG. 9A.

Figure 9C:
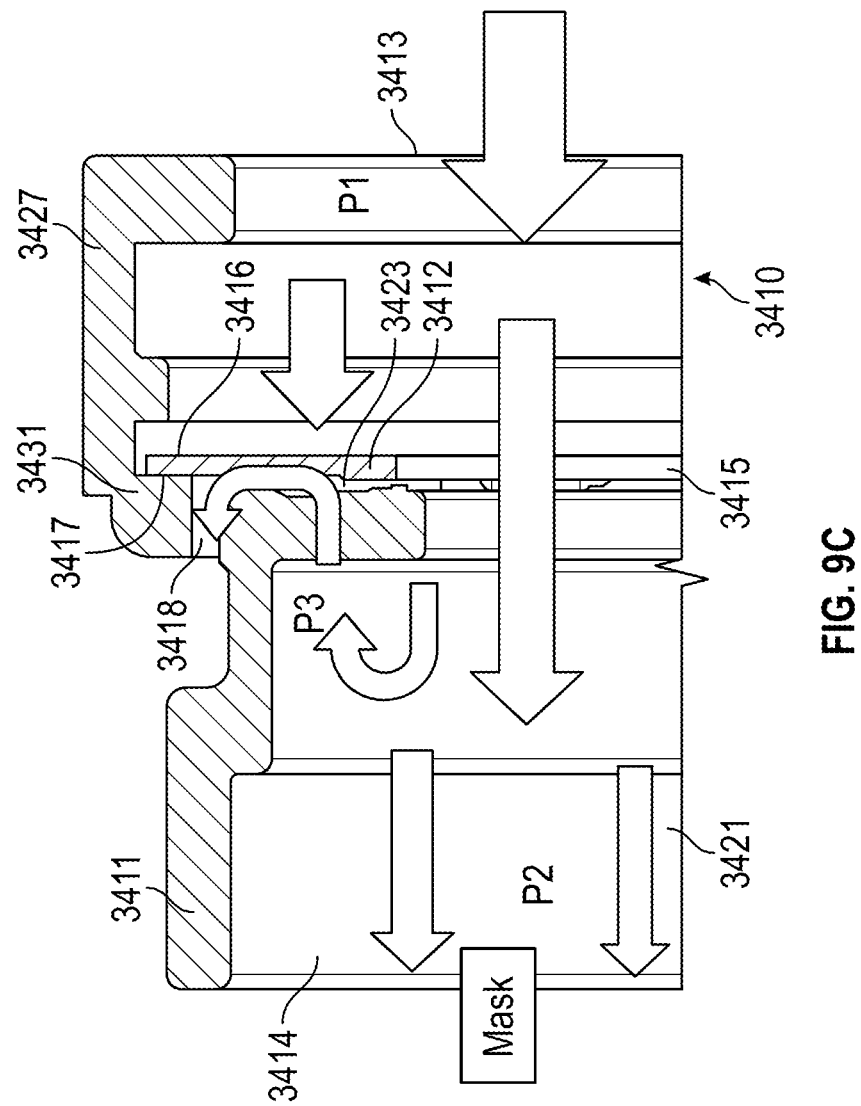

FIG. 9C shows an enlarged region of the vent structure of FIG. 9B showing the flow pattern during inhalation of a patient in one form of the technology.

Figure 9D:
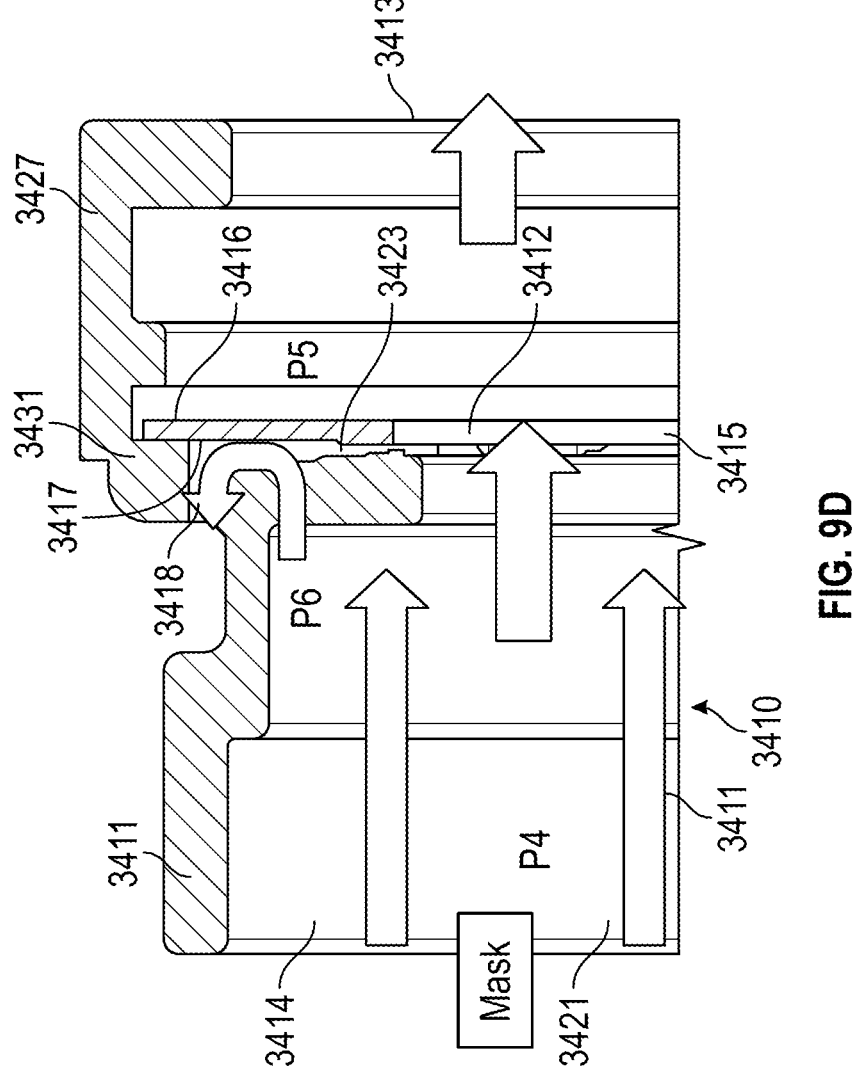

FIG. 9D shows an enlarged region of a portion of FIG. 9B showing the flow pattern during exhalation of a patient in one form of the technology.

Figure 10A:
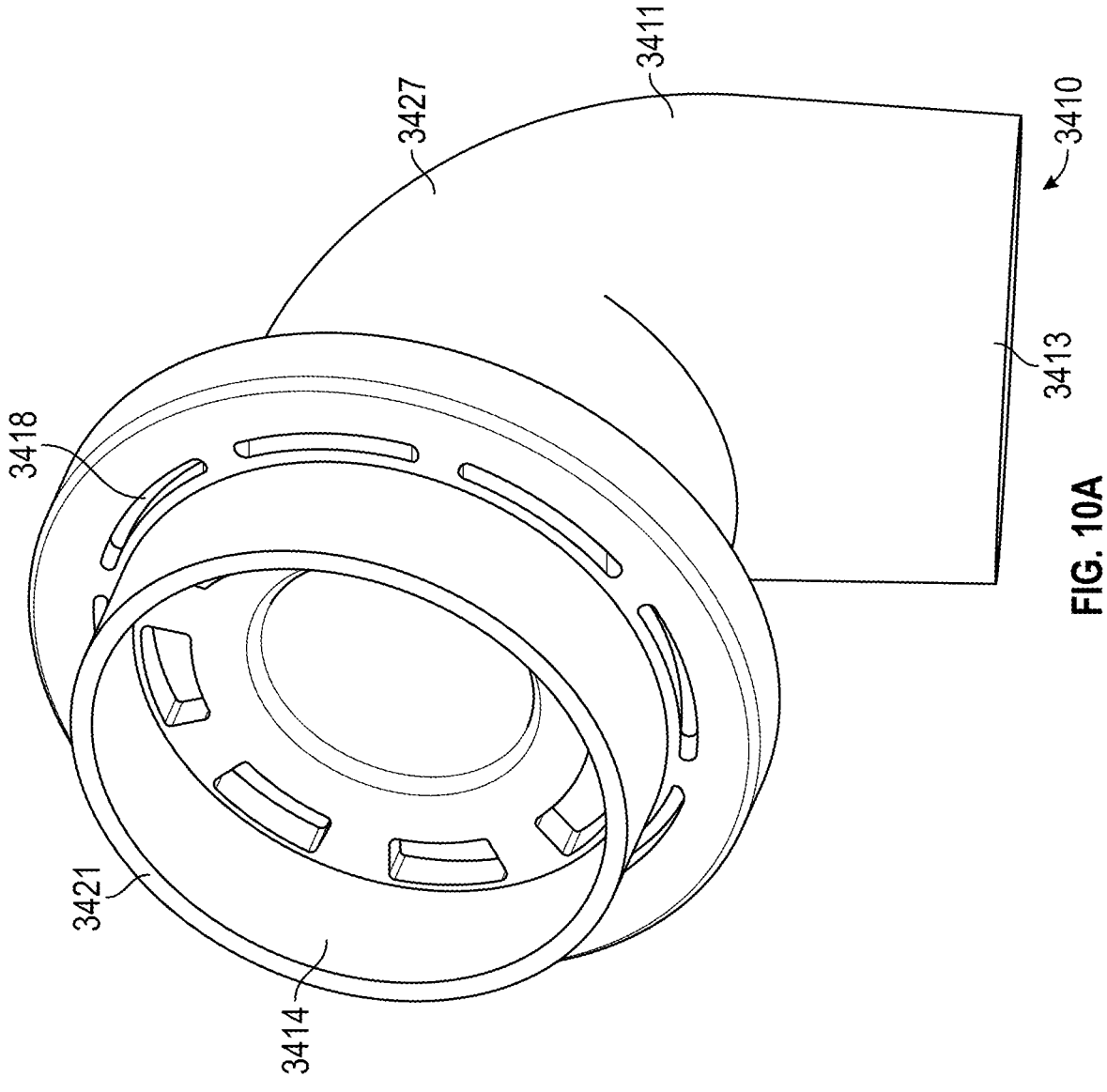

FIG. 10A shows a perspective view of a vent structure connected to an air circuit according to another aspect of the technology.

Figure 10B:
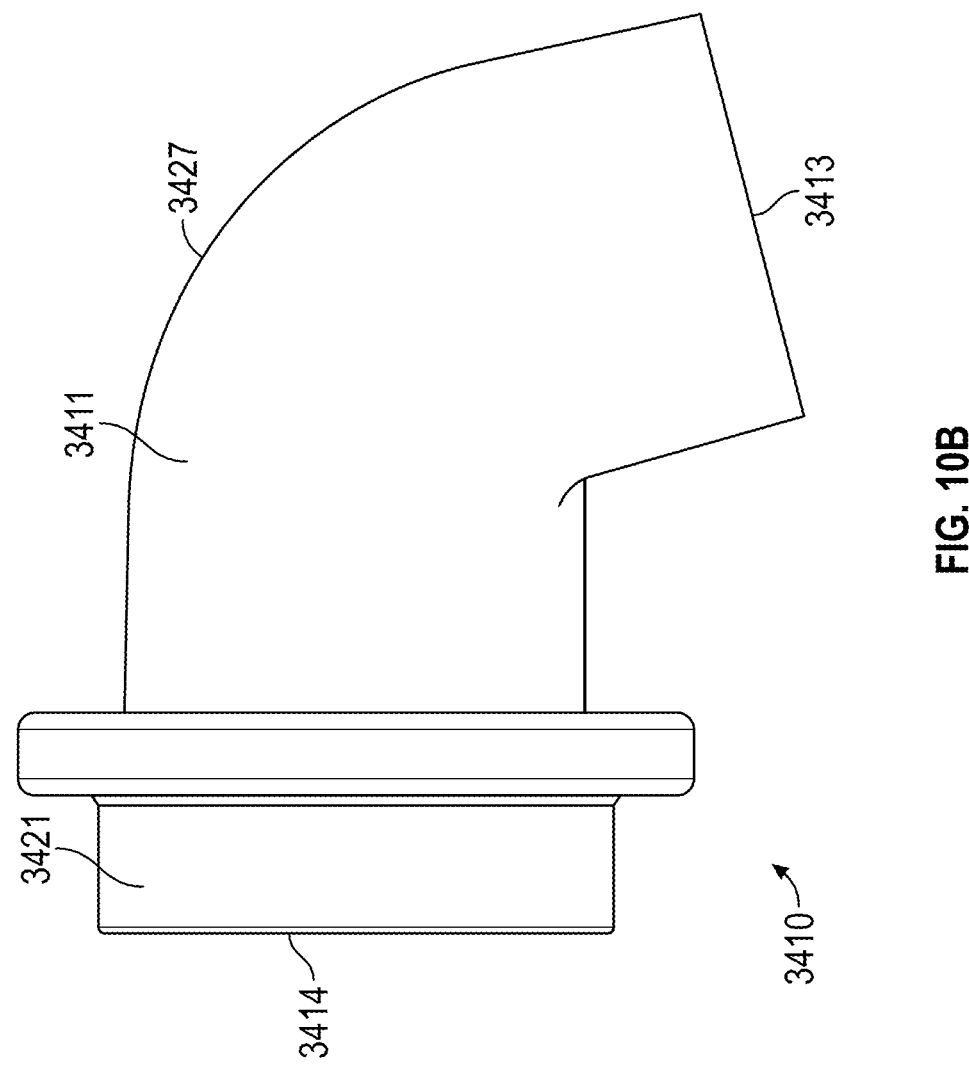

FIG. 10B shows a side view of the vent structure of FIG. 10A.

Figure 10C:
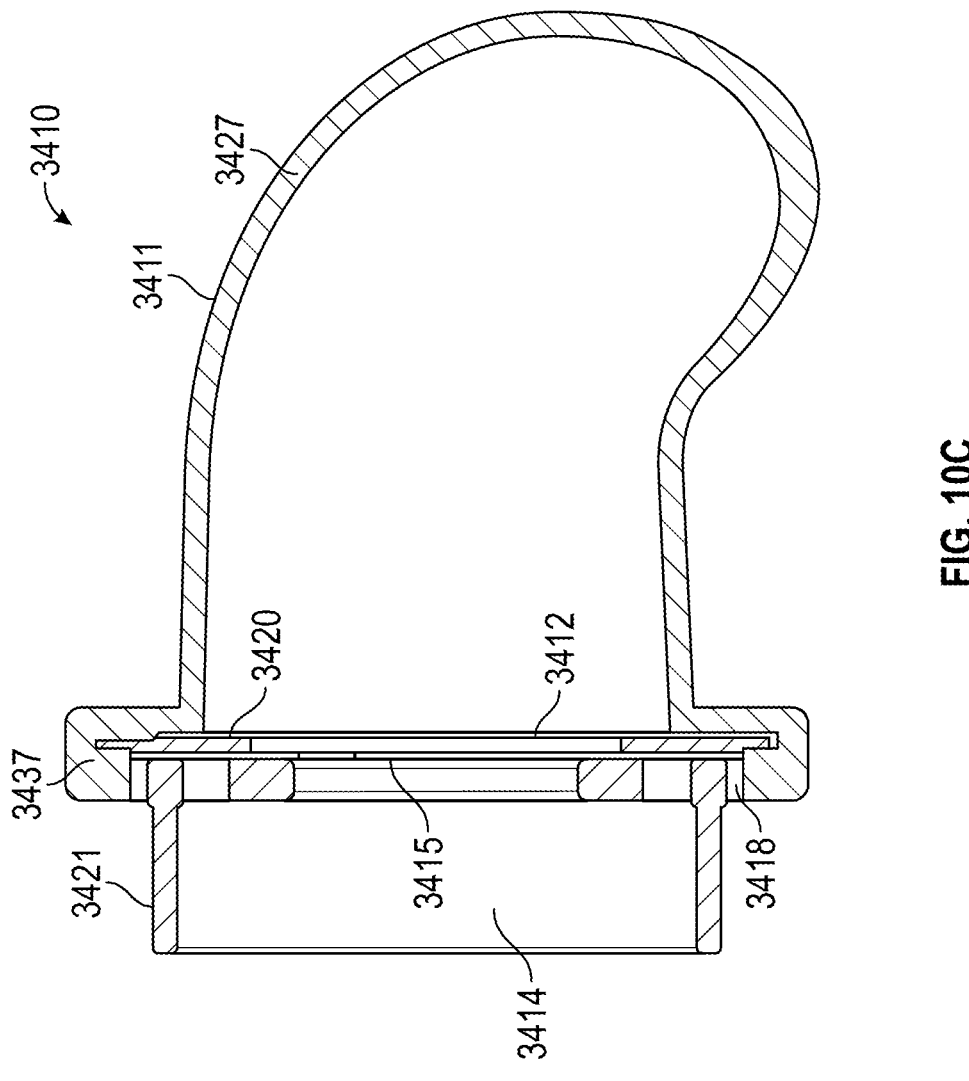

FIG. 10C shows a cross-sectional view of the vent structure of FIG. 10B.

Figure 10D:
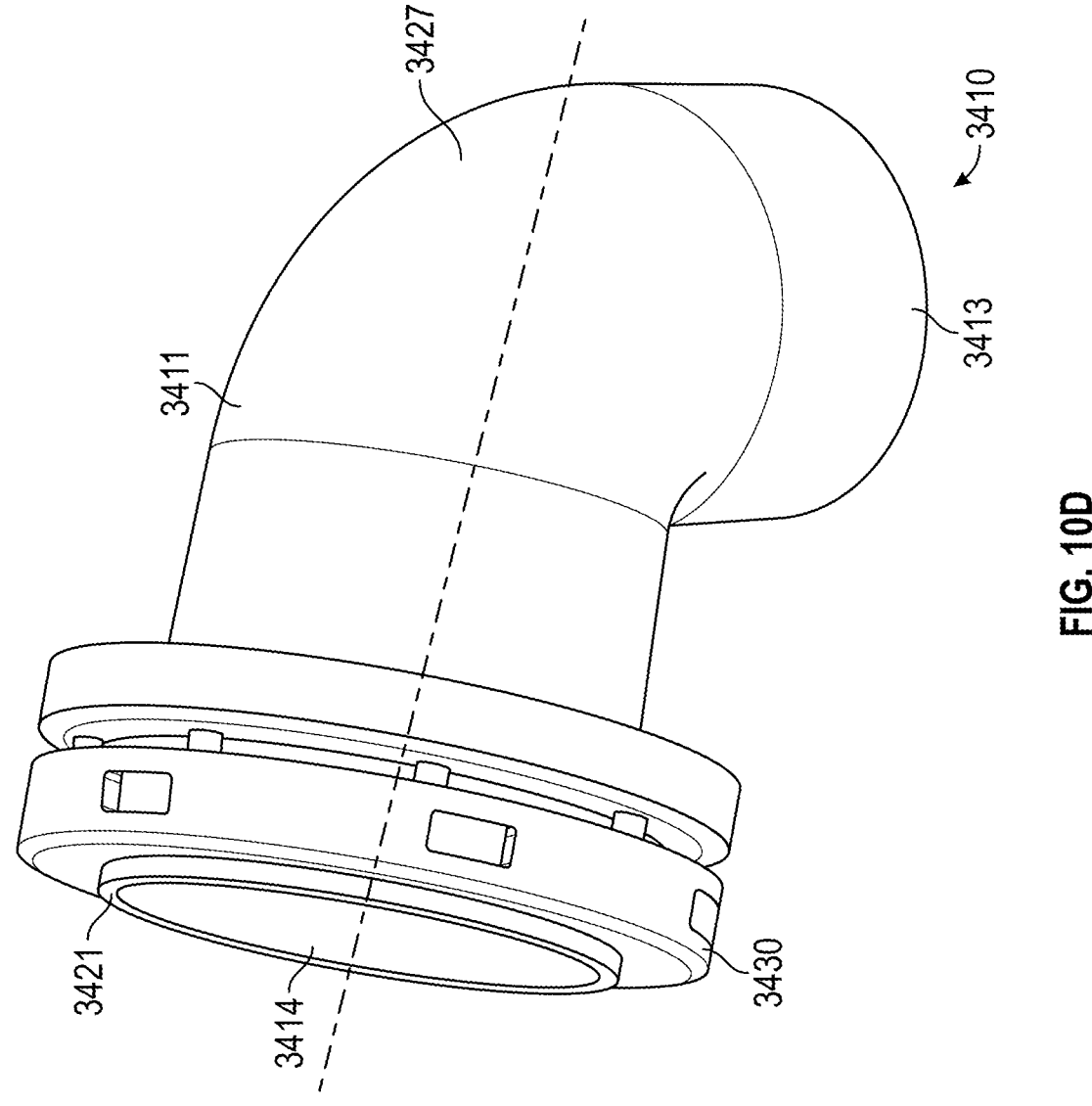

FIG. 10D shows a side perspective view of the vent structure of FIG. 10A with a diffuser.

Figure 10E:
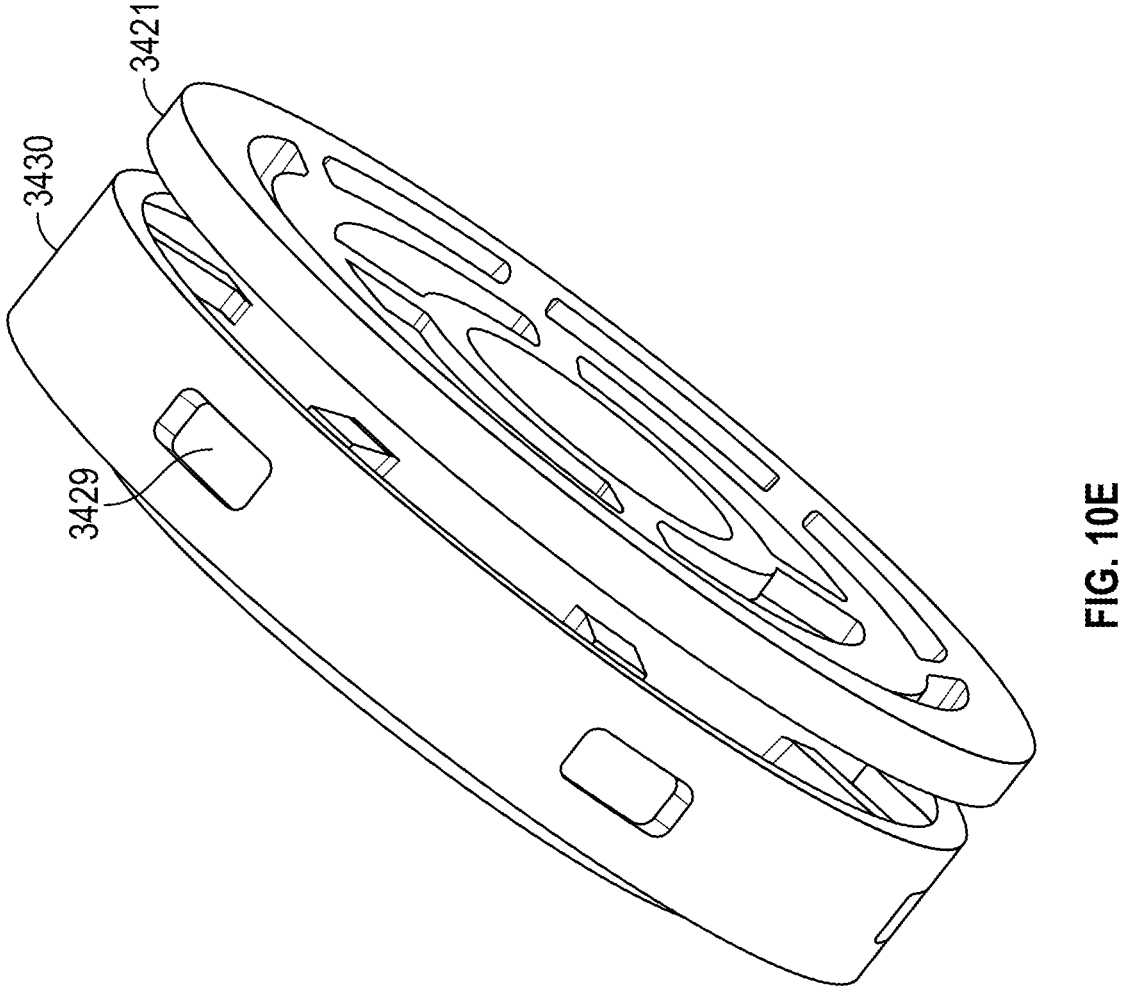

FIG. 10E shows a side perspective view of the vent structure of FIG. 10A with a diffuser of FIG. 10D. The air circuit is not shown.

Figure 10F:
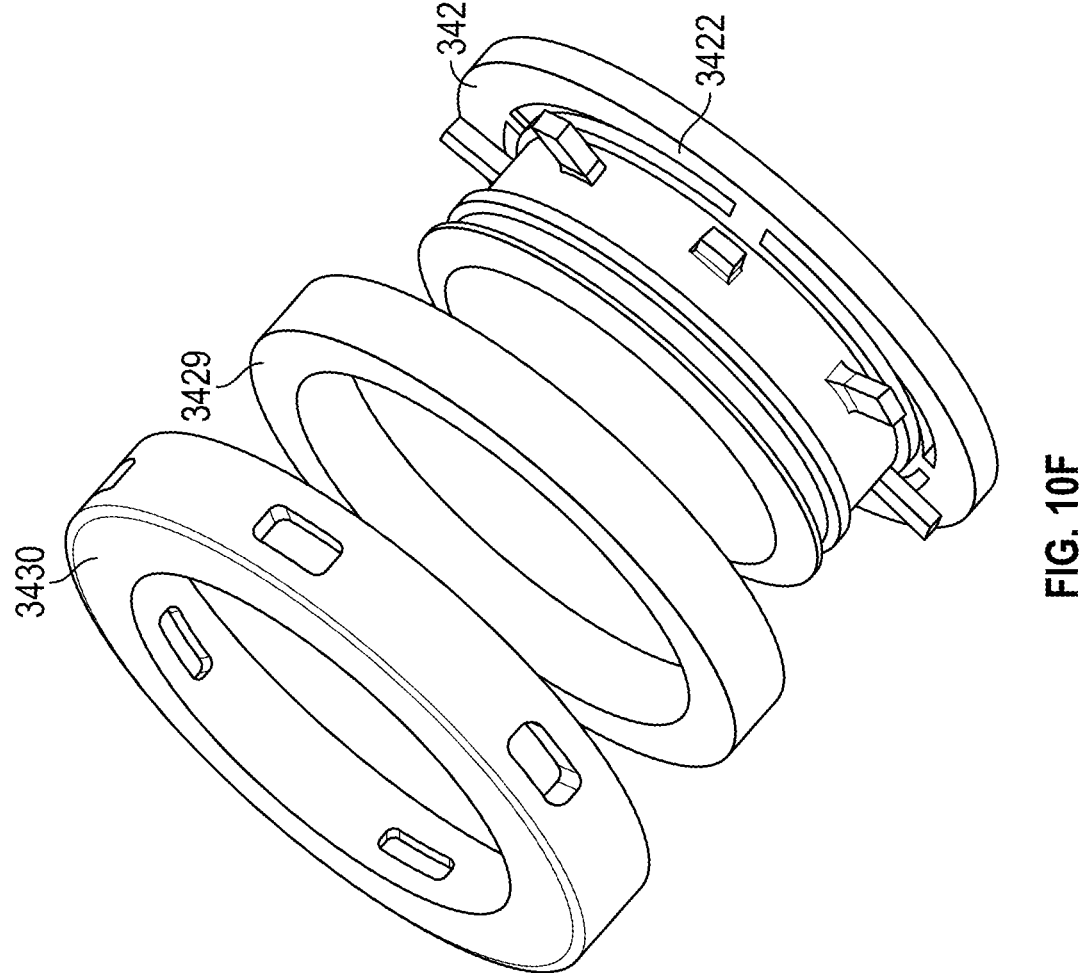

FIG. 10F shows an exploded view of the vent structure of FIG. 10E.

Figure 10G:
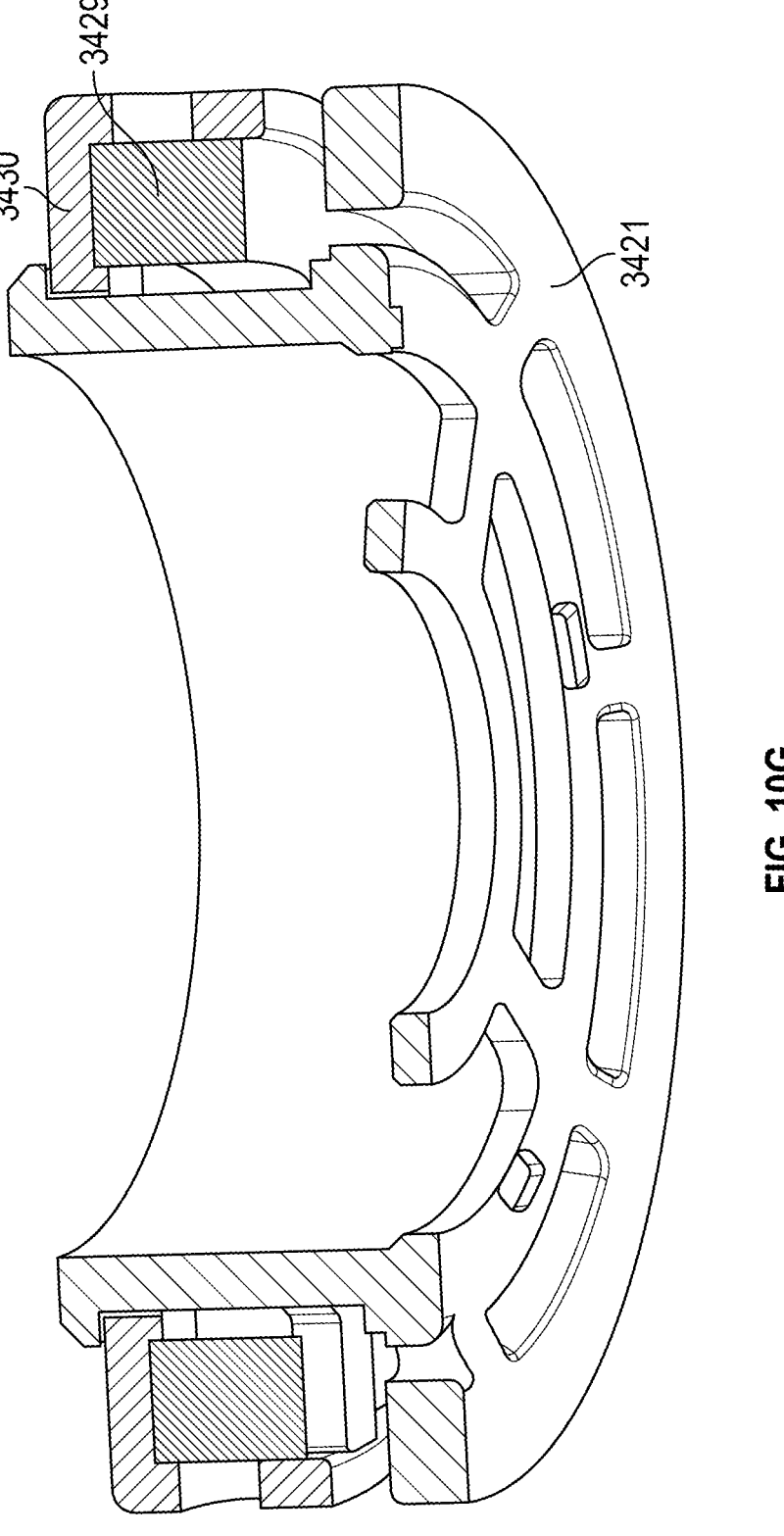

FIG. 10G shows a cross-sectional view of the vent structure of FIG. 10E.

Figure 11A:
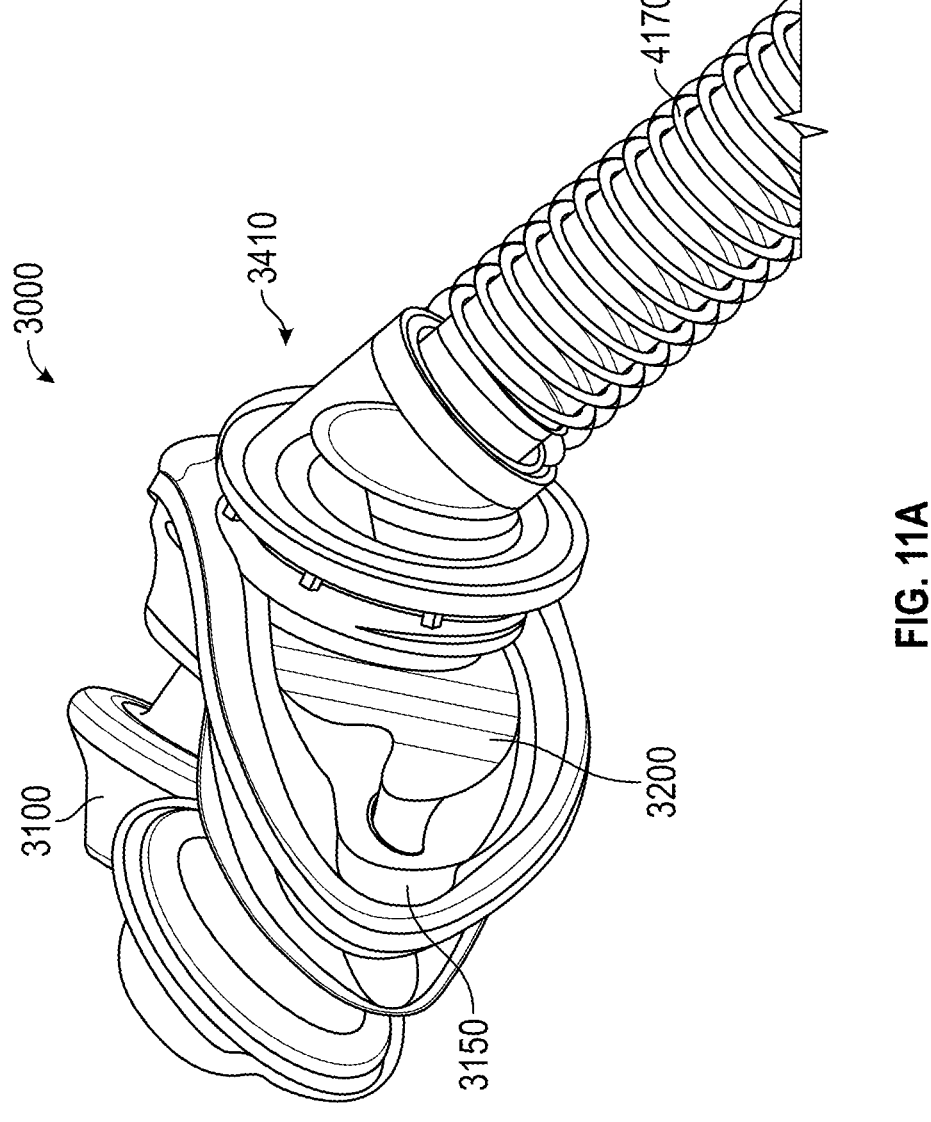

FIG. 11A shows a perspective view of a vent structure according to another form of the technology, the vent structure connected to a seal-forming structure and air circuit.

Figure 11B:
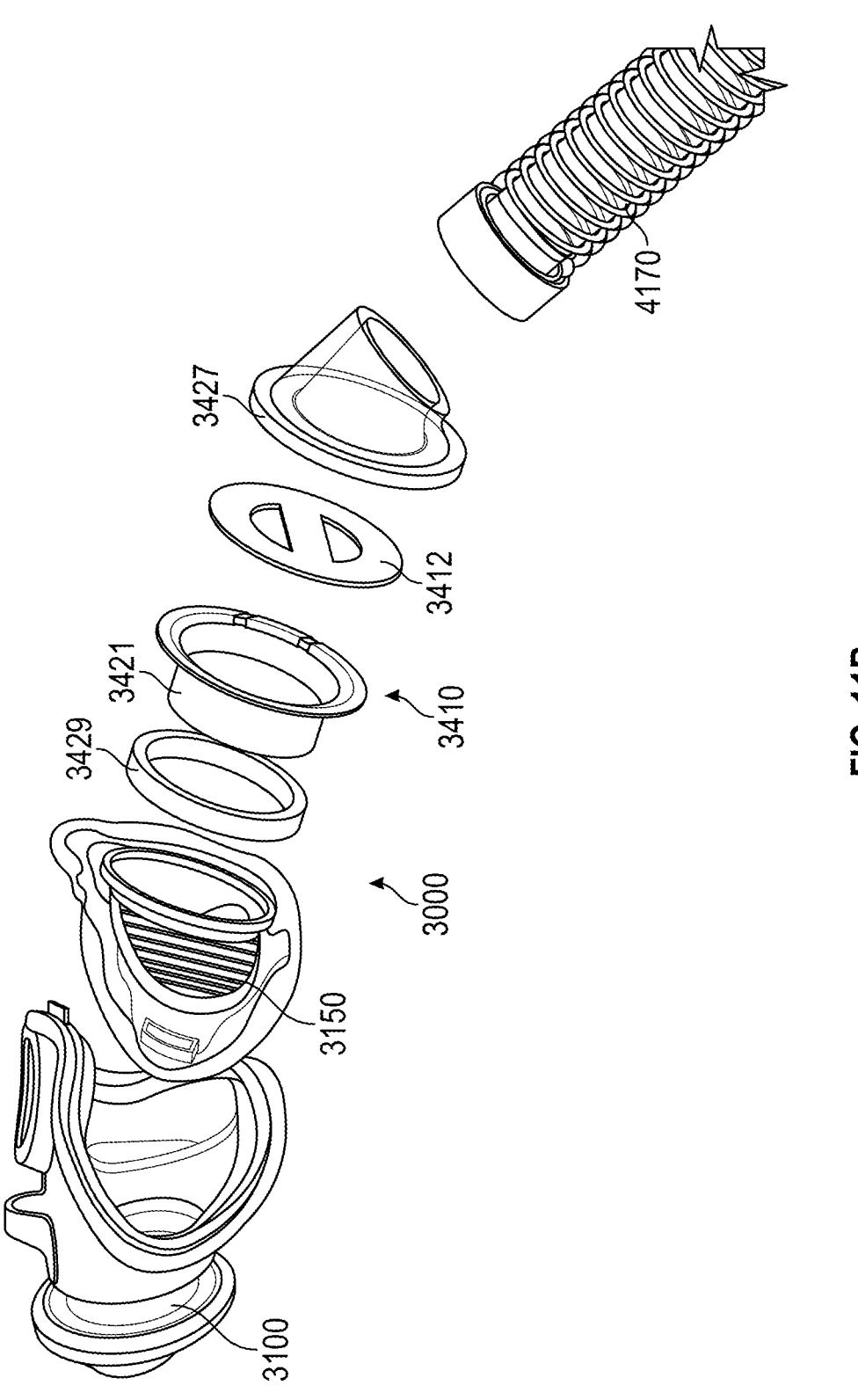

FIG. 11B shows an exploded view of the vent structure, seal-forming structure, and air circuit of FIG. 11A.

Figure 11C:
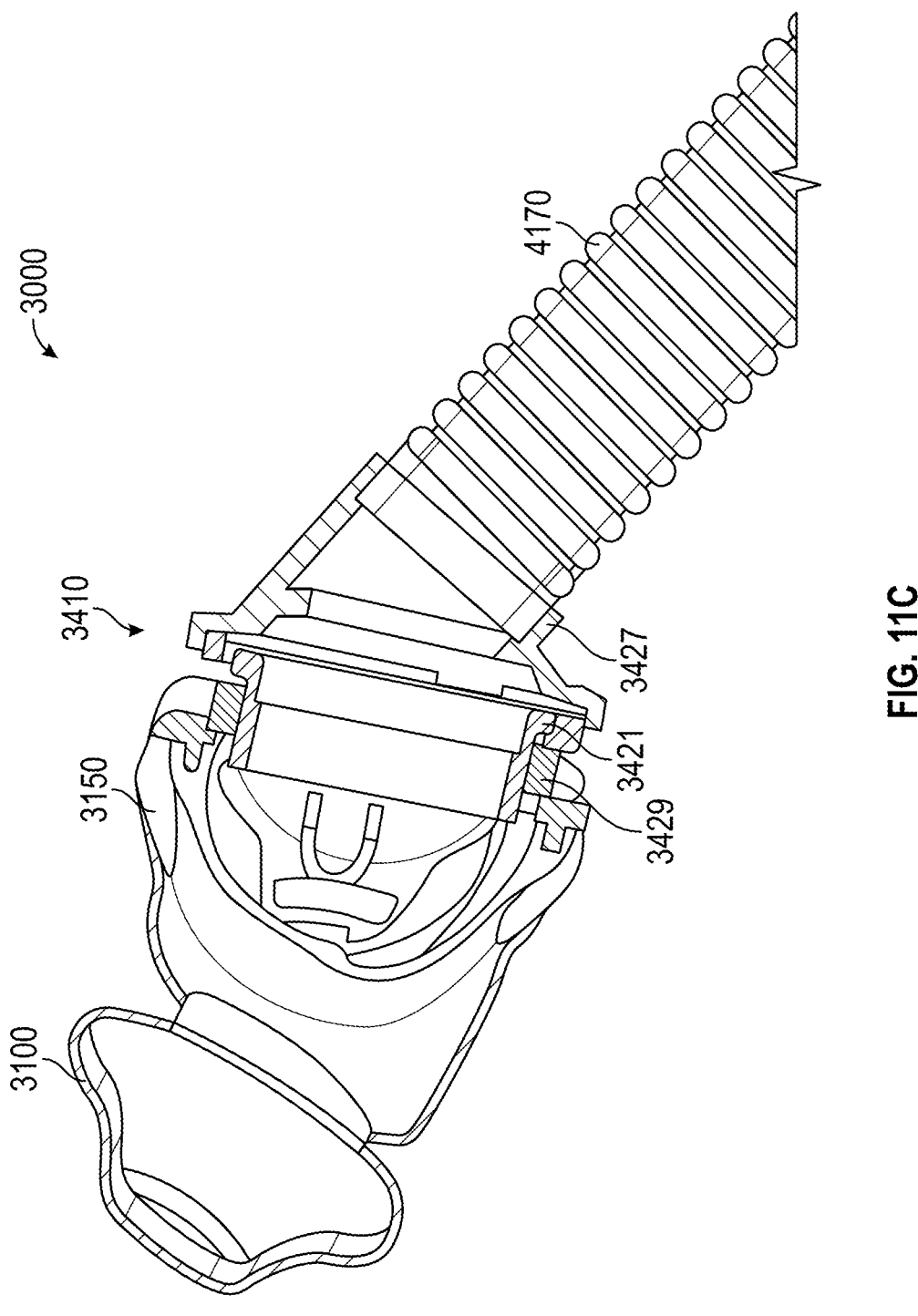

FIG. 11C shows a side cross-sectional view of the vent structure, seal-forming structure, and air circuit of FIG. 11A.

Figure 12:
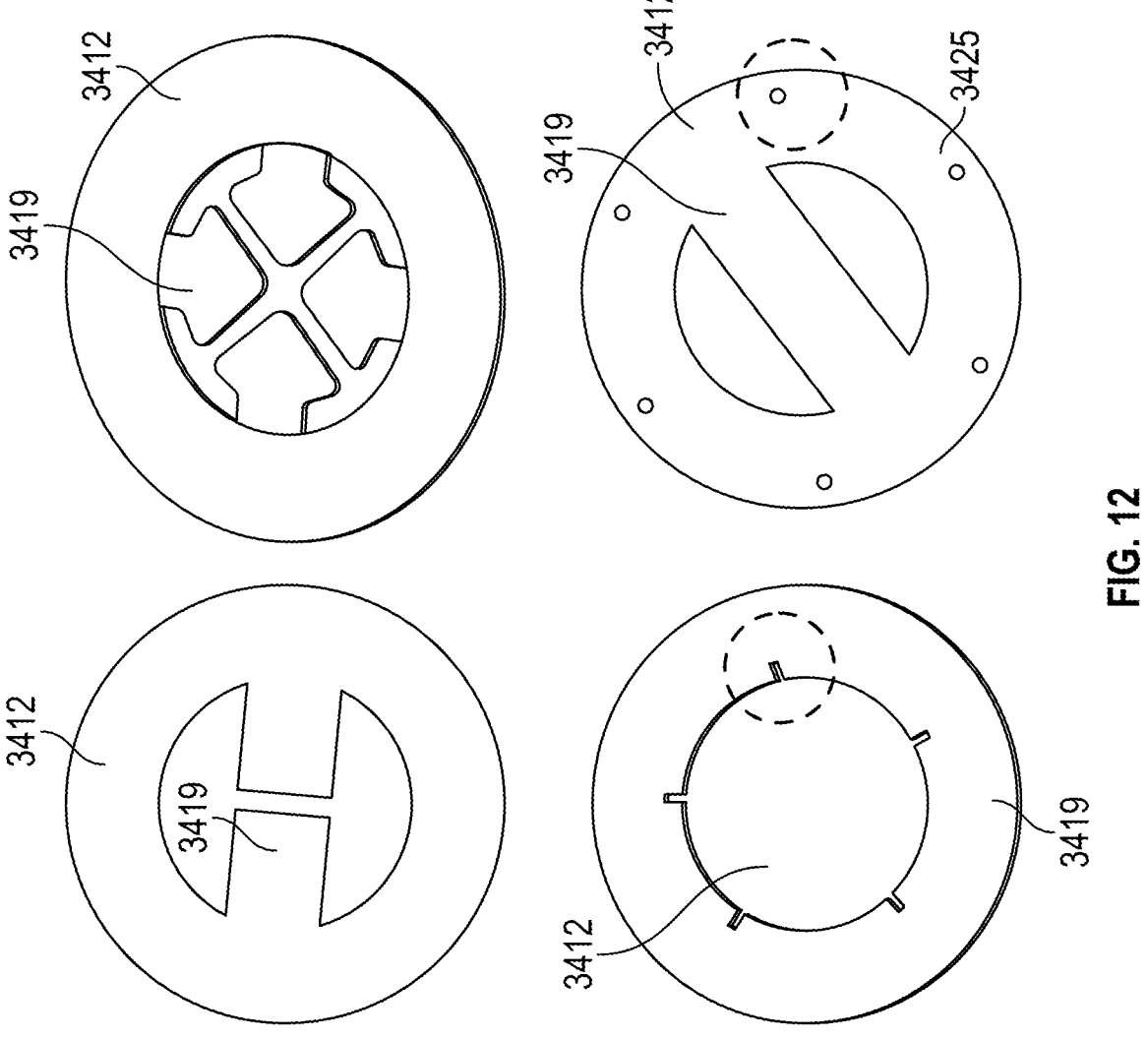

FIG. 12 shows a variety of membrane shapes for a vent structure according to forms of the technology.

Figure 13A:
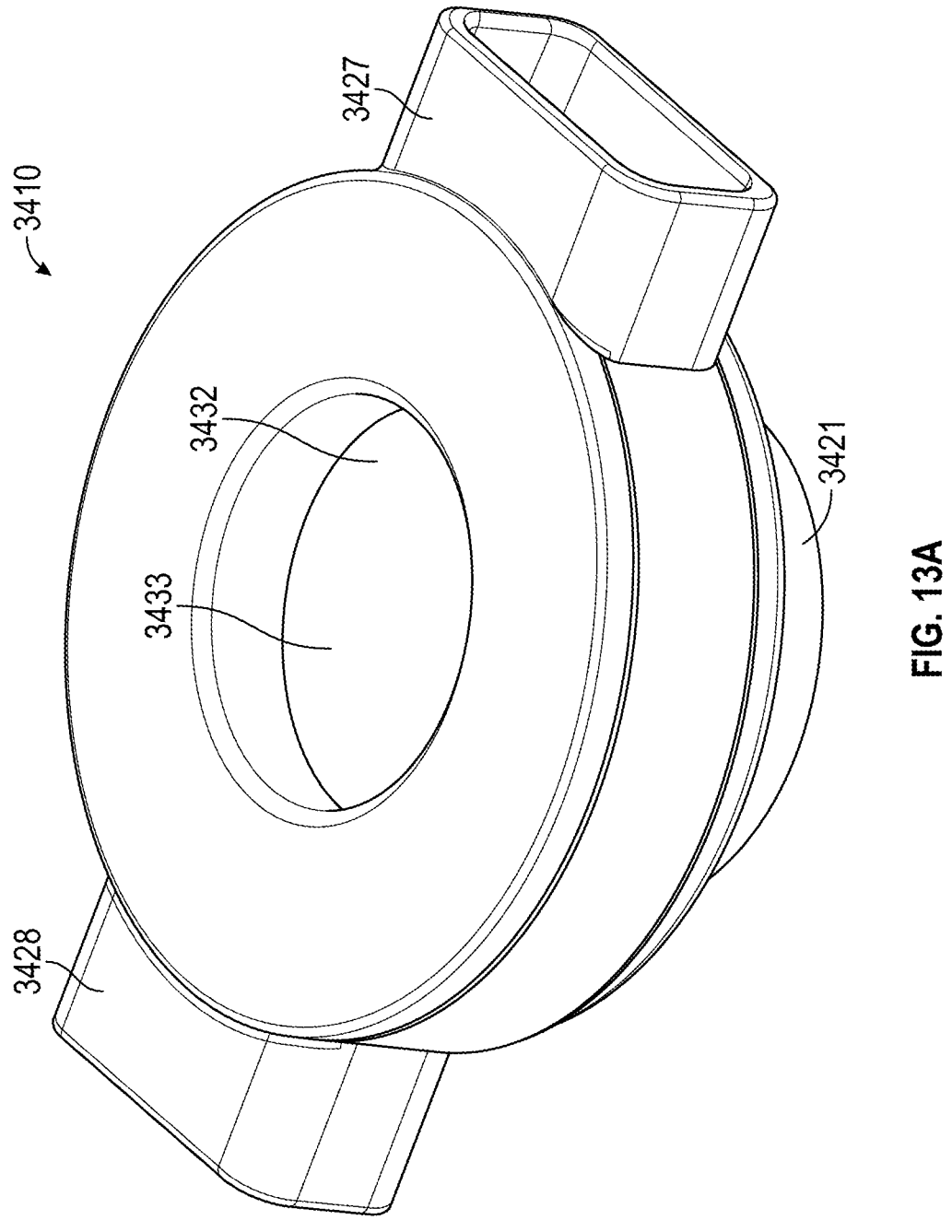

FIG. 13A shows a front perspective view of a vent structure according to another form of the technology.

Figure 13B:
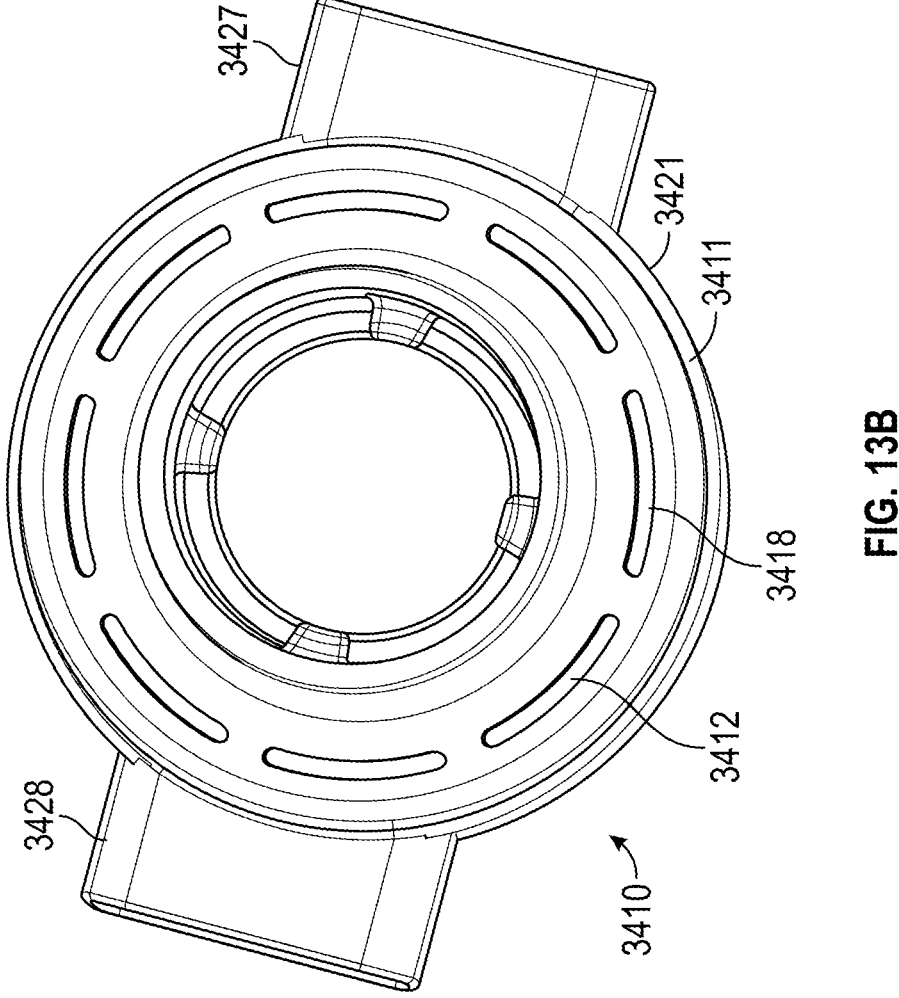

FIG. 13B shows a back view of the vent structure of FIG. 13A.

Figure 13C:
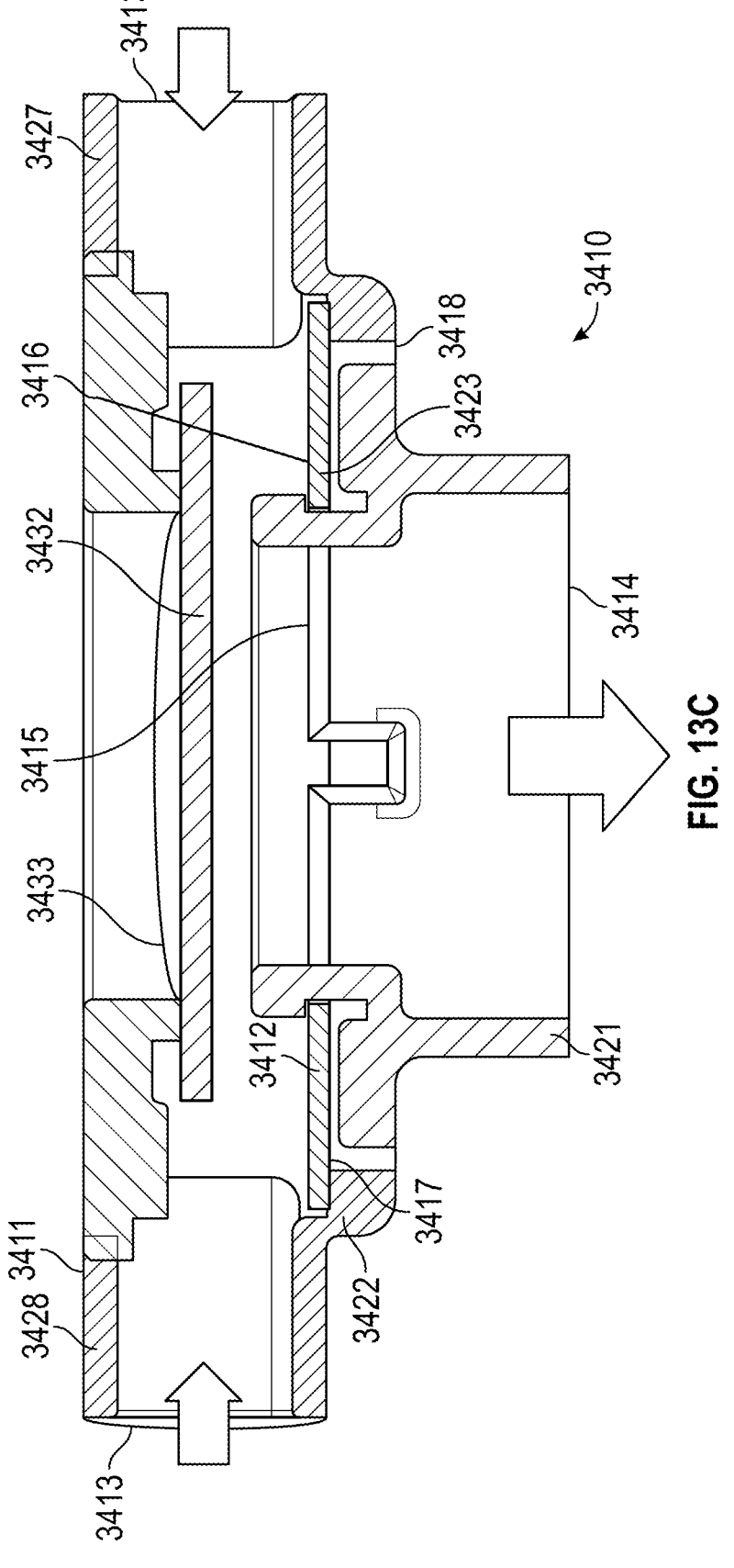

FIG. 13C shows a side cross-sectional view of the vent structure of FIG. 13A.

Figure 13D:
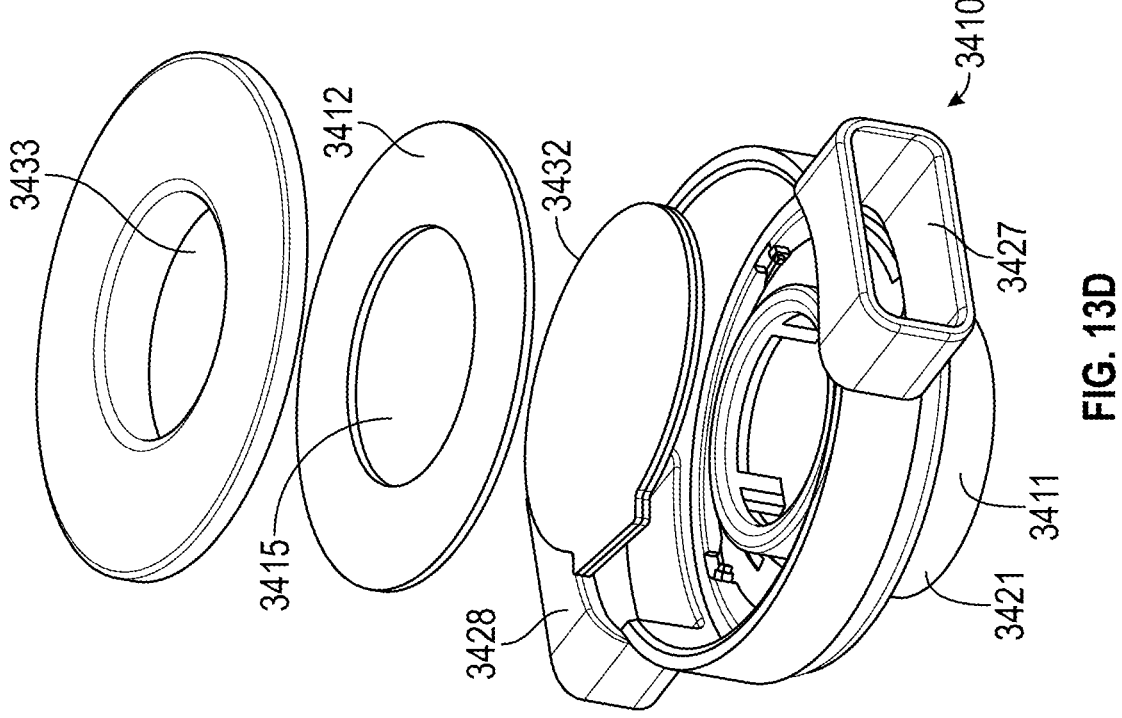

FIG. 13D shows an exploded view of the vent structure of FIG. 13A.

Figure 13E:
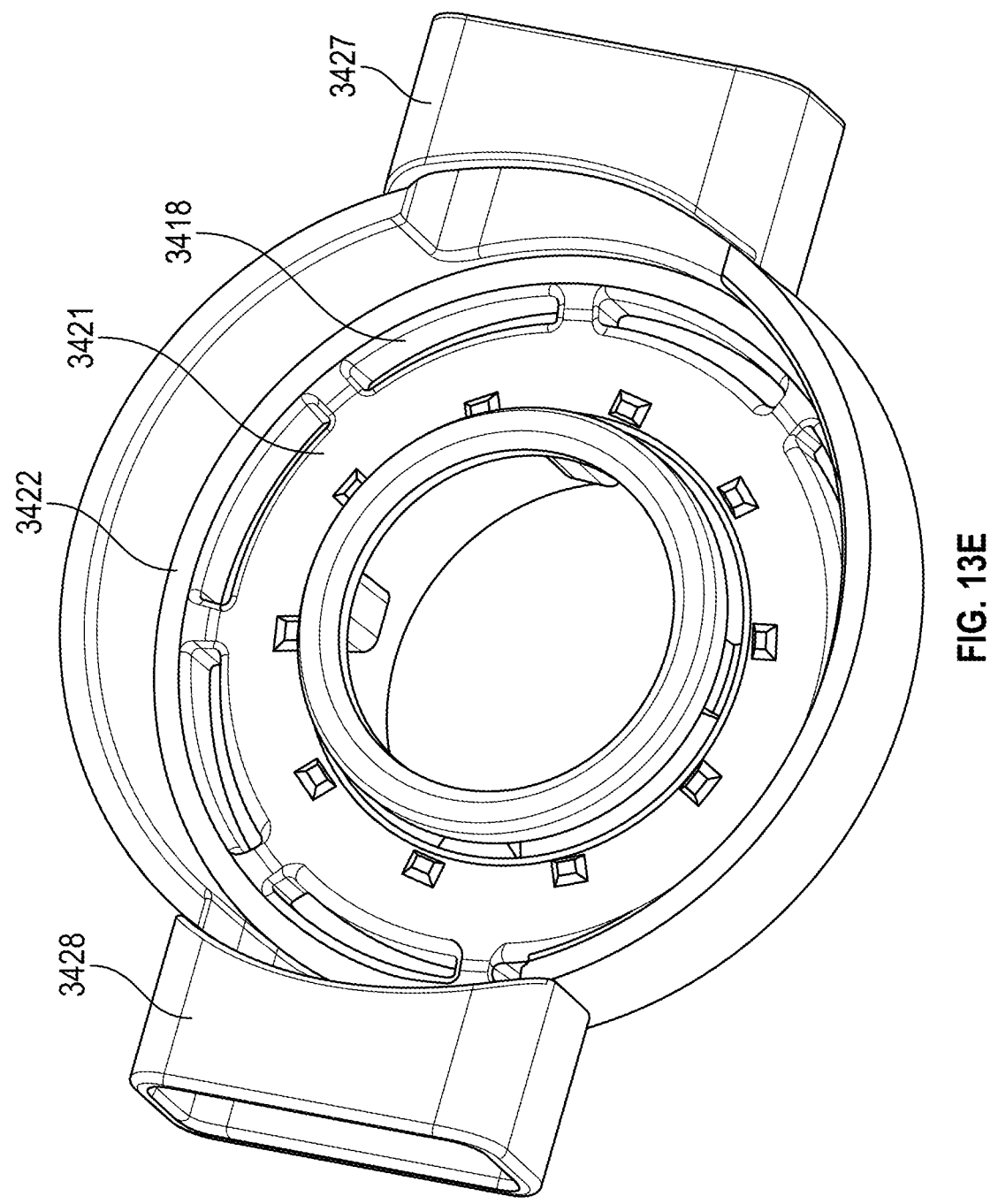

FIG. 13E shows a front perspective view of a part of the vent structure of FIG. 13A.

Figure 13F:
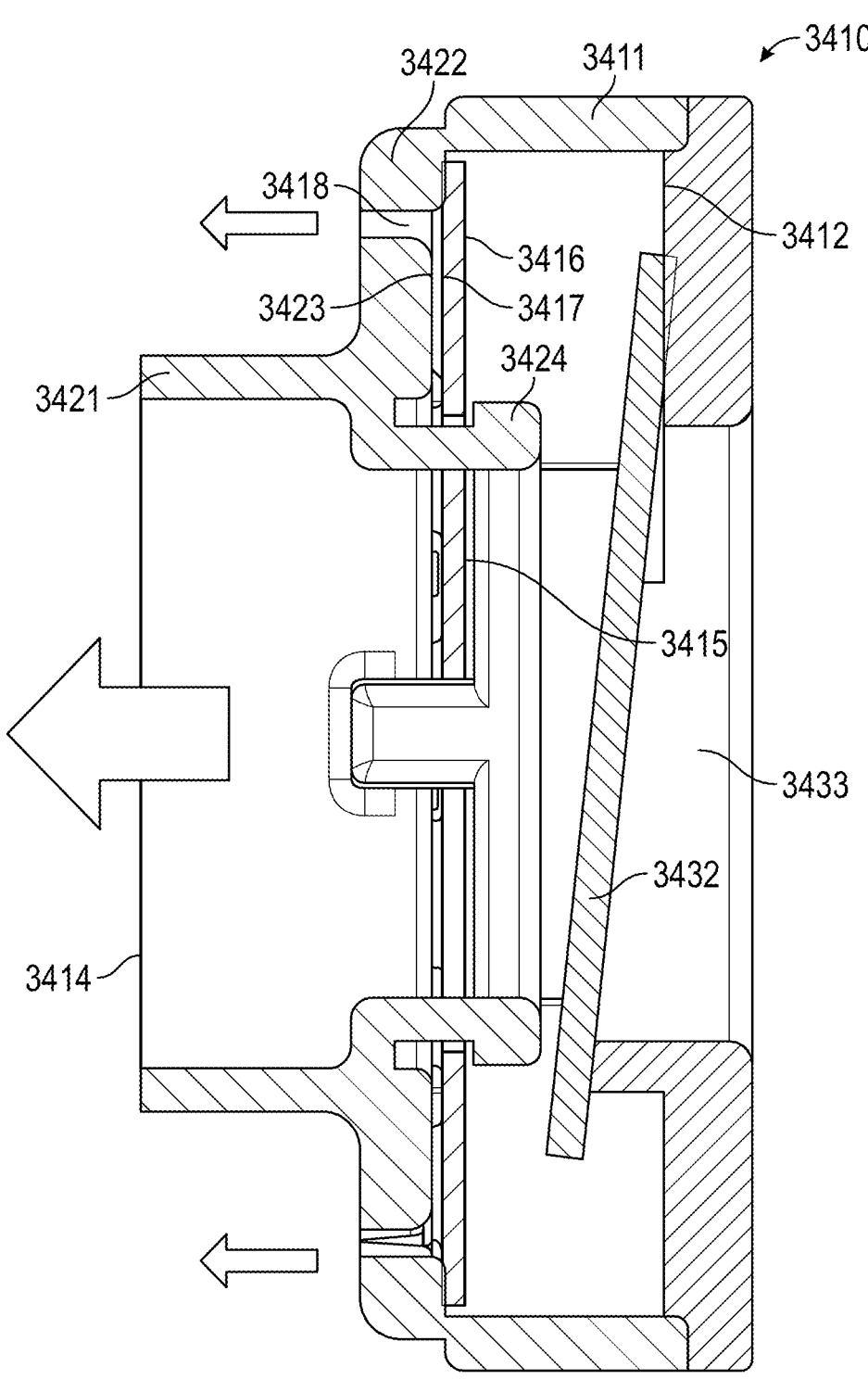

FIG. 13F shows a side cross-sectional view of the vent structure of FIG. 13A when a patient is inhaling in one form of the technology.

Figure 13G:
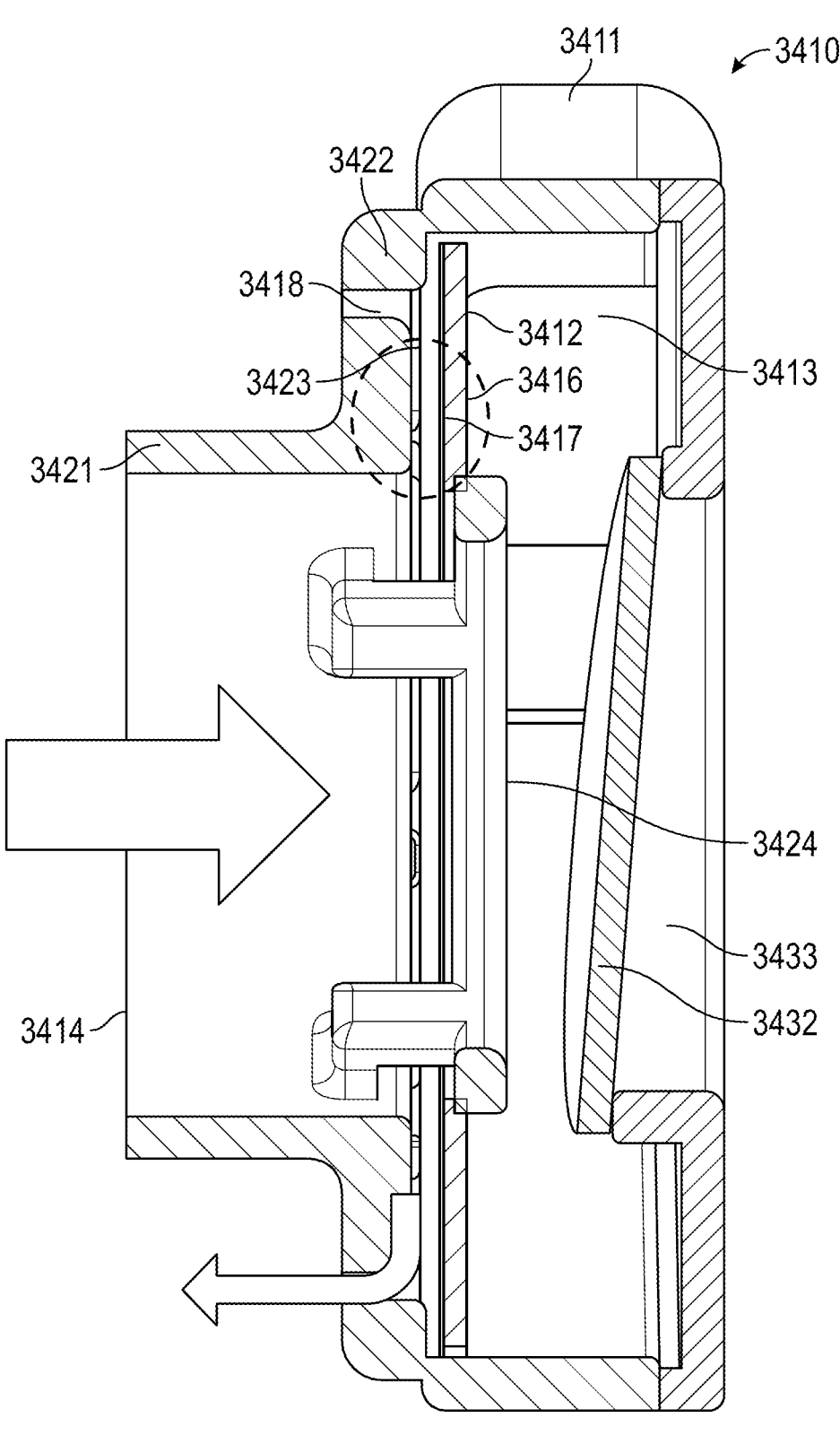

FIG. 13G shows a side cross-sectional view of the vent structure of FIG. 13A when a patient is exhaling in one form of the technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000 or 3800.

5.3 Patient Interface

A non-invasive patient interface 3000, such as that shown in FIG. 3A, in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

Figure 1A:
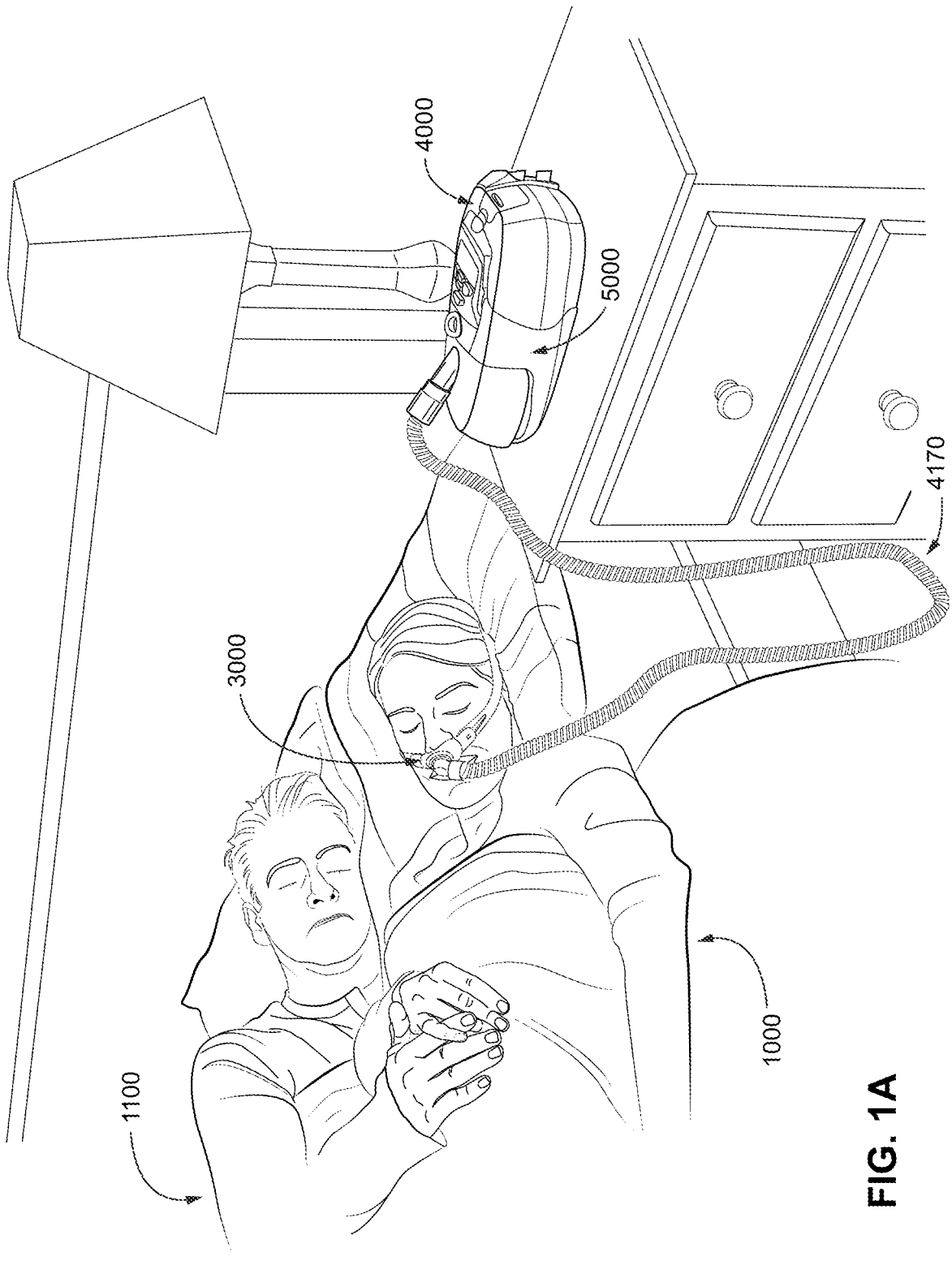
Figure 1B:
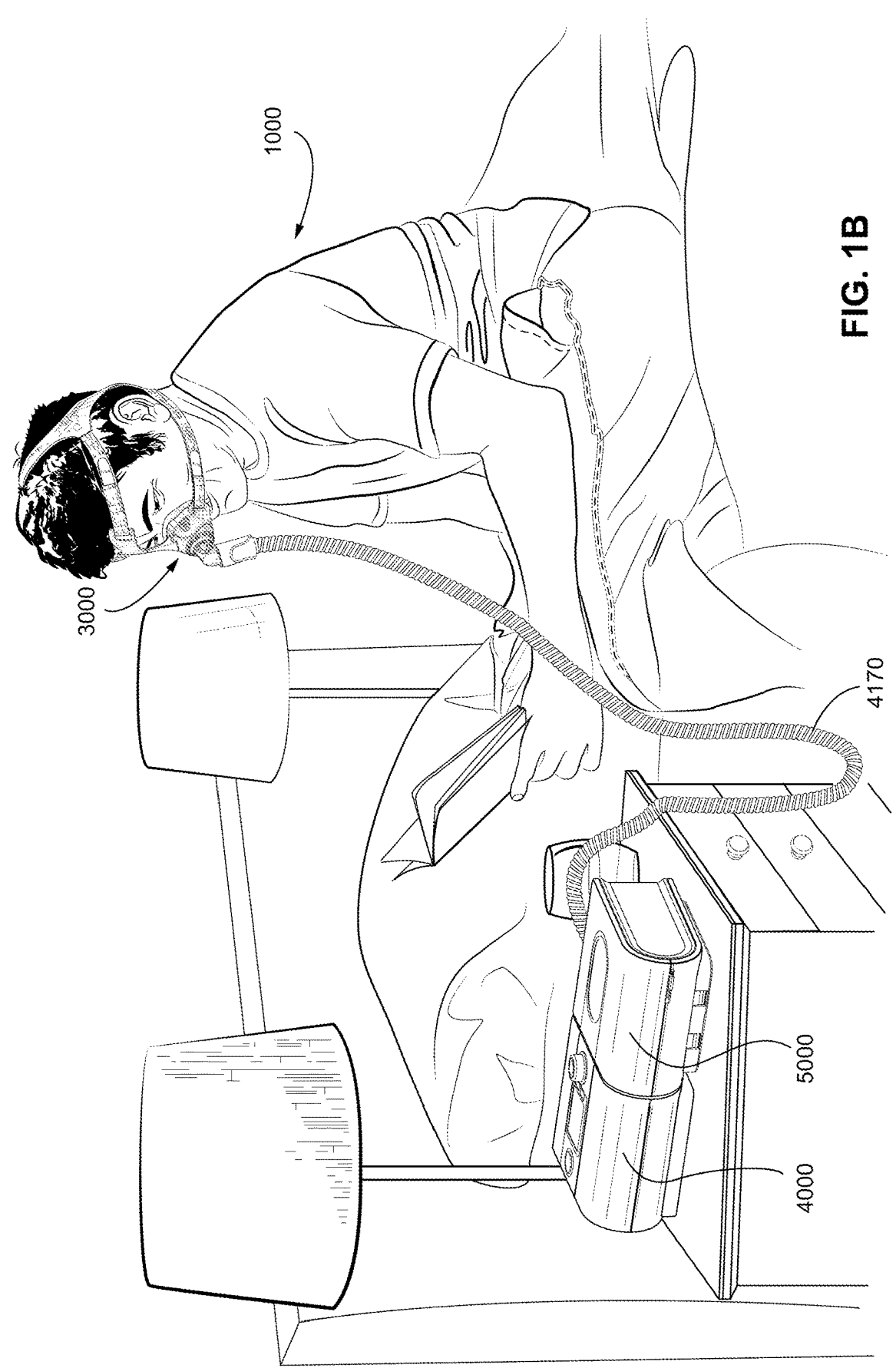
Figure 1C:
Figure 2A:
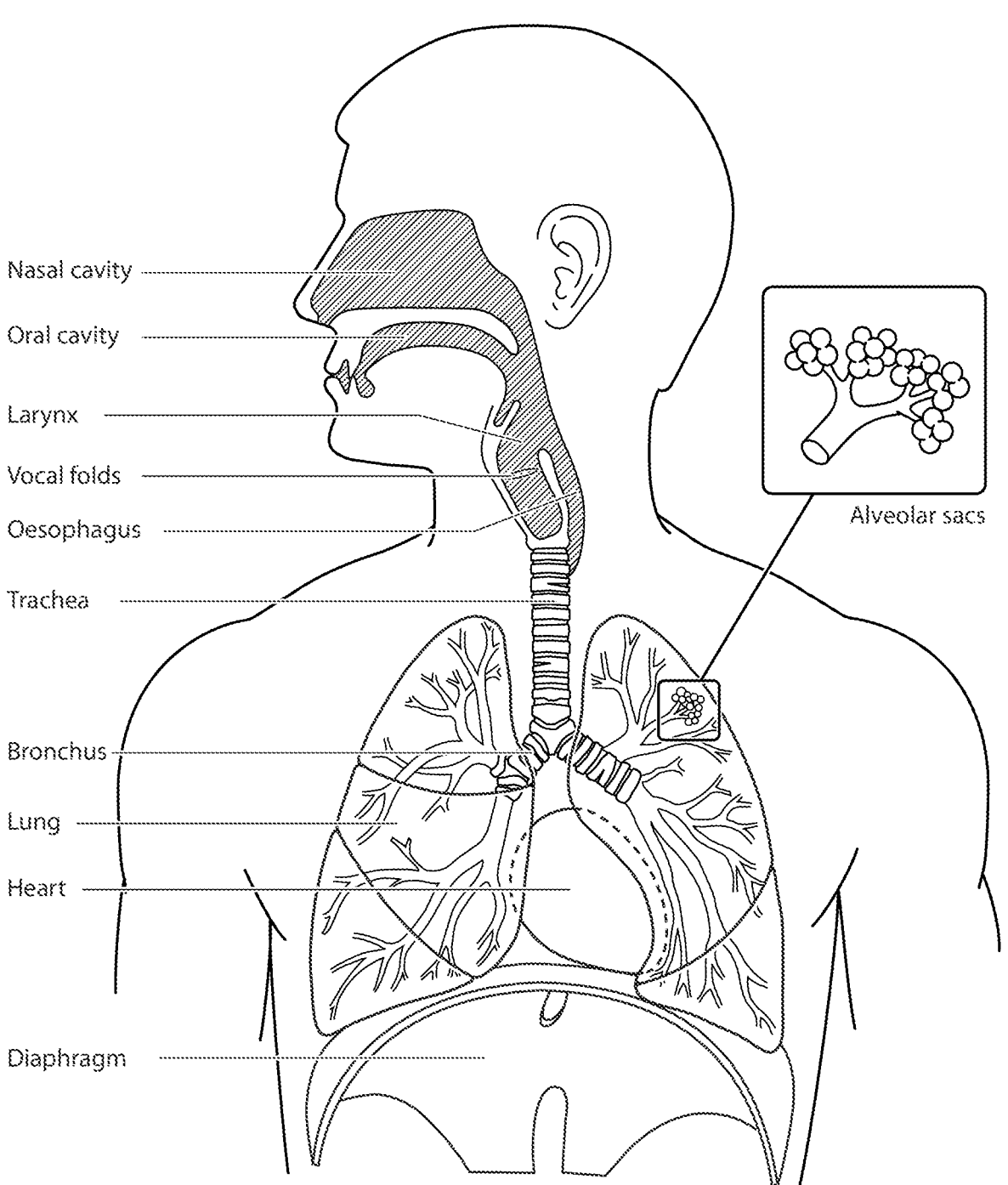

As shown in FIG. 3Z, a non-invasive patient interface 3000 in accordance with another aspect of the present technology comprises the following functional aspects: a seal-forming structure 3000, a plenum chamber 3200, a positioning and stabilising structure 3300, a vent 3400 and one form of connection port 3600 for connection to an air circuit (such as the air circuit 4170 shown in FIGS. 1A-1C). The plenum chamber 3200 may be formed of one or more modular components in the sense that it or they can be replaced with different components, for example components of a different size.

An unsealed patient interface 3800, in the form of a nasal cannula, includes nasal prongs 3810a, 3810b which can deliver air to respective nares of the patient 1000 via respective orifices in their tips. Such nasal prongs do not generally form a seal with the inner or outer skin surface of the nares. This type of interface results in one or more gaps that are present in use by design (intentional) but they are typically not fixed in size such that they may vary unpredictably by movement during use. This can present a complex pneumatic variable for a respiratory therapy system when pneumatic control and/or assessment is implemented, unlike other types of mask-based respiratory therapy systems. The air to the nasal prongs may be delivered by one or more air supply lumens 3820a, 3820b that are coupled with the nasal cannula-type unsealed patient interface 3800. The lumens 3820a, 3820b lead from the nasal cannula-type unsealed patient interface 3800 to a respiratory therapy device via an air circuit. The unsealed patient interface 3800 is particularly suitable for delivery of flow therapies, in which the RPT device generates the flow of air at controlled flow rates rather than controlled pressures. The "vent" or gap at the unsealed patient interface 3800, through which excess airflow escapes to ambient, is the passage between the end of the prongs 3810a and 3810b of the nasal cannula-type unsealed patient interface 3800 via the patient's nares to atmosphere.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.2 Nose-Only Masks

In one form, the patient interface 3000 comprises a seal-forming structure 3100 configured to seal around an entrance to the patient's nasal airways but not around the patient's mouth. The seal-forming structure 3100 may be configured to seal to the patient's lip superior. The patient interface 3000 may leave the patient's mouth uncovered. This patient interface 3000 may deliver a supply of air or breathable gas to both nares of patient 1000 and not to the mouth. This type of patient interface may be identified as a nose-only mask.

One form of nose-only mask according to the present technology is what has traditionally been identified as a "nasal mask", having a seal-forming structure 3100 configured to seal on the patient's face around the nose and over the bridge of the nose. A nasal mask may be generally triangular in shape. In one form, the non-invasive patient interface 3000 comprises a seal-forming structure 3100 that forms a seal in use to an upper lip region (e.g. the lip superior), to the patient's nose bridge or at least a portion of the nose ridge above the pronasale, and to the patient's face on each lateral side of the patient's nose, for example proximate the patient's nasolabial sulci. The patient interface 3000 shown in FIG. 1B has this type of seal-forming structure 3100. This patient interface 3000 may deliver a supply of air or breathable gas to both nares of patient 1000 through a single orifice.

Another form of nose-only mask may seal around an inferior periphery of the patient's nose without engaging the user's nasal ridge. This type of patient interface 3000 may be identified as a "nasal cradle" mask and the seal-forming structure 3100 may be identified as a "nasal cradle cushion", for example. In one form, for example as shown in FIG. 3Z, the seal-forming structure 3100 is configured to form a seal in use with inferior surfaces of the nose around the nares. The seal-forming structure 3100 may be configured to seal around the patient's nares at an inferior periphery of the patient's nose including to an inferior and/or anterior surface of a pronasale region of the patient's nose and to the patient's nasal alae. The seal-forming structure 3100 may seal to the patient's lip superior. The shape of the seal-forming structure 3100 may be configured to match or closely follow the underside of the patient's nose and may not contact a nasal bridge region of the patient's nose or any portion of the patient's nose superior to the pronasale. In one form of nasal cradle cushion, the seal-forming structure 3100 comprises a bridge portion dividing the opening into two orifices, each of which, in use, supplies air or breathable gas to a respective one of the patient's nares. The bridge portion may be configured to contact or seal against the patient's columella in use. Alternatively, the seal-forming structure 3100 may comprise a single opening to provide a flow or air or breathable gas to both of the patient's nares.

In some forms, a nose-only mask may comprise nasal pillows, described above.

5.3.1.3 Nose and Mouth Masks

In one form, the patient interface 3000 comprises a seal-forming structure 3100 configured to seal around an entrance to the patient's nasal airways and also around the patient's mouth. The seal-forming structure 3100 may be configured to seal to the patient's face proximate a chin region. This patient interface 3000 may deliver a supply of air or breathable gas to both nares and to the mouth of patient 1000. This type of patient interface may be identified as a nose and mouth mask.

One form of nose and mouth mask according to the present technology is what has traditionally been identified as a "full-face mask", having a seal-forming structure 3100 configured to seal on the patient's face around the nose, below the mouth and over the bridge of the nose. A full-face mask may be generally triangular in shape. In one form the patient interface 3000 comprises a seal-forming structure 3100 that forms a seal in use to a patient's chin-region (which may include the patient's lip inferior and/or a region directly inferior to the lip inferior), to the patient's nose bridge or at least a portion of the nose ridge superior to the pronasale, and to cheek regions of the patient's face. The patient interface 3000 shown in FIG. 1C is of this type. This patient interface 3000 may deliver a supply of air or breathable gas to both nares and mouth of patient 1000 through a single orifice. This type of seal-forming structure 3100 may be referred to as a "full face cushion".

In another form the patient interface 3000 comprises a seal-forming structure 3100 that forms a seal in use on a patient's chin region (which may include the patient's lip inferior and/or a region directly inferior to the lip inferior), to an inferior and/or an anterior surface of a pronasale portion of the patient's nose, to the alae of the patient's nose and to the patient's face on each lateral side of the patient's nose, for example proximate the nasolabial sulci. The seal-forming structure 3100 may also form a seal against a patient's lip superior. A patient interface 3000 having this type of seal-forming structure may have a single opening configured to deliver a flow of air or breathable gas to both nares and mouth of a patient, may have an oral hole configured to provide air or breathable gas to the mouth and a nasal hole configured to provide air or breathable gas to the nares, or may have an oral hole for delivering air to the patient's mouth and two nasal holes for delivering air to respective nares. This type of patient interface 3000 may have a nasal portion and an oral portion, the nasal portion sealing to the patient's face at similar locations to a nasal cradle mask.

In a further form of nose and mouth mask, the patient interface 3000 may comprise a seal-forming structure 3100 having a nasal portion comprising nasal pillows and an oral portion configured to form a seal to the patient's face around the patient's mouth.

In some forms, the seal-forming structure 3100 may have a nasal portion that is separate and distinct from an oral portion. In other forms, a seal-forming structure 3100 may form a contiguous seal around the patient's nose and mouth.

It is to be understood that the above examples of different forms of patient interface 3000 do not constitute an exhaustive list of possible configurations. In some forms a patient interface 3000 may comprise a combination of different features of the above described examples of nose-only and nose and mouth masks.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

The plenum chamber comprises a plenum chamber inlet port sized and structured to receive the flow air at the therapeutic pressure for breathing by the patient and to convey the flow of air into the plenum chamber. In some forms, the plenum chamber inlet port may be located in an anterior central region of the plenum chamber. In other forms, the plenum chamber may comprise a plurality of inlet ports, for example two inlet ports on each lateral side of the plenum chamber. Two ports may be used when the positioning and stabilising structure 3300 of the patient interface 3000 comprises tubes 3350 for conveying air to the plenum chamber.

5.3.3 Positioning and Stabilising Structure

The seal-forming structure 3100 of the patient interface 3000 of the present technology may be held in sealing position in use by the positioning and stabilising structure 3300. The positioning and stabilising structure 3300 may comprise and function as "headgear" since it engages the patient's head in order to hold the patient interface 3000 in a sealing position.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Conduit Headgear 5.3.3.1.1 Conduit Headgear Tubes

In some forms of the present technology, the positioning and stabilising structure 3300 comprises one or more headgear tubes 3350 that deliver pressurised air received from a conduit forming part of the air circuit 4170 from the RPT device to the patient's airways, for example through the plenum chamber 3200 and seal-forming structure 3100. In the form of the present technology illustrated in FIG. 3Z, the positioning and stabilising structure 3300 comprises two tubes 3350 that deliver air to the plenum chamber 3200 from the air circuit 4170. The tubes 3350 are configured to position and stabilise the seal-forming structure 3100 of the patient interface 3000 at the appropriate part of the patient's face (for example, the nose and/or mouth) in use. This allows the conduit of air circuit 4170 providing the flow of pressurised air to connect to a connection port 3600 of the patient interface in a position other than in front of the patient's face, for example on top of the patient's head.

In the form of the present technology illustrated in FIG. 3Z, the positioning and stabilising structure 3300 comprises two tubes 3350, each tube 3350 being positioned in use on a different side of the patient's head and extending across the respective cheek region, above the respective ear (superior to the otobasion superior on the patient's head) to the elbow 3610 on top of the head of the patient 1000. This form of technology may be advantageous because, if a patient sleeps with their head on its side and one of the tubes 3350 is compressed to block or partially block the flow of gas along the tube 3350, the other tube 3350 remains open to supply pressurised gas to the patient. In other examples of the technology, the patient interface 3000 may comprise a different number of tubes, for example one tube, or two or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the form of the technology shown in FIG. 3Z the two tubes 3350 are fluidly connected at superior ends to each other and to the connection port 3600. In some examples, the two tubes 3350 are integrally formed while in other examples the tubes 3350 are formed separately but are connected in use and may be disconnected, for example for cleaning or storage. Where separate tubes are used they may be indirectly connected together, for example each may be connected to a T-shaped connector having two arms/branches each fluidly connectable to a respective one of the tubes 3350 and a third arm or opening in the T-shaped connector providing the connection port 3600 for fluid connection to the air circuit 4170 in use.

The tubes 3350 may be formed from a flexible material, such as an elastomer, e.g. silicone or TPE, and/or from one or more textile and/or foam materials. The tubes 3350 may have a preformed shape and may be able to be bent or moved into another shape upon application of a force but may return to the original preformed shape in the absence of said force. The tubes 3350 may be generally arcuate or curved in a shape approximating the contours of a patient's head between the top of the head and the nasal or oral region.

In some examples, the one or more tubes 3350 are crush resistant to resist being blocked if crushed during use, for example if squashed between a patient's head and pillow, especially if there is only one tube 3350. The tubes 3350 may be formed with a sufficient structural stiffness to resist crushing or may be as described in U.S. Pat. No. 6,044,844, the contents of which are incorporated herein by reference Each tube 3350 may be configured to receive a flow of air from the connection port 3600 on top of the patient's head and to deliver the flow of air to the seal-forming structure 3100 at the entrance of the patient's airways. In the example shown in FIG. 3Z, each tube 3350 lies in use on a path extending from the plenum chamber 3200 across the patient's cheek region and superior to the patient's ear to the elbow 3610. For example, a portion of each tube 3350 proximate the plenum chamber 3200 may overlie a maxilla region of the patient's head in use. Another portion of each tube 3350 may overlie a region of the patient's head superior to an otobasion superior of the patient's head. Each of the tubes 3350 may also lie over the patient's sphenoid bone and/or temporal bone and either or both of the patient's frontal bone and parietal bone. The elbow 3610 may be located in use over the patient's parietal bone, over the frontal bone and/or over the junction therebetween (e.g. the coronal suture).

In certain forms of the present technology the patient interface 3000 is configured such that the connection port 3600 can be positioned in a range of positions across the top of the patient's head so that the patient interface 3000 can be positioned as appropriate for the comfort or fit of an individual patient. In some examples, the headgear tubes 3350 are configured to allow movement of an upper portion of the patient interface 3000 (e.g. a connection port 3600) with respect to a lower portion of the patient interface 3000 (e.g. a plenum chamber 3200). That is, the connection port 3600 may be at least partially decoupled from the plenum chamber 3200. In this way, the seal-forming structure 3100 may form an effective seal with the patient's face irrespective of the position of the connection port 3600 (at least within a predetermined range of positions) on the patient's head.

As described above, in some examples of the present technology the patient interface 3000 comprises a seal-forming structure 3100 in the form of a cradle cushion which lies generally under the nose and seals to an inferior periphery of the nose (e.g. an under-the-nose cushion). The positioning and stabilising structure 3300, including the tubes 3350 may be structured and arranged to pull the seal-forming structure 3100 into the patient's face under the nose with a sealing force vector in a posterior and superior direction (e.g. a posterosuperior direction). A sealing force vector with a posterosuperior direction may cause the seal-forming structure 3100 to form a good seal to both the inferior periphery of the patient's nose and anterior-facing surfaces of the patient's face, for example on either side of the patient's nose and the patient's lip superior.

5.3.3.1.2 Extendable and Non-Extendable Tube Portions

In some examples of the present technology, one or both of the tubes 3350 are not extendable in length. However, in some forms, the tubes 3350 may comprise one or more extendable tube sections, for example formed by an extendable concertina structure. In some forms, the patient interface 3000 may comprise a positioning and stabilising structure 3300 including at least one gas delivery tube comprising a tube wall having an extendable concertina structure. The patient interface 3000 shown in FIG. 3Z comprises tubes 3350, the superior portions of which comprise extendable tube sections each in the form of an extendable concertina structure 3362.

The cross-sectional shape of the non-extendable tube sections 3363 of the tubes 3350 may be circular, elliptical, oval, D-shaped or a rounded rectangle, for example as described in U.S. Pat. No. 6,044,844. A cross-sectional shape that presents a flattened surface of tube on the side that faces and contacts the patient's face or other part of the head may be more comfortable to wear than, for example a tube with a circular cross-section.

In some examples of the present technology, the non-extendable tube sections 3363 connects to the plenum chamber 3200 from a low angle. The headgear tubes 3350 may extend inferiorly down the sides of the patient's head and then curve anteriorly and medially to connect to the plenum chamber 3200 in front of the patient's face. The tubes 3350, before connecting to the plenum chamber 3200, may extend to a location at the same vertical position as (or, in some examples, inferior to) the connection with the plenum chamber 3200. That is, the tubes 3350 may project in an at least partially superior direction before connecting with the plenum chamber 3200. A portion of the tubes 3350 may be located inferior to the cushion module 3150 and/or the seal forming structure 3100. The tubes 3350 may contact the patient's face below the patient's cheekbones, which may be more comfortable than contact on the patient's cheekbones and may avoid excessively obscuring the patient's peripheral vision.

5.3.3.1.3 Conduit Headgear Connection Port

In certain forms of the present technology, the patient interface 3000 may comprise a connection port 3600 located proximal to a superior, lateral or posterior portion of a patient's head. For example, in the form of the present technology illustrated in FIG. 3Z, the connection port 3600 is located on top of the patient's head (e.g. at a superior location with respect to the patient's head). In this example the patient interface 3000 comprises an elbow 3610 forming the connection port 3600. The elbow 3610 may be configured to fluidly connect with a conduit of an air circuit 4170. The elbow 3610 may be configured to swivel with respect to the positioning and stabilising structure 3300 to at least partially decouple the conduit from the positioning and stabilising structure 3300. In some examples the elbow 3610 may be configured to swivel by rotation about a substantially vertical axis and, in some particular examples, by rotation about two or more axes. In some examples the elbow may comprise or be connected to the tubes 3350 by a ball-and-socket joint. The connection port 3600 may be located in the sagittal plane of the patient's head in use.

Patient interfaces having a connection port that is not positioned anterior to the patient's face may be advantageous as some patients may find a conduit that connects to a patient interface anterior to their face to be unsightly and/or obtrusive. For example, a conduit connecting to a patient interface anterior to the patient's face may be prone to interference with bedclothes or bed linen, particularly if the conduit extends inferiorly from the patient interface in use. Forms of the present technology comprising a patient interface having a connection port positioned superiorly to the patient's head in use may make it easier or more comfortable for a patient to lie or sleep in one or more of the following positions: a side-sleeping position, a supine position (e.g. on their back, facing generally upwards) or in a prone position (e.g. on their front, facing generally downwards). Moreover, connecting a conduit to an anterior portion of a patient interface may exacerbate a problem known as tube drag in which the conduit exerts an undesired force upon the patient interface during movement of the patient's head or the conduit, thereby causing dislodgement away from the face. Tube drag may be less of a problem when force is received at a superior location of the patient's head than anterior to the patient's face proximate to the seal-forming structure (where tube drag forces may be more likely to disrupt the seal).

5.3.3.1.4 Headgear Tube Fluid Connections

The two tubes 3350 are fluidly connected at their inferior ends to the plenum chamber 3200. In certain forms of the technology, the connection between the tubes 3350 and the plenum chamber 3200 is achieved by connection of two rigid connectors. The tubes 3350 and plenum chamber 3200 may be configured to enable the patient to easily connect the two components together in a reliable manner. The tubes 3350 and plenum chamber 3200 may be configured to provide tactile and/or audible feedback in the form of a 're-assuring click' or a similar sound, so that the patient may easily know that each tube 3350 has been correctly connected to the plenum chamber 3200. In one form, the tubes 3350 are formed from a silicone or textile material and the inferior end of each of the silicone tubes 3350 is overmolded to a rigid connector made, for example, from polypropylene, polycarbonate, nylon or the like. The rigid connector on each tube 3350 may comprise a female mating feature configured to connect with a male mating feature on the plenum chamber 3200. Alternatively, the rigid connector on each tube 3350 may comprise a male mating feature configured to connect to a female mating feature on the plenum chamber 3200. In other examples the tubes 3350 may each comprise a male or female connector formed from a flexible material, such as silicone or TPE, for example the same material from which the tubes 3350 are formed.

In other examples a compression seal is used to connect each tube 3350 to the plenum chamber 3200. For example, a resiliently flexible (e.g. silicone) tube 3350 without a rigid connector may be configured to be squeezed to reduce its diameter so that it can be compressed into a port in the plenum chamber 3200 and the inherent resilience of the silicone pushes the tube 3350 outwards to seal the tube 3350 in the port in an air-tight manner. Alternatively, in a hardto-hard type engagement between the tube 3350 and the plenum chamber 3200, each tube 3350 and/or plenum chamber 3200 may comprise a pressure activated seal, for example a peripheral sealing flange. When pressurised gas is supplied through the tubes 3350 the sealing flange may be urged against the join between the tubes and a circumferential surface around a port or connector of the plenum chamber 3200 to form or enhance a seal between the tube 3350 and plenum chamber 3200.

5.3.3.1.5 Conduit Headgear Straps

In certain forms of the present technology, the positioning and stabilising structure 3300 comprises at least one headgear strap acting in addition to the tubes 3350 to position and stabilise the seal-forming structure 3100 at the entrance to the patient's airways. As shown in FIG. 3Z, the patient interface 3000 comprises a strap 3310 forming part of the positioning and stabilising structure 3300. The strap 3310 may be known as a back strap or a rear headgear strap, for example. In other examples of the present technology, one or more further straps may be provided. For example, patient interfaces 3000 according to examples of the present technology having a full face cushion may have a second, lower, strap configured to lie against the patient's head proximate the patient's neck and/or against posterior surfaces of the patient's neck.

In the example shown in FIG. 3Z, strap 3310 of the positioning and stabilising structure 3300 is connected between the two tubes 3350 positioned on each side of the patient's head and passing around the back of the patient's head, for example overlying or lying inferior to the occipital bone of the patient's head in use. The strap 3310 connects to each tube above the patient's ears. With reference to FIG. 3Z, the positioning and stabilising structure 3300 comprises a pair of tabs 3320. In use a strap 3310 may be connected between the tabs 3320. The strap 3310 may be sufficiently flexible to pass around the back of the patient's head and lie comfortably against the patient's head, even when under tension in use.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

In certain forms of the technology the vent 3400 is provided by one or more components assembled together in a vent structure 3410.

In certain forms of the technology, for example as shown in many of FIGS. 8A to 13G, the vent structure 3410 comprises a vent housing 3411 and a membrane 3412. The vent structure 3410 may also comprise a diffuser 3429. These components of the vent structure 3410 will now be described.

5.3.4.1 Vent Housing

In certain forms, the vent housing 3411 may define a first flow path between a first port 3413 and a second port 3414. The first port 3413 may be configured to connect in use to the air circuit 4170. The second port 3414 may be configured to connect in use to the plenum chamber 3200. In some forms, the connection of the first port 3413 to the air circuit 4170, and/or the connection of the second port 3414 to the plenum chamber 3200, may be a direct connection. That is, the vent structure 3410 may be located directly between the plenum chamber 3200 and the air circuit 4170, as shown in the form of FIGS. 11A-11C. In other forms, the connection of the first port 3413 to the air circuit 4170, and/or the connection of the second port 3414 to the plenum chamber 3200, may be an indirect connection. Where there is an indirect connection, there may be one or more other components between the respective port and the air circuit 4170 and/or plenum chamber 3200. It should be appreciated that, unless otherwise stated, the nature of the connection being referred to is a fluid connection. The components may additionally be mechanical connected.

The vent housing 3411 may also define a second flow path between the first flow path and surrounding ambient air.

The vent housing 3411 may also be configured to define a second flow path between the first flow path and the surrounding ambient air.

In some forms of the technology, such as shown in FIGS. 8B to 8L and 9A to 9D, the vent housing 3411 may be configured so that the vent structure 3410 is substantially tubular in shape. In the forms shown in FIGS. 8B to 8L, 9A to 9D and 10A to 10G, the tubular shape of the vent structure 3410 has a circular cross-section. In other forms, the cross-sectional shape of the tube may be an alternative shape, for instance rectangular, square or triangular.

In the form of the technology shown in FIGS. 13A to 13G, the vent housing 3411 is configured so that the vent structure 3410 is generally a T-shaped tubular structure.

5.3.4.1.1 Tube Portions

In some forms of the technology, such as those shown in FIGS. 8B to 8L, 9A to 9D, 10A to 10G and 13A to 13G, the vent housing 3411 comprises a first tube portion 3421 configured to fluidly connect to the plenum chamber 3200 through a direct or indirect mechanical connection. The first tube portion 3421 may form the second port 3414. The first tube portion 3421 may form part of the first flow path.

In these forms, the first tube portion 3421 may comprise a first flange 3422. The first flange 3422 may extend radially outward from the body of the first tube portion 3421 (and outward from the first flow path inside the first tube portion) at an end of the first tube portion 3421 distal from the second port 3414. That is, the first tube portion 3421 may have the second port 3414 and the first flange 3422 located at opposite ends of the first tube portion 3421.

In these forms of the technology, the vent housing 3411 may further comprise a second tube portion 3427. The second tube portion 3427 may form the first port 3413 and is configured to fluidly connect to the air circuit 4170 through a direct or indirect mechanical connection. The second tube portion may also form part of the first flow path together with the first tube portion.

The second tube portion 3427 may be configured to mechanically and fluidly connect to the first tube portion 3421 at an opposite end to the end that connects to the air circuit 4170. The second tube portion 3427 may comprise a second flange 3431 that extends radially outward from the body of the second tube portion 3427 (and outward from the first flow path inside the second tube portion) at an end of the second tube portion 3427 distal to the first port 3413. The first flange 3422 may be connected to the second flange 3431 to achieve the connection between the first and second tube portions.

The first and second tube portions may be configured so that the second flow path is formed between the first tube portion 3421 and the second tube portion 3427 in the region in which the two tube portions connect together. For example, the second flow path may be formed between the first flange 3422 and the second flange 3431. As shown in FIG. 8D, the outer perimeter of the first flange 3422 may be connected to the outer perimeter of the second flange 3431 while radially inner portions of the respective flanges are separated by a gap such that the second flow path is formed between the first 3422 and second 3431 flanges.

In some forms, the second flow path forms an annular volume extending radially outward from the first flow path all the way around the outer circumference of the first flow path. In other forms, the first and second tube portions may be configured so that the second flow path is made up of one or more channels extending radially outwardly from the first flow path in a variety of regions around the outer circumference of the first flow path. In such forms, the first and second tube portions may abut at one or more locations around the outer circumference of the first flow path to create gaps in between these locations that create the second flow path channels. The first and/or second tube portions may comprise protrusions at a variety of places around their circumference to achieve these abutments. The channels may be distributed around the circumference of the first flow path, for example evenly distributed.

In some forms, the first flange 3422 and the second flange 3431 may be connected, for example through a mechanical connection (e.g. a snap-fit connection) or using an adhesive. In other forms, such as that shown in FIGS. 10A to 10C, the first flange 3422 and the second flange 3431 may be integrally formed such that the first 3421 and second 3427 tube portions are also integrally formed. For example, the vent housing 3411, including the first and second tube portions, may be a single moulded component.

In some forms of the technology, such as that shown in FIGS. 8B-8L and FIGS. 9A to 9D, the first and second tube portions are arranged such that the longitudinal axes of the first tube portion 3421 and the second tube portion 3427 are aligned. In the form of the technology shown in FIGS. 13A to 13G, the first and second tube portions are arranged such that there is a non-zero angle between the longitudinal axes of the first tube portion 3421 and the second tube portion 3427. For example, in the form shown in FIGS. 13A to 13G, the angle between the longitudinal axes of the first tube portion 3421 and the second tube portion 3427 is approximately perpendicular. In the form of the technology shown in FIGS. 10A to 10G, the second tube portion 3427 comprises a bend.

In some forms, for example as shown in FIGS. 13A to 13G, the vent structure 3410 may be configured to connect to the positioning and stabilising structure 3300 where the positioning and stabilising structure 3300 comprises one or more headgear tubes 3350 that deliver pressurised air received from a conduit forming part of the air circuit 4170 from the RPT device to the patient's airways. In such forms, the vent housing 3411 may also further comprise a third tube portion 3428. The third tube portion 3428 may be fluidly and mechanically connected to the first tube portion 3421 in a similar way to the second tube portion 3427, and the above description of the second tube portion 3427 may also generally apply to the third tube portion. For example, the third tube portion 3428 may also comprise a first port 3413 (i.e. the vent structure 3410 may comprise two first ports in this configuration). The second and third tube portions may also be fluidly and mechanically connected to each other.

In forms of the technology in which the vent structure 3410 comprises first, second and third tube sections, the first tube portion may be generally centrally positioned between the second and third tube portions, which extend outwardly from the first tube portion, for example in a symmetric arrangement. In the form of the technology shown in FIGS. 13A to 13G, the vent structure 3410 is generally T-shaped with the second and third tube portions forming the arms of the 'T' and the first tube portion forming the trunk. For example, the second tube portion 3427 and the third tube portion 3428 may be oriented with their longitudinal axes aligned with each other and each perpendicular to the longitudinal axis of the first tube portion 3421.

The second tube portion 3427 and third tube portion 3428 may be each configured to connect to a respective tube 3350 of a positioning and stabilising structure 3300. The second tube portion 3427 and third tube portion 3428 may be each configured to connect to tubes 3350 via any suitable mechanical connection.

5.3.4.1.2 Retaining Member

As already mentioned, and as will be described in more detail later, the vent structure 3410 comprises a membrane 3412. The membrane 3412 is retained within the vent housing 3411. The retention mechanism may take different forms in different forms of the technology.

In the form of the technology shown in FIGS. 8B to 8L and 9A to 9D, the membrane 3412 is retained by a radially outer region of the membrane 3412 being friction fit between two parts of the vent housing. For examples, as shown in FIGS. 8F and 8G, the membrane 3412 may be sandwiched between the first tube portion 3421 and the second tube portion 3427, for example between the first flange 3422 and the second flange 3431. The parts of the tube portion(s) that retain the membrane may be referred to as retaining members.

FIGS. 13A to 13G shown another way of retaining the membrane 3412. In the form shown in these figures, the vent housing 3411 comprises a retaining member 3424 that keeps the membrane 3412 in place within the vent housing 3411 but the membrane 3412 is not fixedly attached to the vent housing 3411. The retaining member 3424 nevertheless may assist in keeping the membrane 3412 located in the appropriate position of the vent housing 3411 and may prevent the membrane 3412 falling out of place as the vent structure 3410 is moved or placed in different positions. In some forms, the retaining member 3424 may engage with an inner circumference of membrane 3412. For example, the retaining member 3424 may engage the central aperture 3415 of the membrane 3412. The retaining member 3424 may retain the membrane 3412 such that it does not move in a radial direction relative to the first tube portion 3421. In the form shown in FIGS. 13A to 13G, the retaining member 3424 is in the form of a ring-shape structure extending outwardly from the inner surface of the first tube portion 3421 at the same end as the first flange 3422 in a direction parallel to the longitudinal axis of the first tube portion. The retaining member 3424 may extend into the first flow path in the second and third tube portions. An outer edge of the ring-shaped retaining member may comprise one or more extensions that extend in a radially outward direction over at least a portion of the first side 3416 of the membrane 3412 adjacent the central aperture 3415. The extensions of the retaining member 3424 may engage the central aperture 3415. In the form of the technology, the retaining member 3424 comprises four extensions spaced equidistantly around the ring-shape portion. In other forms of the technology, the retaining member 3424 may have an alternative shape and/or structure, for instance it may be in the form of a tube-like structure.

In other forms, the membrane may be retained using a different structure of components, i.e. retaining members. In one form, an array of elongate retaining members are provided inside the first and/or second tube portions to form a cage (or cage-like structure) within which the membrane 3412 is housed. The cage confines the membrane 3412 while allowing the flow of air between the retaining members in order to act on the sides of the membrane 3412. Other retaining mechanisms may be provided in other forms of the technology.

5.3.4.1.3 Vent Holes

The vent housing 3411 may also define a plurality of vent holes 3418. The vent holes 3418 may form part of the second flow path and allow gas in the vent 3400 to exit to the surrounding ambient air.

The vent holes 3418 may be provided in an outer wall of the first tube portion 3421 and/or the second tube portion 3427 and/or the third tube portion 3428 (if present). For example, the vent holes may be formed from gaps between these components. The vent holes 3418 may be positioned circumferentially around the vent structure 3410. The vent holes 3418 may be spaced equidistantly apart.

In some forms of the technology, as shown in FIGS. 8B to 8L and 13A to 13G, the first flange 3422 comprises the plurality of vent holes 3418. The vent holes 3418 may be substantially arc-shaped when projected on to a plane in some forms, while in other forms they may have another shape, for instance circular, rectangular, or square. The vent holes 3418 may be positioned circumferentially around the first flange 3422. The vent holes 3418 may be spaced equidistantly apart.

Where the vent holes 3418 are located in the first flange 3422, the vent holes may act to project the venting gas flow in a direction approximately parallel with the longitudinal axis of the first tube portion 3421, which may additionally, or alternatively, be parallel to the outer walls of the first tube portion 3421. Depending on where the vent 3400 is located in the respiratory therapy system, this may be desirable in order to avoid venting gases being directed towards the patient's face, which may cause discomfort, or towards items against which the vent flow may flow, creating noise.

In some forms of the technology, such as that shown in FIG. 8L, the first tube portion 3421 comprises a plurality of tube passive vent holes 3426. The tube passive vent holes 3426 are configured to allow air to flow directly from the first flow path to the surrounding ambient air, i.e. bypassing the second flow path. The plurality of tube passive vent holes 3426 may be located in an annular region of the first tube portion 3421. The plurality of tube passive vent holes 3426 may be substantially circular in cross-sectional shape, while in other forms they may have another cross-sectional shape, for instance rectangular, or square. In some forms, the tube passive vent holes 3426 are arc-shaped, being elongated around the cross-sectional circumference of the first tube portion 3421. The plurality of tube passive vent holes 3426 may be spaced equidistantly apart. The tube passive vent holes 3426 may be distributed circumferentially around the first tube portion 3421. The tube passive vent holes 3426 may align with the diffuser 3429, described below, such that the air flow exiting the tube passive vent holes 3426 flows into the diffuser material. The function of the tube passive vent holes 3426 is explained below.

One form of vent 3400 in accordance with the present technology comprises a plurality of holes, for example, about 4 to 20 holes.

The vent holes may be positioned adjacent an outer perimeter of the membrane 3412.

5.3.4.2 Membrane

The membrane 3412 may be in the form of a thin sheet. In some forms, as shown in many of FIGS. 8B to 13G, the membrane 3412 is planar or flat. The first 3416 and second 3417 sides of the membrane 3412 may be planar surfaces of the membrane 3412 when the membrane is at rest, i.e. no forces are acting upon the membrane that distorts its shape. In other forms, the membrane may have a curvature at rest, although the membrane may still be generally flat, i.e. not curved to a significant degree.

The membrane 3412, as shown in many of FIGS. 8B to 13G, may be circular in shape when projected onto a plane, in other forms, the membrane 3412 may have an alternative shape for instance oval, square (with or without rounded corners), or rectangular (with or without rounded corners). The central aperture 3415, as shown in many of FIGS. 8B to 13G, may be circular in shape, in other forms it may be oval, square (with or without rounded corners), or rectangular (with or without rounded corners). In certain forms, the central aperture 3415 is the same shape as the outer perimeter of the membrane 3412. The central aperture 3415 may extend through the membrane 3412 from the first side 3416 of the membrane to the second side 3417 of the membrane. In some forms the central aperture 3415 may have a shape such that the membrane 3412 has an inner perimeter with one or more of the shapes of the protrusions 3419 as described below. In some forms, as shown in many of FIGS. 8A to 13G, the membrane 3412 may be substantially annular in shape, i.e. the membrane 3412 may be a planar sheet with a circular outer perimeter and a the central aperture 3415 may be circular, both having the same central axis (i.e. being concentric). The membrane 3412 may be described as ring-shaped or disc-shaped.

In some forms, the membrane 3412 may be configured such that it is flexible and resilient. These properties may be achieved by a combination of the choice of material of the membrane 3412 and the shape and/or structure of the membrane 3412. In forms where the membrane 3412 is planar or flat, the membrane may be flexible or able to deflect in a direction perpendicular to that of the plane or in a normal direction, as shown in FIGS. 8F and 8G. The membrane 3412 may be resilient such that a force acting on the membrane 3412 may deflect or flex the membrane 3412 and when the force is removed the membrane 3412 returns to a neutral or rest position. The neutral or rest position of the membrane 3412 may be when it is substantially planar, as shown in FIG. 8D. In other forms, the membrane 3412 may be configured such that it is substantially inflexible. In some forms, as shown in FIGS. 13F and 13G, the membrane 3412 does not flex or change shape when acted on by the force of the flow of air through the first flow path. Again, this property may be achieved by a combination of the choice of material of the membrane 3412 and the shape and/or structure of the membrane 3412. In some forms the membrane 3412 may be formed from silicone. In other forms, the membrane 3412 may be formed from a polycarbonate or some other suitable material.

In some forms of the technology, as shown in FIGS. 8J, 8K, 8L, and 12, the membrane 3412 may comprise a plurality of membrane passive vent holes 3425. The membrane passive vent holes 3425 may be configured to allow air to flow through the membrane 3412. In use, the flow of air from the membrane passive vent holes 3425 flows from the first flow path to the second flow path and through the vent holes 3418 to the surrounding ambient air. The membrane passive vent holes 3425, if present, may allow for a minimum flow of air to exit the vent structure 3410 when the membrane 3412 is in any configuration, i.e. including both the first and second configurations mentioned elsewhere in this specification. The passive vent holes 3425 may be used to give a constant flow-pressure curve such that the vent 3400 can function as a constant flow vent as discussed below. The membrane passive vent holes 3425 may be circular in shape when projected onto a plane. In other forms they may be another shape, for instance rectangular, square, triangular or arc-shaped. The membrane passive vent holes 3425 may be spaced equidistantly apart. The membrane passive vent holes 3425 may be distributed circumferentially around the membrane 3412.

The membrane 3412 may be positioned within the vent housing 3411 and is generally positioned in a region between the first tube portion 3421 and the second tube portion 3427 (and, if the third tube portion 3428 is present, between the first tube portion 3421 and the third tube portion 3428). The membrane 3412 may be located concentrically with respect to the longitudinal axis of the first tube portion 3421. In use, air passes through the central aperture 3415 of the membrane 3412 and the central aperture 3415 forms part of the first flow path. A flow of air may pass through the central aperture 3415 in use both when the patient 1000 is inhaling and exhaling. The membrane 3412 may be positioned in the vent housing 3411 such that the first side 3416 of the membrane 3412 and the second side 3417 of the membrane 3412 (opposite the first side 3416) are both exposed to air flow in the first flow path in use. This allows the pressure of air in the first flow path to act on both sides of the membrane 3412, which allows the membrane to move as described below. In certain forms of the technology, for example those illustrated in FIGS. 8B to 13G, in use, a flow of air from the air circuit 4170 may flow into the first side 3416 while a flow of air when the patient 1000 is exhaling may flow into the second side 3417.

In some forms of the technology, such as those shown in FIGS. 8A to 10G, the membrane 3412 may be fixed to the vent housing 3411. For example, a radially outer portion around the outer circumference of the membrane may be fixed to the vent housing 3411, for example, to the first tube portion 3421, for example to the first flange 3422, or sandwiched between parts of the first and second tube portions, for example between parts of the first and second flanges. In some forms of the technology, the membrane 3412 may be fixed to the vent housing 3411 by a mechanical connection, such as a friction fit connection, or an adhesive, while in other forms it may be overmoulded. In still other forms, the membrane 3412 may be fixed using another suitable attachment mechanism.

When assembled in the vent structure, the membrane 3412 may be positioned adjacent to the first flange 3422. The membrane 3412 may also be positioned such that it is substantially parallel to the first flange 3422, i.e. so that a plane of the membrane 3412 is parallel to a plane of the first flange 3422. The membrane 3412 may be positioned around the entire inner circumference of the first flange 3422. As shown in FIG. 8G, for example, a gap 3423 between the first side 3416 of the membrane 3412 and the first flange 3422 may form a part of the second flow path. In one configuration of the membrane 3412, the membrane may be positioned such that it at least partially blocks the gap 3423. The height of the gap 3423 may vary as the membrane 3412 moves, as will be described below.

In some forms of the technology, such as that shown in FIGS. 13A to 13G, the membrane 3412 is loosely contained within the vent housing 3411. The membrane 3412 may not be fixedly connected to a part of the vent housing 3411 or any other part of the vent structure 3410. The membrane 3412 may be constrained by the vent housing 3411 to limit its movement, for example it may be constrained such that it cannot move relative to the vent housing 3411 in a direction substantially parallel to the planar surface of the membrane 3412. The membrane 3412 may be able to translate in a direction substantially perpendicular to the planar surface of the membrane 3412, although the amount of movement in this direction may be limited by the vent housing 3411, for example by retaining member 3424, so that the membrane's movement is constrained. In such forms, the vent structure 3410 may be configured such that the entire membrane 3412 may be displaced away from the second port 3414 when air flows in the first flow path from the second port 3414 to the first port to allow the air to flow from the first flow path to the second flow path. The entire membrane 3412 may be displaced in a direction towards the second port 3414 when air flows in the first flow path from the first port 3413 to the second port 3414 to at least partially block air flow from the first flow path to the second flow path. The membrane 3412 being separate (i.e. not fixedly attached) to the vent housing 3411 may provide the advantage of making the vent structure 3410 easier to manufacture compared to forms of the technology where the membrane 3412 is connected to the vent housing 3411.

5.3.4.2.1 Alternative Membrane Shapes

Some exemplary shapes of membrane have already been described. FIG. 12 shows a number of further exemplary membrane shapes that may be used in some alternative forms of the technology. In some forms, the exemplary membranes 3412 may improve the effectiveness of the vent structure 3410.

The membrane 3412 may comprise one or more protrusions 3419 extending from an inner perimeter of the membrane 3412 towards the centre of the central aperture 3415 in the central region of the membrane 3412.

The presence of protrusions 3419 of the membrane 3412 into the central aperture 3415, and the shape and extent (e.g. area) of those protrusions 3419 may alter the resistance to the flow of air through the central aperture 3415. Altering the resistance to the flow of air through the central aperture 3415 may alter the way in which the membrane 3412 moves in response to changes in air flow inside the vent structure 3410 and therefore may alter the operation of the vent structure 3410. Alterations of the shape, number, and/or size of the protrusions 3419 may be used to tune the vent structure 3410 to operate in the desired manner. More particularly, altering the resistance to the flow of air through the central aperture 3415 will also alter the amount of deflection of the membrane 3412 and therefore the position of the membrane 3412 in the second configuration (see discussion below). The amount of air that flows through the second flow path and is therefore vented by the vent structure 3410 at different pressures within the respiratory system can therefore also be controlled.

In some forms, such as shown in the top left diagram of FIG. 12, the membrane 3412 comprises protrusions 3419 each having a substantially rectangular shape when projected onto a plane. For example, in the exemplary form shown in FIG. 12, there are two such protrusions, each extending towards each other from diametrically opposite regions of the inner circumference of the ring-shaped body of the membrane 3412. The protrusions may be configured with substantially parallel sides.

In other forms, such as shown in the top right diagram of FIG. 12, the membrane 3412 may comprise a plurality of protrusions 3419 each having a substantially arrow shape when projected onto a plane. For example, in the exemplary form shown in FIG. 12, there are four such arrow-shaped regions of the membrane, each projecting from four regions of the inner circumference distributed evenly around the ring-shaped main body of the membrane 3412. The arrow-shaped regions may be shaped to point towards the centre of the aperture in the membrane. In alternative forms, another number of protrusions may be present.

In other forms, such as shown in the bottom right diagram of FIG. 12, the membrane 3412 comprises a single protrusion 3419 that extends across the central aperture 3415 to form a band. The band may pass symmetrically across the central aperture 3415.

In yet other forms, the protrusions 3419 may be of a different shape such as triangular, circular or square.

In these forms, the thinner and longer the protrusions 3419, the more flexible the protrusions 3419 are, and the easier they deflect in response to changes in air flow and/or pressure against them.

In some forms, such as shown in the bottom left diagram of FIG. 12, the protrusions 3419 are formed by one or more slits located around the inner circumference of the membrane 3412. The protrusions 3419 are the radially inner regions of the member 3412 located between the protrusions 3419. The membrane 3412 may comprise a plurality of slits that are spaced equidistantly around the perimeter of the central aperture 3415. In some forms, the membrane 3412 comprises five slits spaced equidistantly around the inner circumference. In other forms, the membrane may comprise a different number of slits and/or the slits may be spaced non-evenly around the inner circumference. In this form, the longer the slits, the more flexible the protrusions 3419 are, and the easier they deflect in response to changes in air flow and/or pressure against them.

5.3.4.3 Operation of the Vent Structure

The vent structure 3410 is configured so that the membrane 3412 is able to move or flex based on the flow and/or pressure of air acting on its two sides. For example, as has been explained, in some forms, the membrane 3412 may be flexible and therefore some parts of the membrane may be able to move relative to other components in the vent structure 3410. In other forms, the vent structure 3410 may be configured so that the membrane 3412 may be able to move position (i.e. be displaced) relative to other components in the vent structure 3410. In some forms, the membrane 3412 may be flexible and be able to move position.

Consequently, the membrane 3412 may be able to adopt at least two configurations where the position and/or shape of the membrane differs between the two configurations. The membrane 3412 may also be able to adopt other configurations and, in some forms, the membrane 3412 can adopt a continuum of configurations.

In use, the membrane 3412 or a portion of the membrane, for example a radially inner portion, may deflect or move based on the flow of air against and/or the action of air pressure on the membrane 3412. This deflection or movement may cause the flow of air through the second flow path to alter between two configurations of the membrane 3412. For example, a radially inner portion of the membrane 3412 may be configured to deflect in a direction away from the second port 3414 when air flows in the first flow path from the second port 3414 to the first port 3413. Based on the positioning of the membrane 3412 within the vent structure, this deflection may cause the second flow path to be unblocked, or to reduce the amount of blocking of the second flow path, allowing air to flow from the first flow path to the second flow path. The inner portion of the membrane 3412 may be configured to deflect in a direction towards the second port 3414 when air flows in the first flow path from the first port 3413 to the second port. Based on the positioning of the membrane 3412 within the vent structure, this deflection may at least partially block air flow from the first flow path to the second flow path. The inner portion of the membrane may be a region of the membrane surrounding the central aperture 3415.

The vent structure 3410 may be configured such that, in use, when air flows in the first flow path from the first port 3413 to the second port 3414, the membrane 3412 adopts a first configuration to at least partially block air flow from the first flow path to the second flow path. This adoption of the first configuration may be caused by the action of the air flow in the first flow path on the membrane, for example on one side of the membrane. The vent structure 3410 may further be configured such that, in use, when air flows in the first flow path from the second port 3414 to the first port 3413, the membrane 3412 adopts a second configuration to allow air flow from the first flow path to the second flow path. This adoption of the second configuration may be caused by the action of the air flow in the first flow path on the membrane, for example on the other side of the membrane.

The vent structure 3410 may be configured such that the membrane 3412 adopts the first configuration when the patient 1000 is inhaling such that the majority of the pressurised flow of air from the RPT device 4000 supplied through the air circuit 4170 passes through the central aperture 3415 and towards the patient and does not exit the vent structure 3410. The vent structure 3410 may be configured such that the membrane 3412 adopts the second configuration when the patient is exhaling such that at least a portion of the flow of air exhaled by the patient may exit the vent structure 3410 into the surrounding ambient air.

Operation of the vent structure 3410 as shown in FIGS. 8C to 8K, is shown in FIG. 8F, which shows the vent structure 3410 during inhalation, and FIG. 8G, which shows the vent structure 3410 during exhalation. During inhalation the membrane 3412 is in the first configuration and the flow of pressurised air from the air circuit 4170 flows through the vent structure 3410 from the first port 3413 to the second port 3414. Some of the air flows through the central aperture 3415 of the membrane 3412 and to the second port 3414 (and then on towards the patient 1000) while some flows into the first side 3416 of the membrane 3412. A force moves part of the flexible membrane 3412 (in the illustrated example, a radially inner region of the membrane) in a direction towards the first tube portion 3421. This deflection of the membrane 3412 at least partially, and in some examples fully (e.g. when the second side 3417 of the membrane contacts the end of the first tube portion 3421 distal from the second port 3414), blocks the second flow path. This therefore reduces or prevents air flowing from the first flow path out through the vent holes 3418 and means that there is a decreased, or in some examples no, flow of air through the vent 3400 during inhalation. During exhalation the membrane 3412 adopts the second configuration. This is because the flow of air from the patient entering into the vent structure through second port 3414 flow into the second side 3417 of the membrane 3412, providing a force to move the part of flexible membrane 3412 in a direction towards the second tube portion 3427. This deflection of the membrane 3412 moves the membrane out of contact with the end of the first tube portion 3421 and allows air to flow along the second flow path between the first tube portion and the membrane and to vent through the vent holes 3418. In some forms, the exhaled flow of air may be sufficient to fully open the second flow path.

Operation of the vent structure shown in FIGS. 9A to 9D is similar to that described above. FIG. 9C shows the vent structure 3410 during inhalation and FIG. 9D shows the vent structure 3410 during exhalation. During inhalation the pressure P3 in the first tube portion 3421 in a region adjacent the second flow path and the second side 3417 of the membrane, is lower than pressure P1 in the second tube portion 3427 in a region adjacent the first side 3416 of the membrane, as the flow has to change direction to flow through the vent holes 3418. The region of P3 is also partially shielded by an internal wall of the vent housing 3411 and the membrane 3412. The pressure difference between P1 and P3 deflects the membrane 3412 towards the vent holes 3418 to restrict the flow of air through the vent holes 3418 to the surrounding ambient air. During exhalation, the pressure P5 in a region inside the second tube portion 3427 in a region adjacent the first side 3416 of the membrane, downstream of the membrane 3412, is lower than the pressure P6 in a region inside the first tube portion 3421 in a region adjacent the second side 3417 of the membrane, upstream of the membrane 3412, due to the P5 region being partially shielded by the internal walls of the vent housing 3411 and the membrane 3412. The pressure difference between P5 and P6 deflects the membrane 3412 away from the vent holes 3418 to allow more airflow through the vent outlets to the atmosphere.

Operation of the vent structure shown in FIGS. 13A to 13G is similar to that described above, however the membrane 3412 does not deflect or flex when under pressure from the flow of air but instead displaces (which may alternatively be referred to as translates) position to alter the degree of blocking/openness of the second flow path and to control the flow of air through the second flow path. FIG. 13F shows the vent structure 3410 during inhalation and FIG. 13G shows the vent structure during exhalation.

5.3.4.4 Diffuser

The vent structure 3410 may further comprise a diffuser 3429 configured to diffuse the flow of air exiting the vent structure 3410. The diffuser 3429 may comprise a diffuser cover 3430 which houses the diffuser 3429 and holds the diffuser in position relative to the rest of the vent structure 3410. The diffuser may help to reduce the force of air directed towards a patient's face, which may cause discomfort, and may reduce noise produced by the vent 3400.

In some forms of the technology, as shown in FIGS. 8B-8L and 10D-10G, the diffuser 3429 may be located around an outside surface of the first tube portion 3421. Alternatively, the diffuser may be located around an outside surface of the second tube portion 3427. The diffuser 3429 may be located relative to the vent holes so that the diffuser 3429 is in the path of the flow of air exiting the vent structure 3410 through the vent holes 3418, such as is shown in FIGS. 8C to 8L. For example, the diffuser 3429 may be located in a region that the vent holes 3418 are directed towards. In certain forms, the diffuser 3429 may be substantially annular in shape with the inner surface located adjacent the outer surface of the first tube portion 3421.

The diffuser cover 3430 may be a similarly annular-shaped member extending around the outer periphery of the first tube portion 3421. The diffuser cover 3430 may take the form of a shell having an internal volume configured to house the diffuser 3429. Alternatively, the diffuser cover 3430 may comprise one or more protrusions or clips configured to hold the diffuser 3429 in position relative to the rest of the vent structure 3410.

The diffuser 3429 may be offset from an exit of the second flow path, i.e. the diffuser 3429 may be located such that there is an air gap between the vent holes 3418 and the diffuser 3429. This air gap may help to reduce the level of noise created by the vent 3400. In some forms, the diffuser 3429 may be located between the plenum chamber 3200 of the patient interface 3000 and the vent holes 3418.

In some forms of the technology, as shown in FIG. 8L, the plurality of tube passive vent holes 3426 are located in the region of the first tube portion 3421 adjacent the diffuser 3429 such that the air flowing out of the first flow path through the tube passive vent holes 3426 flow through the diffuser 3429 and then to the surrounding ambient air. This ensures the vent flow through the tube passive vent holes 3426 is also diffused.

5.3.4.5 Additional Functions of the Vent Structure

As described above, the vent structure 3410 may function as a vent 3400 to allow for the washout of exhaled gases. The vent structure may also have one or more additional functions as outlined below. The various membrane parameters can be modified to alter the function of the vent structure 3410 and/or the shape of the flow curves.

5.3.4.5.1 Dual Vent Flow

The vent structure 3411 may be configured to produce two different vent flow curves at a given pressure. As shown in FIGS. 8A, 8N and 8Q, the vent flow rate during inhalation may be lower than the vent flow rate during exhalation at the same pressure. This dual vent flow provides several advantages, including reducing the amount of wasted airflow to the atmosphere during inhalation. This enables the RPT device 4000 and humidifier 5000 to be smaller and to consume less power compared to some other systems in which the vent flow rate is substantially the same during both inhalation and exhalation for a given pressure. The dual vent flow functionality of the vent structure 3411 may also allow for the use of an air circuit 4170 with a smaller diameter compared to some other systems. A further advantage is that the vent structure 3411 allows for a higher rate of vent flow during exhalation compared to some other systems, which may improve flushing out of carbon dioxide from the patient interface 3000.

5.3.4.5.2 Anti-Asphyxia Valve

In some forms the vent structure may be configured to act as an anti-asphyxia valve. In some forms, the vent housing may also comprise an anti-asphyxia valve (AAV). An AAV may be configured to allow the patient to breath from ambient through their mouth in the absence of a flow of pressurised air through the plenum chamber inlet port into the plenum chamber. An AAV may be particularly desirable to include in patient interfaces in which the seal-forming structure 3100 covers the patient's nose and mouth airways. In patient interfaces where the mouth is left uncovered, an AAV may not be necessary.

In some forms, the vent structure is configured such that the gap 3423 between the first side 3416 of the membrane 3412 and the first flange 3422 is sized to allow air to flow through the second flow path when the pressure in the first flow path drops below a threshold pressure to allow for adequate carbon dioxide washout in use.

In other forms of the technology, such as that shown in FIGS. 13A to 13G, the vent structure 3410 may comprise a separate AAV, i.e. an assembly of components acting together as an AAV. An AAV aperture 3433 may be located within the vent housing 3411, for example in a portion of the second tube portion 3427 and/or third tube portion 3428. In the example of FIGS. 13A to 13G, the AAV aperture 3433 is located in a wall of the second and third tube portions facing away from the patient when in use, i.e. opposite the first tube portion 3421. The vent structure 3410 may further comprise an AAV flap 3432 configured to move between a first configuration in which the AAV aperture 3433 is covered to block the flow of air through the AAV aperture 3433, and a second configuration in which the AAV aperture 3433 is uncovered (or partially uncovered) to block (or partially block) the flow of air through the aperture. In some forms, the AAV flap 3432 may be attached to an inner surface of a wall of the vent structure 3410, for example pivotally attached.

The AAV flap 3432 may be biased to an open configuration so that, when the therapy pressure (and therefore the pressure inside the vent structure) falls below a threshold, the AAV flap 3432 moves to uncover the AAV aperture 3433 to allow air to flow between the patient interface 3000 and atmosphere. When the therapy pressure (and therefore the pressure inside the vent structure) is above a threshold, the pressure acts on the AAV flap 3432 to urge it across the AAV aperture 3433 to block it.

In the form shown in FIGS. 13A to 13G, the AAV flap is circular in shape when projected onto a plane and comprises a planar sheet. In other forms the AAV flap may have an alternative shape, for instance square, rectangular, or oval, when projected onto a plane. The AAV aperture 3433 may be sized smaller than the AAV flap 3432 such that the AAV can fully occlude the AAV aperture 3433 when urged against it. In the form shown in FIGS. 13A to 13G, the AAV aperture is circular in shape, in other forms, it may be an alternate shape, for instance square, rectangular, or oval. The vent structure 3410 may otherwise function as described above.

5.3.4.5.3 One-Way Valve

In some forms of the technology, as shown in FIG. 8O, the vent structure 3410 may function as a one-way valve. In such forms, the vent structure 3410 is configured such that, when the membrane 3412 is in the closed configuration, there is a constant vent flow of gases out of the vent 3400. For example, the constant vent flow of gases may be zero flow. In certain forms, during inhalation by the patient 1000, the membrane 3412 may move to a configuration such that there is no air flow through the second flow path between the internal volume of the vent housing 3411 and the surrounding ambient air, i.e. there is no venting of the air during inhalation. In such forms, air may only flow through the vent holes 3418 during exhalation. This configuration may provide advantages similar to that of the dual vent flow described above.

To achieve this mode of operation, the characteristics of the vent structure 3410 are selected, or tuned, to cause the desired behaviour of the membrane 3412, in the manner explained below.

5.3.4.5.4 Constant Flow Vent

In some forms of the technology, the vent structure 3411 may function as a constant flow vent. In such a form, as shown, in FIGS. 8M and 8P, the flow of air exiting the vent 3400 may be relatively across a range of therapy pressures of air flow supplied by the RPT device 4000, i.e. for a range of pressures in the plenum chamber 3200 ("mask pressure"). This constant flow behaviour of a vent 3400 can be achieved through selection, or tuning, of the characteristics of the vent structure 3410 in order to achieve the desired flow-pressure relationship. Examples of characteristics of the vent 3400 that can be altered are discussed below.

Providing a constant flow of air exiting the vent 3400 across a range of pressures may assist in keeping the noise level of the vent reasonably constant irrespective of the therapy pressure. Providing a vent in which a constant flow rate of air exits the vent across a range of pressures may also make it easier to determine the flow of air provided to the patient 1000 compared to forms where the flow of air exiting the vent varies with pressure. For example, the amount of flow supplied to the patient may be able to be worked out by measuring the constant flow of air exiting the vent and the amount of flow provided by the RPT device 4000. This information may prove useful for operation of the respiratory system.

5.3.4.6 Tuning the Vent Structure

As mentioned above, properties or characteristics of the vent structure 3410 can be modified to alter the function of the vent structure 3410 and, in particular, the relationship between vent flow and pressure inside the vent (e.g. the therapy pressure), as shown by the shape of the flow-pressure curves.

Properties of the vent structure 3410 that may be altered to alter the operation of the vent 3400 include, but are not limited to:

properties of the membrane 3412, including the size of the central aperture 3415, the thickness of the membrane 3412, the stiffness of the membrane 3412, the number and/or size of the membrane passive vent holes 3425;

the size and shape of the first flow path and the second flow path, including the size of the gap 3423 between the first side 3416 of the membrane 3412 and the vent housing 3411, the extent of movement of the membrane 3412 permitted by the structure of the vent housing 3411 around it, the size and shape (e.g. cross-sectional area and length) of the vent holes 3418, the size and shape (e.g. cross-sectional area and length) of the first tube portion 3421, second tube portion 3427 and/or third tube portion 3428, how sinuous the first and second flow paths are, how much of the surface area of the first and second sides of the membrane 3412 is exposed to pressurised air within the vent structure, whether the vent structure 3410 includes spacers that prevent the membrane 3412 from fully closing off the second flow path, the number and/or size of the tube passive vent holes 3426.

It should be appreciated that tuning the vent structure 3410 may involve a trial and error process. That is, by altering one or more of the properties of the vent structure 3410 until the desired performance is achieved. This alteration may be performed through computer modelling and/or tests with physical prototypes.

In certain forms, the vent structure 3410 can be tuned specifically such that it can perform according to one or more of the functions as discussed above.

For example, to tune the vent structure 3410 to function as an AAV, at default or below the therapy pressure, the size of the gap 3423 between the first side 3416 of the membrane 3412 and the vent housing 3411 may be made large enough to allow for sufficient vent flow for carbon dioxide to be flushed from the mask and prevent re-breathing by the patient 1000. In some examples, the size of the gap may be in the order of magnitude of approximately 1 mm with a central aperture 3415 radius in the order of approximately 10 mm. This flow rate may allow for sufficient venting to reduce carbon dioxide rebreathing. This flow rate can be altered by modifying the membrane parameters as discussed above.

In another example, to tune the vent structure 3410 to function as a constant flow vent, the vent flow rates during therapy may be controlled by how much the membrane is allowed to deflect by modifying the membrane parameters as discussed above. An example of the vent flow of a vent structure 3410 tuned to function as a constant flow vent in the pressure range 10-25 cmH$_2$O is shown in FIG. 8P. The higher flow rate at the lower pressure of 2-4 cmH$_2$O, as shown in FIG. 8P, provides a similar function as an AAV in flushing out carbon dioxide.

In one example as shown in FIGS. 8H and 8I, a constant flow vent is achieved by having a plurality of spacers 3434 located on the first tube portion 3421 facing the first side 3416 of the membrane 3412. For example, the spacers may be protrusions provided on an end surface of the first tube portion 3421 distal from the second port 3414 and on a surface adjacent to, but spaced from, the second tube portion 3427. The spacers 3434 may be arranged to limit deflection of the membrane 3412 to prevent it completely blocking off the gap 3423 between the first tube portion 3421 and the first side 3416 of the membrane 3412. This ensures that the second flow path, and the vent holes 3418, are always at least partially open, even when the membrane is in the closed configuration. In some examples, the height of the spacers may be in the range of 0.3 mm to 1 mm. The spacers 3434 may be in the form of substantially cuboidal protrusions extending from the first tube portion 3421 in a direction towards the membrane 3412. The spacers 3434 may be located equidistantly around the end perimeter of the first tube portion 3421.

In other examples, passive vent holes may be used to give a constant flow-pressure curve. The passive vents may provide a predictable intentional leak which, when summed with the active vent flow (i.e. the vent flow that changes by virtue of the changing configuration of the membrane 3412) in the vent structure, can be tuned to suit a particular pressure-flow curve, for instance a flat or rising vent flow curve, as shown in FIG. 8M. In some examples, the passive vents may be formed as membrane passive vent holes 3425, see FIGS. 8J and 8K, as described above. The passive vents allow for a controlled predictable amount of air flow venting from the vent structure 3410. In other examples, the passive vents are formed within the first tube portion 3421, as tube passive vent holes 3426 as described above and shown in FIG. 8L. In other examples, the vent structure 3410 may comprise both membrane passive vent holes 3425 and tube passive vent holes 3426.

In examples, to tune the vent structure 3410 to function as a one-way regulated valve, the vent structure 3410 may omit the spacers described above so that the membrane is allowed to deflect to completely prevent venting of air during inhalation, as described above. This provides for zero vent flow when the patient is inhaling. The vent flow of a one-way regulated valve is shown in the graph of FIG. 8O.

5.3.4.7 Vent Structure Location

There are various places in a respiratory therapy system that the vent may be located.

For example, the vent structure may be located in the air circuit 4170 downstream of an RPT device 4000, and upstream of a patient interface 3000. In some forms of the technology, as shown in FIGS. 10A-10G, the vent structure 3410 may be located in, or provided in the form of, an elbow located between the air circuit 4170 and the patient interface 3000. In this form, the second tube portion 3427 may be a tube configured to connect to the air circuit 4170. The second tube portion 3427 may comprise a bend in the typical manner of an elbow, for example a bend through an angle in the range of approximately 0° to approximately 90°. The first tube portion 3421 may be a shorter tube configured to connect to the plenum chamber 3200. In the illustrated form, the vent holes 3418 are arranged around an outer circumference of the elbow.

Another example of the vent structure 3410 being located upstream of the patient interface 3000 is shown in FIGS. 11A to 11C. In this example, the second tube portion 3427 is a straight tube section but has a longitudinal axis at an angle (e.g. an acute angle) relative to the longitudinal axis of the first tube portion 3421. In this example, the vent structure 3410 forms the connection between the air circuit 4170 and the plenum chamber 3200.

In other forms of the technology, the vent structure 3410 may be comprised as part of the patient interface 3000, for instance the vent structure 3410 may be comprised as part of the mask or cushion. In some forms, the vent structure 3410 may be comprised as part of the plenum chamber 3200 or seal-forming structure 3100. In some forms, such as shown in FIG. 8B, the vent structure 3410 is located in the wall of the plenum chamber 3200, for example an anterior wall of the plenum chamber. In this form the vent structure 3410 is centrally located so that, when in use and the patient interface 3000 is donned by the patient, the vent structure 3410 is intersected by the mid-sagittal plane of the patient's body. The vent structure 3410 may be arranged proximate the plenum chamber inlet port, for example the vent structure 3410 may surround (e.g. encircle) the inlet port. In some forms, the second tube portion 3427 may be comprised as part of the plenum chamber 3200 that protrudes out of the body of the plenum chamber 3200 for connection of the air circuit 4170, or an elbow, thereto.

In the form shown in FIGS. 13A to 13G, the vent structure 3410 comprises two inlet tubes, i.e. second tube portion 3427 and third tube portion 3428. These tube portions are configured to respectively fluidly connect to tubes 3350 of the positioning and stabilising structure 3000 where the positioning and stabilising structure 3000 is configured to convey pressurised air to the plenum chamber 3200. In this form, the vent structure 3410 is configured to connect to a plenum chamber inlet port located in an anterior portion of the plenum chamber with the second and third tube portions extending in the lateral direction relative to the patient's body for connection to the headgear tubes 3350.

In some forms of the technology, the vent structure 3410 may be formed as part of the positioning and stabilising structure 3000, for example, the vent structure 3410 may be provided in one or more headgear tubes 3350.

5.3.5 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10 cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs, such as with processor control instructions to be executed by one or more processor(s), stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal (1 hectopascal=100 Pa=100 N/m$^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Anatomy 5.8.3.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3.2 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.4 Patient Interface

Anti-asphyxia valve (AAV): The component or sub-assembly of a mask system that, by opening to atmosphere in a failsafe manner, reduces the risk of excessive CO2 rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 REFERENCE SIGNS LIST

1000 Patient
1100 Bed partner
3000 Patient interface
3100 Seal-forming structure
3150 Cushion module
3200 Plenum chamber
3300 Positioning and stabilising structure
3301 Superior strap portion
3302 Inferior strap portion
3303 Anterior strap portion
3310 Strap
3320 Tabs
3350 Tubes
3362 Extendable concertina structure
3363 Non-extendable tube sections
3400 Vent
3410 Vent structure
3411 Vent housing
3412 Membrane
3413 First port
3414 Second port
3415 Central aperture
3416 First side of the membrane
3417 Second side of the membrane
3418 Vent holes 3419 Protrusions
3420 Inner surface of the membrane
3421 First tube portion
3422 First flange
3423 Gap
3424 Retaining member
3425 Membrane passive vent holes
3426 Tube passive vent holes
3427 Second tube portion
3428 Third tube portion
3429 Diffuser
3430 Diffuser cover
3431 Second flange
3432 AAV flap
3433 AAV aperture
3434 Spacers
3600 Connection port
3610 Elbow
3700 Forehead support
4000 RPT device
4010 External housing
4012 Upper portion
4014 Lower portion
4015 Panel(s)
4016 Chassis
4018 Handle
4020 Pneumatic block
4100 Pneumatic components
4110 Air filters
4112 Inlet air filter
4114 Outlet air filter
4120 Muffler
4122 Inlet muffler
4124 Outlet muffler
4140 Pressure generator
4142 Blower
4144 Brushless DC motor
4160 Anti-spill back valve
4170 Air circuit
4180 Supplemental oxygen
4200 Electrical components
4202 Printed Circuit Board Assembly (PCBA)
4210 Power Supply
4220 Input devices
4270 Transducers
5000 Humidifier
5002 Humidifier inlet
5004 Humidifier outlet
5006 Humidifier base
5110 Reservoir
5120 Conductive portion
5130 Humidifier reservoir dock
5135 Locking lever
5150 Water level indicator
5240 Heating element

The invention claimed is:

1. A vent structure for a respiratory therapy system, the vent structure comprising:

a vent housing at least partly forming an interior volume and comprising: a first tube portion at least partly forming a first port configured to connect in use to an air circuit;

a second tube portion at least partly forming a second port configured to connect in use to a plenum chamber of a patient interface;

a gap between the first tube portion and the second tube portion;

wherein the first tube portion and the second tube portion at least partly form a first flow path for pressurized air to flow through the interior volume from the first port and the second port in a first direction and from the second port to the first port in a second direction; and wherein the first tube portion and the second tube portion at least partly form a second flow path through the gap from the interior volume to surrounding ambient air; and a membrane extending into the gap, the membrane comprising a central aperture at least partly forming the first flow path and configured to be open when pressurized air flows through the membrane in the first direction and the second direction, wherein the membrane is positioned within the vent housing such that a first side of the membrane and a second side of the membrane opposite the first side of the membrane are both exposed to air flow in the first flow path in use, wherein the membrane is configured to be deflected into a first configuration, in use, by pressurized air flowing in the first flow path in the first direction to at least partially block airflow into the gap, and wherein the membrane is configured to be deflected into a second configuration, in use, by pressurized air flowing in the first flow path in the second direction to allow pressurized air to flow from the first flow path to the second flow path, and wherein a diameter of the central aperture is smaller than a diameter of an inner surface of the first tube portion and a diameter of an inner surface of the second tube portion.

2. The vent structure of claim 1, wherein the vent housing at least partly forms a plurality of vent holes that at least partly form part of the second flow path and are configured to allow pressurized air to exit to the surrounding ambient air, the vent holes being positioned adjacent an outer perimeter of the membrane.

3. The vent structure of claim 1, wherein the membrane is annular in shape.

4. The vent structure of claim 1, wherein the membrane comprises one or more protrusions extending from an inner perimeter of the membrane towards the centre of the central aperture.

5. The vent structure of claim 1, wherein the first tube portion comprises a first flange extending away from the first flow path at an end of the first tube portion distal from the second port.

6. The vent structure of claim 5, wherein the membrane is positioned adjacent and substantially parallel to the first flange.

7. The vent structure of claim 5, wherein the gap is sized to allow pressurized air to flow through the second flow path when the pressure in the first flow path drops below a threshold pressure to allow carbon dioxide washout in use.

8. The vent structure of claim 1, wherein the first tube portion comprises a retaining member configured to retain the membrane.

9. The vent structure of claim 8, wherein the retaining member engages the central aperture of the membrane.

10. The vent structure of claim 1, wherein the first tube portion comprises a plurality of tube passive vent holes configured to allow pressurized air to flow directly from the first flow path to the surrounding ambient air.

11. The vent structure of claim 1, wherein the membrane comprises a plurality of membrane passive vent holes configured to allow air to flow from the first flow path to the second flow path when the membrane is in the first configuration.

12. The vent structure of claim 1, wherein the membrane is not attached to the vent housing.

13. The vent structure of claim 12, wherein the entire membrane is configured to be displaced away from the second port when pressurized air flows in the first flow path in the second direction to allow the pressurized air to flow from the first flow path to the second flow path.

14. The vent structure of claim 1, wherein an outer portion of the membrane is fixed to the vent housing.

15. The vent structure of claim 14, wherein an inner portion of the membrane is configured to deflect in a direction away from the second port when pressurized air flows in the first flow path in the second direction to allow pressurized air to flow from the first flow path to the second flow path.

16. The vent structure of claim 15, wherein the inner portion of the membrane is configured to deflect in a direction towards the second port when pressurized air flows in the first flow path in the first direction to at least partially block airflow into the gap.

17. The vent structure of claim 1, wherein at least a portion of the second flow path extends radially relative to the vent housing.

18. A patient interface comprising:
a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;
a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and
the vent structure according to claim 1,
wherein the vent structure is configured to allow a flow of gases exhaled by the patient from an interior of the plenum chamber to ambient, said vent structure being sized and shaped to maintain the therapeutic pressure in the plenum chamber in use,
wherein the patient interface is configured to allow the patient to breathe from ambient through their mouth in the absence of a flow of pressurised air through the plenum chamber inlet port, or the patient interface is configured to leave the patient's mouth uncovered.

19. A respiratory therapy system comprising:
a vent structure according to claim 1;
at least one air circuit configured to supply the flow of air at the therapeutic pressure to the patient interface; and
a patient interface comprising:
a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; and
a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;
wherein the patient interface is configured to allow the patient to breath from ambient through their mouth in the absence of a flow of pressurised air through the plenum chamber inlet port, or the patient interface is configured to leave the patient's mouth uncovered.

* * * * *